(12) United States Patent
Adams et al.

(10) Patent No.: US 9,446,034 B2
(45) Date of Patent: Sep. 20, 2016

(54) PYRAZOLYLAMINOPYRIDINES AS INHIBITORS OF FAK

(71) Applicant: GlaxoSmithKline LLC, Wilmington, DE (US)

(72) Inventors: Jerry Leroy Adams, Collegeville, PA (US); Thomas H. Faitg, Collegeville, PA (US); Neil W. Johnson, Collegeville, PA (US); Hong Lin, Collegeville, PA (US); Xin Peng, Collegeville, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

(21) Appl. No.: 14/887,763

(22) Filed: Oct. 20, 2015

(65) Prior Publication Data

US 2016/0095841 A1    Apr. 7, 2016

Related U.S. Application Data

(63) Continuation of application No. 14/672,477, filed on Mar. 30, 2015, now abandoned, which is a continuation of application No. 14/047,688, filed on Oct. 7, 2013, now Pat. No. 9,012,479, which is a continuation of application No. 13/126,064, filed as application No. PCT/US2009/062163 on Oct. 27, 2009, now abandoned.

(60) Provisional application No. 61/242,423, filed on Sep. 15, 2009, provisional application No. 61/178,517, filed on May 15, 2009, provisional application No. 61/108,568, filed on Oct. 27, 2008.

(51) Int. Cl.
*A61K 31/4439* (2006.01)
*C07D 401/12* (2006.01)

(52) U.S. Cl.
CPC .................. *A61K 31/4439* (2013.01)

(58) Field of Classification Search
None
See application file for complete search history.

(56) References Cited

U.S. PATENT DOCUMENTS

2011/0166139 A1    7/2011    Barlaam et al.

FOREIGN PATENT DOCUMENTS

| WO | WO 00/14105 A1 | 3/2000 |
| WO | WO 2004/007481 A2 | 1/2004 |
| WO | WO2007/009524 A1 | 1/2007 |
| WO | WO2008/115369 A2 | 9/2008 |
| WO | WO2009/153589 A1 | 12/2009 |

OTHER PUBLICATIONS

Schultze et al. Expert Opin. Investig. Drugs (2010) 19(6):777-788.*
Cancer Drug Design and Discovery, Neidle, Stephen,ed. (Elsevier/Academic Press), pp. 427-431 (2008).*
Adachi, I, et al., *Chemical & Pharmaceutical Bulletin*, 35(8):3235-52 (1987).
Agochiya, et al., *Oncogene*, 18:5646-5653 (1999).
Beviglia, et al, *Biochem J.*, 373:201-210 (2003).
Einzig, et. al., *Proc. Am. Soc. Clin. Oncol.*, 20:46 (2001).
Forastire, et. al., *Sem. Oncol.*, 20:56 1990).
Gabarro-Niecko, et al., *Cancer Metastasis Rev*, 22:359-374 (2003).
Grisaru-Granovsky, et al., *Int. J. Cancer*, 113:372-378 (2005).
Halder, et al, *Clin. Cancer Res.*, 11:8829-8836 (2005).
Holmes, et al., *J. Nat. Cancer Inst.*, 83:1797 (1991).
Honma, T. ,et al. *J. Med. Chem.*, 44 (26):4628-4640 (2001).
Kearns, C.M., et. al., *Seminars in Oncology*, 3(6) p. 16-23 (1995).
Kingston, et al., *Studies in Organic Chemistry*, "New trends in Natural Products Chemistry" 26 (1986).
Kumar, *J. Biol. Chem*, 256:10435-10441 (1981).
Markman, et al., *Yale Journal of Biology and Medicine*, 64:583 (1991).
McGuire, et al., *Ann. Intern. Med.*, 111:273 (1989).
McLean, et al, *Nat Rev Cancer*, 7:505-515 (2005).
Mitra, et al, *Oncogene*, 25:4429-4440 (2006).
Mitra, et al, *Oncogene*, 25:5969-5984 (2006).
Owens, et al., *Cancer Research*, 55:2752-2755 (1995).
Recher, et al., *Cancer Research*, 64:3191-3197 (2004).
Schiff, et al., *Nature*, 277:665-667 (1979).
Schiff, et al., *Proc. Natl. Acad, Sci. USA*, 77:1561-1565 (1980).
Smith, et al, *Melanoma Res.*, 15:357-362 (2005).
van Nimwegen, et al 2005, *Cancer Res.*, 65:4698-4706 (2005).
Wani, et al., *J. Am. Chem, Soc.*, 93:2325 (1971).
Woo, et. al., *Nature*, 368:750 (1994).
Xu, et al. *Cell Growth and Diff*, 7:413-418 (1996).
Zhao and Guan, et al., *Cancer Metastasis Rev.*, 28:35-49 (2009).
*A Dose Escalation Study to Assess Safety of GSK2256098 (FAK Inhibitor)*, CiinicalTrials.gov, Trial 1 of 6. Sep. 5, 2013.
*A Study of GSK2256098 and Trametinib in Advanced Pancreatic Cancer*, ClinicalTrials.gov, Trial 5 of 6, Apr. 23, 2015.

* cited by examiner

*Primary Examiner* — Emily Bernhardt
(74) *Attorney, Agent, or Firm* — Wayne J. Dustman; Edward R. Gimmi

(57) ABSTRACT

The present invention relates to a compound of formula (I):

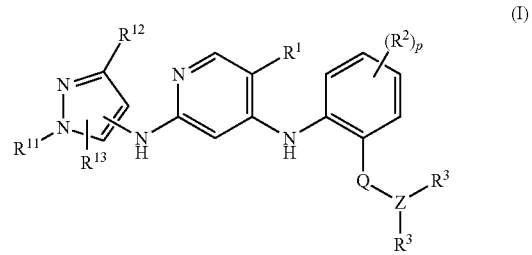

or a pharmaceutically acceptable salt thereof, wherein $R^1$, $R^2$, $R^3$, $R^{11}$, $R^{12}$, $R^{13}$, Q, Z, and p are as described herein. Compounds of the present invention are useful for the treatment of cancers.

2 Claims, No Drawings

SEQUENCE LISTING

<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Peptide substrate

<400> SEQUENCE: 1

Arg Arg Arg Arg Arg Arg Ser Glu Thr Asp Asp Tyr Ala Glu Ile Ile
1               5                   10                  15
Asp

<210> SEQ ID NO 2
<211> LENGTH: 14
<212> TYPE: PRT
<213> ORGANISM: Artificial Sequence
<220> FEATURE:
<223> OTHER INFORMATION: Peptide substrate

<400> SEQUENCE: 2

Cys Ser Glu Thr Asp Asp Tyr Ala Glu Ile Ile Asp Cys His
1               5                   10

PYRAZOLYLAMINOPYRIDINES AS INHIBITORS OF FAK

This application is a Continuation of U.S. application Ser. No. 14/672,477 filed 30 Mar. 2015, which is a continuation of U.S. application Ser. No. 14/047,688 filed 7 Oct. 2013, now U.S. Pat. No. 9,012,479, which is a continuation of U.S. application Ser. No. 13/126,064 filed 26 Apr. 2011, which is a 371 of International Application No. PCT/US09/62163 filed 27 Oct. 2009, which claims priority from U.S. Provisional Application No. 61/242,423 filed 15 Sep. 2009, which claims priority from U.S. Provisional Application No. 61/178,517 filed 15 May 2009; which claims priority from U.S. Provisional Application No. 61/108,568 filed 27 Oct. 2008, which are incorporated herein in their entirety.

AREA OF THE INVENTION

This invention relates to a class of pyrazolylaminopyridines that inhibit Focal Adhesion Kinase (FAK), as well as compositions thereof. Compounds of the present invention are useful in the treatment of proliferative diseases including, but not limited to cancer.

BACKGROUND OF THE INVENTION

Tyrosine kinases play an important role in the regulation of many cell processes including cell proliferation, cell survival, and cell migration. It is known that certain tyrosine kinases become activated by mutation or are abnormally expressed in many human cancers. For example, the epidermal growth factor receptor (EGFR) is found mutated and/or overexpressed in breast, lung, brain, squamous cell, gastric, and other human cancers. Selective inhibitors of the tyrosine kinase activity of EGFR have been shown to be of clinical value in treatment of cancers with mutated and/or overexpressed EGFR. Thus, selective inhibitors of particular tyrosine kinases are useful in the treatment of proliferative diseases such as cancer.

FAK (encoded by the gene PTK2) is a non-receptor tyrosine kinase that integrates signals from integrins and growth factor receptors. FAK has been reported to play a role in the regulation of cell survival, growth, adhesion, migration, and invasion (McLean et al 2005, Nat Rev Cancer 5:505-515). Furthermore, FAK is regulated and activated by phosphorylation on multiple tyrosine residues. Overexpression of FAK mRNA and/or protein has been documented in many solid human tumors, including but not limited to, cancers of the breast, colon, thyroid, lung, ovary, and prostate; but also including cancers of hematological origin, including but not limited to leukemia such as acute myeloid leukemia (AML). (Owens et al. 1995, Cancer Research 55: 2752-2755; Agochiya et al. 1999, Oncogene 18: 5646-5653; Gabarro-Niecko et al. 2003, Cancer Metastasis Rev. 22:359-374; Recher et al. 2004, Cancer Research 64:3191-3197; Zhao and Guan, 28:35-49, 2009, Cancer Metastasis Rev.). More significantly, there is evidence that phosphorylated FAK is increased in malignant compared to normal tissues (Grisaru-Granovsky et al. 2005, Int. J. Cancer 113: 372-378) and could represent a prognostic marker of metastasis. FAK activity is clearly implicated in advanced and metastatic human cancer (Zhao and Guan, 28:35-49, 2009, Cancer Metastasis Rev.).

Elimination of FAK by RNAi or expression of a FAK dominant negative has been shown to induce loss of adhesion and cell death in human breast and melanoma cell lines, and to augment docetaxel-mediated apoptosis in ovarian cancer cells (Beviglia et al 2003, Biochem J. 373:201-210, Smith et al 2005, Melanoma Res. 15:357-362, Halder et al 2005, Clin. Cancer Res. 11:8829-8836). However, inhibition of FAK in normal human fibroblasts or immortalized mammary cells (MCF 10A) was found not to cause loss of attachment or apoptosis (Xu et al. 1996 Cell Growth and Diff 7:413-418). Inhibition of FAK by dominant negative expression has also been shown to reduce tumor growth and eliminate lung metastasis of mammary adenocarcinoma cells in a syngeneic rat model (van Nimwegen et al 2005, Cancer Res. 65:4698-4706). Similarly, inhibition of FAK by shRNA inhibited lung metastasis and reduced lethality by 40% in a syngeneic mouse model (Mitra et al 2006, Oncogene 25: 4429-4440). In this study, transient re-expression of wild-type, but not kinase-dead FAK, reversed the shRNA phenotypes Inhibition of FAK by dominant negative expression in mouse 4T 1 carcinoma cells reduced tumor growth and angiogenesis in mice (Mitra et al 2006, Oncogene 25:5969-5984). Furthermore, loss of FAK catalytic activity (reconstitution of FAK−/− cells with kinase-dead FAK) reduced growth of v-Src tumors in mice and decreased angiogenesis.

Thus, there is strong evidence to suggest that inhibition of FAK activity induces apoptosis, loss of adhesion, inhibition of cell growth and migration, and that such inhibition reduces angiogenesis. Accordingly, compounds that inhibit FAK activity would be useful for the treatment of cancer.

SUMMARY OF THE INVENTION

The present invention relates to compounds of formula (I):

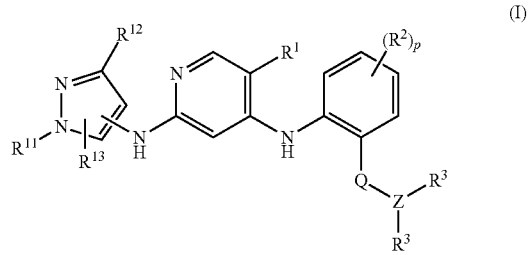

or a salt thereof, wherein:

$R^1$ is halo, $CF_3$, $C_1$-$C_6$-alkyl, isopropenyl, ($C_2$-$C_6$-alkylene) $C_3$-$C_6$-cycloalkyl, $C_1$-$C_6$-alkoxy, or cyano;

in $R^2$ when p is other than 0, each $R^2$ is independently F, Cl, $CF_3$, methyl, methoxy, $CH_2CF_3$, —$(X)_q$—$C_1$-$C_4$-alkylene-$R^4$, —(X—$C_1$-$C_4$-alkylene)$_q$-$NR^5$—C(O)—$R^6$, —(X—$C_1$-$C_4$-alkylene)$_q$-($NR^5$)$_q$—$SO_x$—$R^7$, —(X—$C_1$-$C_4$-alkylene)$_q$-Y—N($R^8$)$_2$; a 5- to 6-membered heterocycloalkyl-($R^9$)$_q$ group, or a 5- to 6-membered)heteroaryl-($R^{10}$)$_r$ group;

$R^3$ is independently H, $C_3$-$C_6$-cycloalkyl, $C_1$-$C_6$-alkyl, $C_1$-$C_6$alkoxy, $C_1$-$C_6$-alkylene-$R^4$, O—$C_1$-$C_6$-alkylene-$R^4$, or, the $R^3$ groups, together with Z, form a 5- to 6-membered cyclic ring optionally substituted with methyl, $C_1$-$C_4$-alkylene-$R^4$, or $C_3$-$C_6$-cycloalkyl;

$R^4$ is H, -(Q)$_q$-N($R^8$)$_2$, OH, SH, $C_1$-$C_6$-alkoxy, $C_1$-$C_6$-thioalkyl, or a 5- to 6-membered heterocycloalkyl-($R^9$)$_q$ group;

$R^5$ is H or $C_1$-$C_6$-alkyl;

$R^6$ is H, $C_1$-$C_6$-alkyl, $C_1$-$C_6$-alkoxy, N($R^8$)$_2$, or a 5- to 6-membered) heteroaryl-($R^{10}$)$_r$ group;

R⁷ is C₁-C₆-alkyl, phenyl-(R⁹)$_q$, or 5- to 6-membered) heteroaryl-(R¹⁰)$_r$,

R⁸ is independently H, C₁-C₆-alkyl, —O—C₁-C₆-alkyl or, together with the nitrogen atom to which they are attached, form a 5- or 6-membered heterocycloalkyl group;

R⁹ is H, C₁-C₆-alkyl, C₁-C₆-alkoxy, -(Q)$_q$-N(R⁸)₂, -Q-C₁-C₆-alkyl, —C₁-C₆alkyl-R⁴, or 5- to 6-membered heterocycloalkyl;

R¹⁰ is H, C₁-C₆-alkyl, C₁-C₆-alkoxy, or -Q-C₂-C₆-alkyl;

R¹¹ is C₁-C₆-alkyl, CF₃, —CH₂CF₃, -(Q)$_q$-C₁-C₄-alkylene-R⁴, -Q-N(R⁸)₂, phenyl-(R⁵)$_s$, a 5- to 6-membered heterocycloalkyl-(R⁹)$_q$ group, or a 5- to 6-membered heteroaryl-(R¹⁰)$_r$ group;

R¹² is H, C₁-C₆-alkyl, F, Cl, CF₃, OH, CN, nitro, COOH, —COO—C₁-C₆-alkyl, —Y—N(R⁸)₂, C₃-C₆-cycloalkyl-R¹⁴, —(X)$_q$—C₁-C₆-alkylene-R⁴, —(X—C₁-C₆-alkylene)$_q$-NR⁵—C(O)—R⁶, —(X—C₁-C₆-alkylene)$_q$-(NR⁵)$_q$-SO$_x$—R⁷, —(X—C₁-C₆-alkylene)$_q$-Y—N(R⁸)₂, heterocycloalkyl-(R⁹)$_q$, heteroaryl-(R¹⁰)$_r$, or phenyl-(R¹⁵)$_s$;

R¹³ is H, F, Cl, C₁-C₆-alkyl, or C₃-C₆-cycloalkyl; or R¹² and R¹³, together with the carbon atoms to which they are attached, form a fused 5- or 6-membered carbocycloalkyl or heterocycloralkyl group;

R¹⁴ is independently H, C₁-C₆-alkyl, —NR⁵—SO₂—R⁷, —Y—N(R⁸)₂, or —(X)$_q$—C₁-C₆-alkylene-R⁴;

R¹⁵ is independently F, Cl, CF₃, C₁-C₃-alkyl, or C₁-C₃-alkoxy;

p is 0, 1, 2, or 3;
q is 0 or 1;
r is 0, 1, or 2;
s is 0, 1, 2, or 3;
x is 1 or 2;
Q is —C(O)—, —S(O)—, or —SO₂—;
X is NR⁵, O, S, —S(O)—, or —SO₂—;
Y is a bond, SO₂, or C(O); and
Z is N or CR⁵.

In a further embodiment, the present invention relates to a composition comprising a) the compound of formula (I) or a pharmaceutically acceptable salt thereof; and b) a pharmaceutically acceptable excipient.

In a further embodiment, the present invention relates to a method of treating a proliferative disease such as cancer or an abnormal angeogensis disease such as macular degeneration, comprising administering to a patient in need thereof a pharmaceutically effective amount of the compound of formula (I).

DETAILED DESCRIPTION OF THE INVENTION

In another aspect, the present invention relates to compounds of formula (Ia):

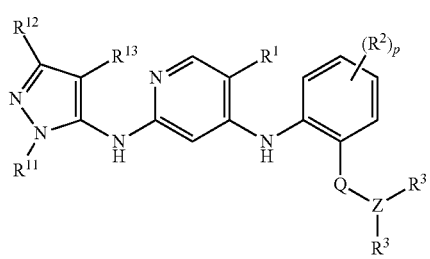

(Ia)

wherein the various groups are the same as set out above for formula (I); or a pharmaceutically acceptable salt thereof In another aspect, the present invention is represented by a compound of formula (Ib):

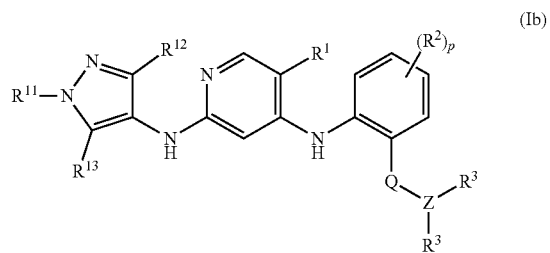

(Ib)

wherein the various groups are the same as set out above for formula (I); or a pharmaceutically acceptable salt thereof.

In another aspect of the present invention, Q is C(O) and Z is N.

In another aspect of the present invention, R¹ is Cl, CF₃, or CN;

In another aspect of the present invention, R² is F;

In another aspect of the present invention, one R³ is methyl and the other R³ is H;

In another aspect of the present invention, one R³ is methoxy and the other R³ is H;

In another aspect of the present invention, R¹¹ is C₁-C₆-alkyl;

In another aspect of the present invention, R¹² is C₁-C₆-alkyl, hydroxymethyl, or cyclopropyl;

In another aspect of the present invention, R¹³ is H;

In another aspect of the present invention, p is 0 or 1;

As used herein, "halo" refers to fluoro, chloro, or bromo.

"C₁-C₆-alkyl" refers to a linear or branched alkyl group including methyl, ethyl, n-propyl, isopropyl, n-butyl, isobutyl, t-butyl, n-pentyl, and n-hexyl.

"C₁-C₆-alkoxy" refers to C₁-C₆-alkyl-O— groups, including methoxy, ethoxy, n-propoxy, iso-propoxy, and n-butoxy groups.

The term "alkylene" (e.g., C₂-C₄-alkylene or C₁-C₆-alkylene) refers to a linear or branched hydrocarbon radical having the specified number of carbon atoms. The group "-alkylene-R⁴" refers to a substituted or unsubstituted alkyl group having the specified number of carbon atoms; thus, where R⁴ is H, "alkylene" is synonymous with "alkyl"; otherwise, alkylene is a bivalent radical. Examples of —(X)$_q$—C₂-C₄-alkylene-R⁴ include —CH₂CH₂—N(CH₃)₂, —CH₂CH₂—OH, —CH₂CH(CH₃)—OCH₃, —N(CH₃)—CH₂CH₂CH₂-piperidinyl; —O—CH₂CH(CH₃)—OCH₃; and the like.

C₃-C₆-cycloalkyl refers to a cyclopropyl, cyclobutyl, cyclopentyl, or cyclohexyl group.

As used herein, "5- or 6-membered heterocycloalkyl" refers to a 5- or 6-membered cycloaliphatic group that includes an O, N, or S heteroatom or a combination thereof. Examples of suitable heterocycloalkyl groups include pyrrolidinyl, pyrrolidinonyl, piperidinyl, piperazinyl, oxopiperazinyl, morpholino, and thiomorpholino groups.

The R⁸ groups may, together with the nitrogen atom to which they are attached, form a 5- to 6-membered cyclic ring, examples of which include pyrrolidinyl, pyrrolidinonyl, piperidinyl, piperazinyl, oxopiperazinyl, morpholino, and thiomorpholino groups.

The term "heteroaryl" refers to a 5- or 6-membered aromatic group containing at least one N, O, or S atom. Examples of suitable heteroaryl groups include pyridinyl, pyridazinyl, pyrimidinyl, pyrazinyl, pyrrolyl, furyl, thienyl, pyrazolyl, imidazolyl, furazanyl, oxazolyl, thiazolyl, isoxazolyl, 1,2,3-triazolyl, 1,2,4-triazolyl, tetrazolyl, and isothiazolyl.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication.

The skilled artisan will appreciate that pharmaceutically acceptable salts of compounds of formula (I) may be prepared. More particularly, inasmuch as compounds according to formula (I) contain a basic functional group—and may include an acid functional group—they are capable of forming pharmaceutically acceptable salts by treatment with a suitable acid or base. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, malic acid, malonic acid, tartaric acid, citric acid, salicylic acid, benzoic acid, tannic acid, formic acid, stearic acid, lactic acid, ascorbic acid, p-toluenesulfonic acid, oleic acid, and lauric acid.

Suitable bases include inorganic bases, such as hydrides, hydroxides and carbonates of lithium, sodium, potassium, calcium, magnesium, and zinc, as well as organic bases such as arginine, choline, diethylenetriamine, dimethylamine, ethylenediamine, imidazole, lysine, morpholine, proline, and trimethylamine.

As used herein, the term "a compound of formula (I)" or "the compound of formula (I)" refers to one or more compounds according to formula (I). The compound of formula (I) may exist in a crystalline or noncrystalline form, or as a mixture thereof. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates." Hydrates include stoichiometric hydrates as well as compositions containing variable amounts of water. The present invention includes all such solvates.

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Pharmaceutical compositions may be presented in unit dose forms containing a predetermined amount of active ingredient per unit dose. Such a unit may contain, for example, 0.5 mg to 3500 mg, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of cancer will generally be in the range of 0.001 to 100 mg/kg body weight of recipient per day, suitably in the range of 0.01 to 10 mg/kg body weight per day. For a 70 kg adult the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Treatments

The compounds and compositions of the invention are used to treat cellular proliferation diseases. Disease states which can be treated by the methods and compositions provided herein include, but are not limited to, cancer, autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states. These compounds may also be used for treating macular degeration associated with neovacularization, such as AMD The compositions and methods provided herein are particularly deemed useful for the treatment of cancer including tumors such as skin, breast, brain, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

In comparison to related 2,4-diaminopyridine derivatives described elsewhere, the compounds of the present invention contain a hydroxamic acid ester function on the 4-aminophenyl ring at the 2-position and an aminopyrazole at 2-position on the pyridine ring. The hydroxamic acid ester function on the phenyl ring, as compared with the corresponding amide, increases potency against FAK on the order of 2-5 fold, particularly in vitro, and improves selectivity for FAK over other enzymes. The pyrazole reduces reactivity in the cytochrome P450s. Hence the combination of the hydroxamic acid ester construct on the phenyl ring with an aminopyrazole at 2 position on the pyridine ring provides compounds with enhanced safety and efficacy over other FAK inhibitors such as the 2,4-diaminopyridine derivatives.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the FAK inhibitors of this disclosure are not in and of themselves active or significantly active, but when combined with another therapy, which may or may not be active as a stand alone therapy, the combination provides a useful therapeutic outcome.

By the term "co-administering" and derivatives thereof as used herein is meant either simultaneous administration or any manner of separate sequential administration of an FAK inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical antineoplastic agents useful in the present invention include, but are not limited to: alkylating agents, anti-metabolites, anti-tumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above. Receptor kinase angiogenesis inhibitors may also find use in the present invention.

Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib mesylate (GLEEVEC®) is one example of a PDGFR inhibitor. Examples of VEGFR inhibitors include pazopanib, ZD6474, AZD2171, PTK787, sunitinib and sorafenib. Pazopanib and the compounds of Formula I an their salts are of particular interest.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl. Acad. Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)-N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R-(R*,R*)-2,3-dihydroxybutanedioate (1:2)(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-O-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-O-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H)pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

The following schemes illustrate how compounds of the present invention can be prepared. The specific solvents and reaction conditions referred to are also illustrative and are not intended to be limiting.

Schemes

Compounds of formula (I) may be prepared by the methods outlined in Scheme 1 below. Compounds of formula (II) and (III) are commercially available or may be synthesized using techniques conventional in the art. The L group for compound (III) represents a leaving group such as F or Cl. The compounds of formula (II) and (III) may be reacted under reflux or microwave conditions to afford intermediate (IV). The addition reaction is typically done using a polar, protic solvents such as n-butanol or iso-propanol. Alternatively, metal catalyzed coupling reaction conditions may be used. When compound (II) includes a functional group in need of protection, for example, a hydroxyl or amino group, an appropriate protecting group is advantageously used. Compounds of formula (IV) may then be reacted with an aminopyrazole (V), which is commercially available or which may be synthesized using techniques conventional in the art, to afford a compound of formula (I). The reaction is typically carried out in the presence of a metal catalyst, such as a palladium salt, along with an appropriate phosphine ligand. Alternatively, the reaction can be carried out with a catalytic amount of an acid such as hydrochloric or trifluoroacetic acid and in a suitable solvent such as water, 1,4-dioxane, or iso-propanol or a combination thereof; the reaction is advantageously carried out at an advanced temperature, for example, under refluxing conditions, or by using a microwave apparatus. The acid catalyst is typically present in an amount of 10-30 mol % with respect to the compound of formula (I).

Scheme 1

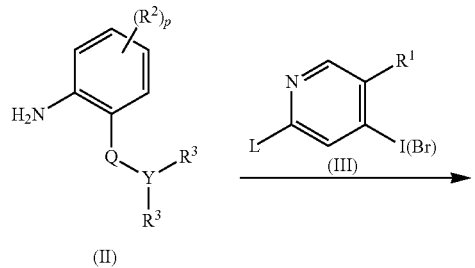

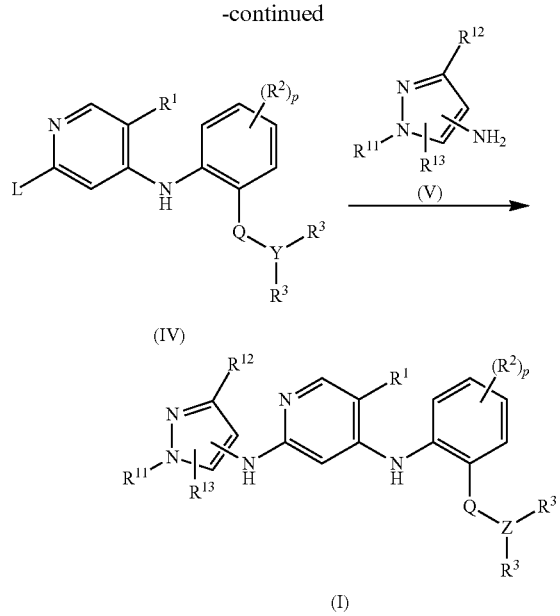

Compounds of formula (VIII) may be conveniently prepared by the methods outlined in Scheme 1, but starting with an appropriate anthranilamide (VI), as outlined in Scheme 2.

Scheme 2

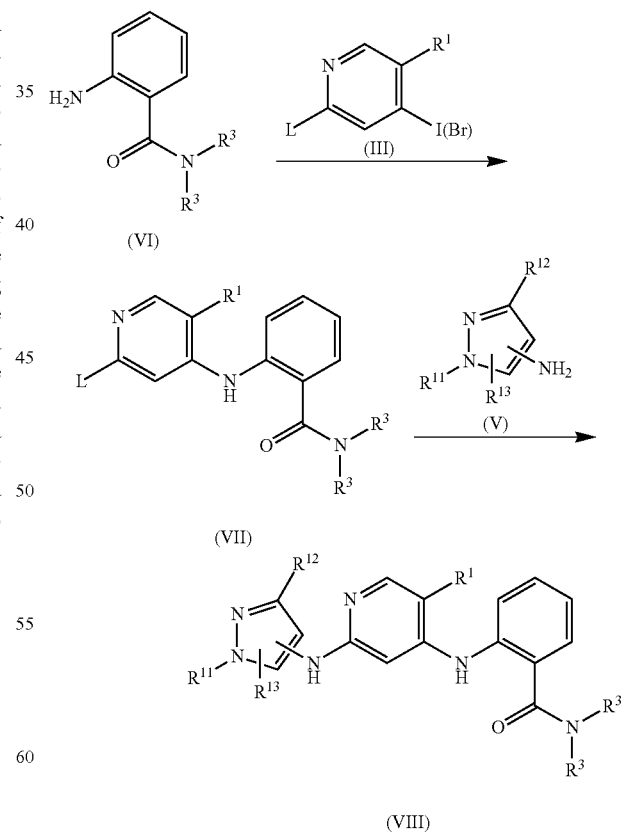

Compound (VI) may contain additional substituents. For example, as shown in Scheme 3, benzoxazine (IX), which is either commercially available or synthesized using techniques conventional in the art, can be ring-opened with an amine to form benzamide (X), which can then undergo addition with compound (III) to yield the compound of formula (XI).

Scheme 3

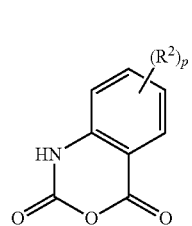 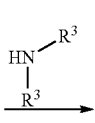

(IX)

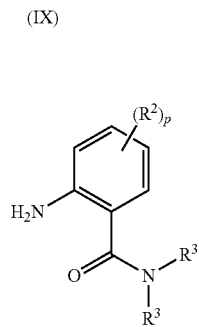

(X)

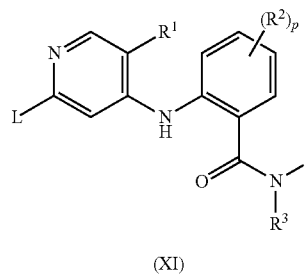

(XI)

A compound of formula (XII) may be prepared by reacting a compound of formula (II) with a compound of formula (XIII). This reaction can be carried out as described in Scheme 1. Compounds of formula (XII) may then be reacted with a compound of formula (XIV) to give compounds of formula (I). The reaction may be carried out in inert solvent, in the presence of a metal catalyst and appropriate ligand.

Scheme 4

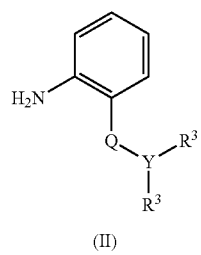 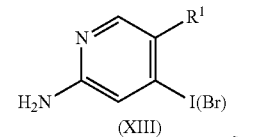

(II)                                 (XIII)

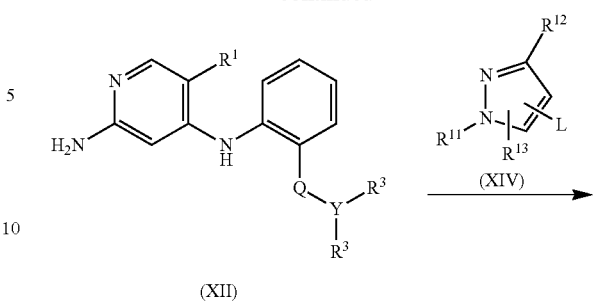

(XII)

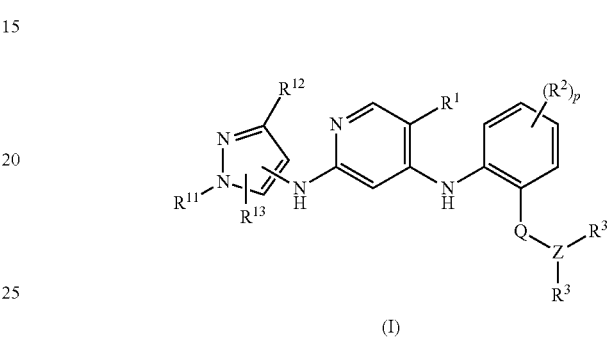

(I)

Certain compounds of formula (I) can also be prepared as outlined in Scheme 5. The amino group of the compound of formula (XV) can first be reacted with diketene followed by acylation and treatment with a hydrazine. Compound of formula (XVI) can then be obtained by treatment with acid, then reacted with a compound of formula (II) to give a compound of formula (I). This last reaction can be carried out as described in Scheme 1.

Scheme 5

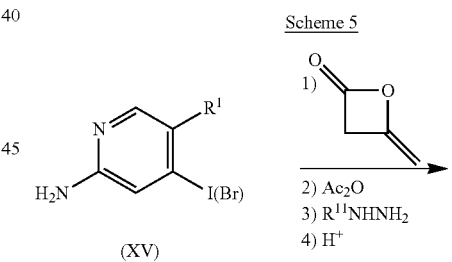 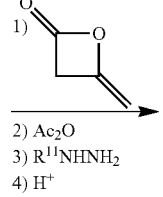

(XV)

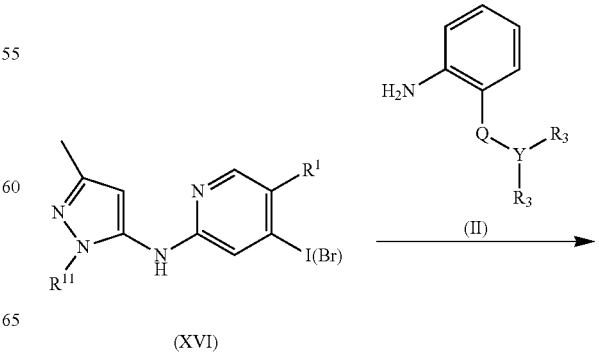

(XVI)

-continued

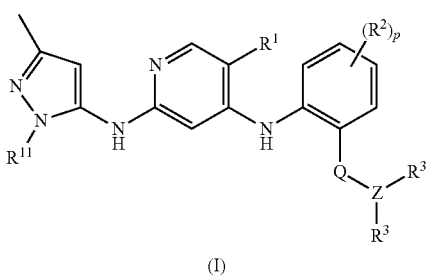

(I)

Compounds of formula (V) can be made by the condensation of a substituted hydrazine (XVIII) with the appropriate cyano-ketone (XVII), for example, according to the procedures of Honma, T. et al. *J. Med. Chem.* 2002, Vol. 44 (26), 4628-4640 or Adachi, I. et al. *Chemical & Pharmaceutical Bulletin* 1987, 35(8), 3235-52 as outlined in Scheme 6.

Scheme 6

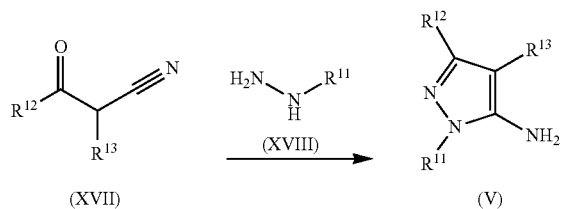

Scheme 7

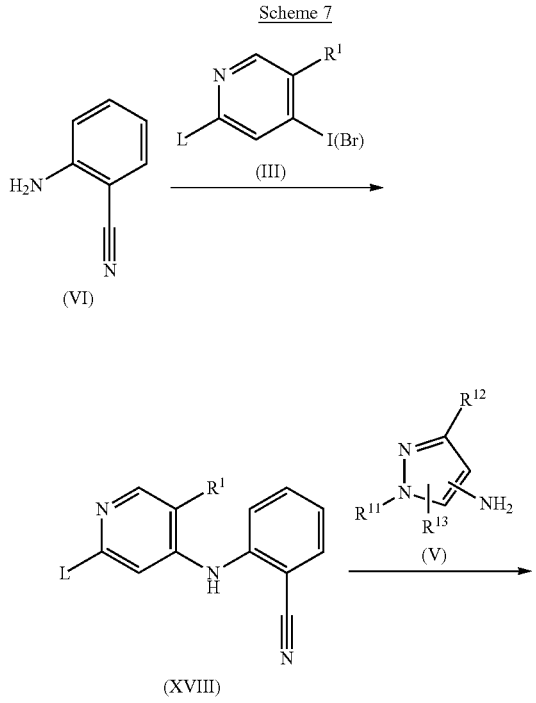

-continued

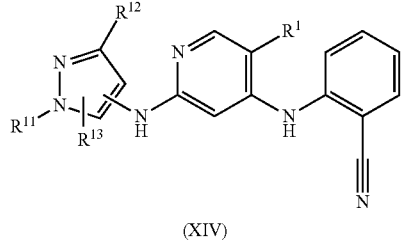

(XIV)

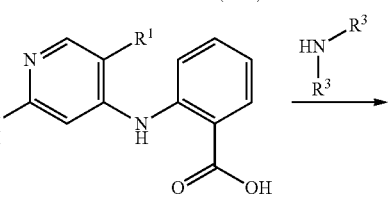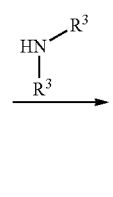

(XX)

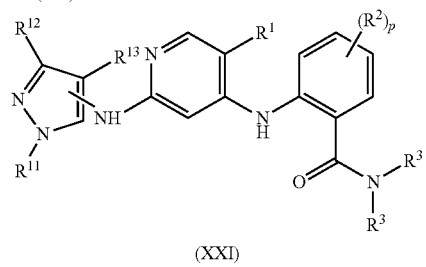

(XXI)

A compound of formula (XXI) can also be prepared as outlined in Scheme 7. The nitrile of formula (XIV) can be hydrolyzed to a carboxylic acid of formula (XX) and then coupled with an amine to give compounds of formula (XXI).

EXPERIMENTALS

Biochemical Assay for FAK Activity

Assay 1: GST-tagged (glutathione S-transferase-tagged) FAK was purchased from Invitrogen (PV3832) (www.invitrogen.com). The activity of FAK was measured by monitoring the phosphorylation of a peptide substrate (Ac-RRRRRRSETDDYAEIID-NH$_2$; (SEQ ID NO: 1) i.e. Ac-Arg-Arg-Arg-Arg-Arg-Arg-Ser-Glu-Thr-Asp-Asp-Tyr-Ala-Glu-Ile-Ile-Asp-NH$_2$) in the presence of a radio-labeled ATP. To measure inhibitors of FAK, compounds were first prepared as a 10× stock in 10% DMSO. A small portion of each solution (4 µL) was added to a 96-well plate (Corning, 3884). A 6-nM GST-FAK solution was prepared in 1.1× reaction buffer containing 44 mM HEPES, pH=7.2, 11 mM MgCl$_2$, 2.2 mM MnCl$_2$, 1.1 mM DTT and 0.011% Tween-20. Then, 20 µL of the 6 nM GST-FAK solution were pre-incubated with the compounds for 30 min at room temperature. The reaction was initiated by adding 16 µL of substrates (62.5 µM peptide, 5 µM ATP and ~0.02 mCi/mL $^{33}$P-γ-ATP) prepared in the above reaction buffer. The reaction was allowed to proceed for 90 min before being quenched with 40 µL of 1% H$_3$PO$_4$. A portion of the reaction mixture (60 µL) was transferred to a phospho-cellulose filter plate (Millipore; www.millipore.com, MAPHNOB50) and incubated for 20 minutes. The plate was filtrated, washed three times using 150 µL of 0.5% H$_3$PO$_4$ and dried at 50° C. for 30 min. After the addition of 60 µL Microscint-20 to the plate, radioactivity was measured using a TopCount (PerkinElmer; www.PerkinElmer.com).

Assay 2: Flag-His-TEV-FAK1 was prepared in-house. Full length Human FAK was expressed using baculovirus in Sf9 cells with N-terminal FLAG-6×His tags followed by a TEV cleavage site (FLAG-6×His-TEV-huFAK). The activity of FAK was measured by monitoring the phosphorylation of LANCE Ultra NH$_2$-(ULight)-CSETDDYAEIID-COOH (SEQ ID NO: 2) (C=cysteine S=serine, E=glutamic acid, T=threonine, D=aspartic acid, Y=tyrosine, A=alanine, I=isoluecine) substrate (purchased from Perkin Elmer Life Sciences). To measure inhibitors of FAK, compounds were first prepared as a 100× stock in 100% DMSO. A small portion of each compound solution (50 nL) was added to a black 384-well low-volume microtiter plate (Greiner 784076). A 1.2 nM Flag-His-TEV-FAK1 solution was prepared in 1× reaction buffer containing 40 mM Tris/Tris-HCL, 10 mM MgCl2, 1 mM CHAPS, at a pH of 7.5, with 1 mM DTT added. 2.5 ul of the 1.2 nM Flag-FAK solution was added to the plates and pre-incubated with the compounds for 30 min at room temperature. Then, 2.5 µL of substrate solution (0.1 µM of P2 FAK-tide specific substrate (Lance Ultra NH2-(ULight)-CSETDDYAEIID-COOH (SEQ ID NO: 2) from Perkin Elmer), 10 µM ATP and the 1× reaction buffer described above), was added to the plate to initiate the reaction. After incubating for 120 minutes at room temperature, the reaction is quenched by adding 5 uL of 20 mM EDTA and 5nMEu-Anti-pTyr antibody in 1× LANCE detection buffer. After a 30 minute incubation at room temperature, the plate is read on a Perkin Elmer Viewlux with a 320-340 nm excitation filter and measuring emission at 615 nm and 665 nm. The ratio of 665 nm/615 nm is used for data normalization.

The following Table A provides specific data for compounds of the below Examples as run in one or both of the foregoing assays. These data were generated in at least one run in the noted assay; repeats assay runs may have given or may give readouts that vary to some degree from these data.

TABLE A

| Example No. | Assay 1 FAK TRF PXC$_{50}$ | Assay 2 FAK H 31284A TRF PXC$_{50}$ |
|---|---|---|
| 1 | 8.7 | 7.8 |
| 2 | 8.8 | 8 |
| 3 | 9.2 | 8.3 |
| 4 | 9 | 8.2 |
| 5 | 9 | 8.1 |
| 6 | 8.9 | 8.3 |
| 7 | 9.1 | 8 |
| 8 | 9.2 | 8.3 |
| 9 | 9 | 8.2 |
| 10 | 9.1 | 8 |
| 11 | 8.7 | 8.2 |
| 12 | 8.6 | 8.3 |
| 13 | 9.3 | 8.7 |
| 14 | 8.6 | 7.7 |
| 15 | 8.6 | 7.7 |
| 16 | 8.9 | 7.7 |
| 17 | 8.9 | 7.4 |
| 18 | 8 | |
| 19 | 8.3 | 7.2 |
| 20 | 8 | 7.4 |
| 21 | 8.5 | 7.2 |
| 22 | 7.5 | 6.6 |
| 23 | 7.1 | 6.7 |
| 24 | 8.2 | 7.2 |
| 25 | 8.6 | 7.5 |
| 26 | 9.4 | 8.4 |
| 27 | 8.7 | 8.1 |
| 28 | 9.4 | 8.6 |
| 29 | 9.3 | 8.7 |
| 30 | 9.4 | 8.8 |
| 31 | 8.4 | |
| 32 | 9.4 | 9 |
| 33 | 9.4 | |
| 34 | 9.3 | |
| 36 | 9.4 | 8.8 |
| 37 | 8.4 | 7.7 |
| 38 | 6.6 | 6 |
| 39 | 9.4 | 8.3 |
| 40 | 8.9 | 8.6 |
| 41 | 9.4 | 8.7 |
| 42 | 7.9 | 7.3 |
| 43 | 8.3 | 7.6 |
| 44 | 8.2 | 7.2 |
| 45 | 8 | 7.2 |
| 46 | | 7.9 |
| 47 | | 8.6 |
| 49 | | 7.2 |
| 50 | | 7.9 |
| 51 | | 7.7 |
| 52 | | 8.2 |
| 53 | | 7.4 |
| 54 | | 7.5 |
| 55 | | 8 |
| 56 | | 7.8 |
| 58 | | 7.3 |
| 59 | 9.2 | 8.3 |
| 60 | | 7.9 |
| 61 | | 7.6 |
| 62 | | |
| 63 | | 7.3 |
| 64 | | 7.1 |
| 65 | | 7.8 |
| 66 | 8.7 | 7.5 |
| 67 | 7.2 | 8.3 |
| 69 | | 8.6 |
| 70 | | 8.2 |
| 71 | | 8.2 |
| 72 | | 8.6 |
| 73 | | 8.9 |

Chemistry Examples

The following chemistry examples are for illustrative purposes only and are not intended to limit the scope of the present invention. The compounds were named using ACD Name software (Advanced Chemistry Development, www.acdlabs.com). All compounds have pIC$_{50}$ of greater than 6.5 for the above-described biochemical assay.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass.; www.parker.com) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A, LCMS. Samples are introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% (H$_2$O 0.02% TFA) in vessel A and 100% (CH$_3$CN 0.018% TFA) in vessel B. The stationary phase is Aquasil (C18) and the column dimensions are 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um particle size and the column dimensions were 2.1 mm×50 mm. Detection was by UV at 214 nm, evaporative light-scattering (ELSD) and MS.

Method B, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50× 4.6 mm, 1.8 μm) eluting with $CH_3CN$: ammonium acetate buffer. The reactions were performed in the microwave (CEM, Discover).

1H-NMR (hereinafter "NMR") spectra were recorded at 400 MHz using a Bruker AVANCE 400 MHz instrument, with ACD Spect manager ver 10 using for reprocessing. Multiplicities indicated are: s=singlet, d=doublet, t=triplet, q=quartet, m=multiplet, dd=doublet of doublets, dt=doublet of triplets etc. and br indicates a broad signal.

Analytical HPLC: Products were analyzed by Agilent 1100 Analytical Chromatography system, with 4.5×75 mm Zorbax XDB-C18 column (3.5 m) at 2 mL/min with a 4 min gradient from 5% $CH_3CN$ (0.1% formic acid) to 95% $CH_3CN$ (0.1% formic acid) in $H_2O$ (0.1% formic acid) and a 1 min hold.

Preparative HPLC: Products were purified using a Gilson preparative chromatography system with a 75×30 mm I. D. YMC CombiPrep ODS-A column (5 m) (www.waters.com) at 50 mL/min with a 10 min gradient from 5% $CH_3CN$ (0.1% formic acid) to 95% $CH_3CN$ (0.1% formic acid) in $H_2O$ (0.1% formic acid) and a 2 min hold; alternatively, products were purified using an Agilent 1100 Preparative Chromatography system, with 100×30 mm Gemini C18 column (5 m) at 60 mL/min with a 10 min gradient from 5% $CH_3CN$ (0.1% formic acid) to 95% $CH_3CN$ (0.1% formic acid) in $H_2O$ (0.1% formic acid) and a 2 min hold.

Preparative normal phase chromatography was carried out using an Analogix IntelliFlash 280 System with Super-Flash Sepra Si 50 columns. Alternatively, reverse-phase HPLC was performed on Agilent using Zorbax SB-C18 column (21.2×250 mm, 7 μm) eluting with $CH_3CN$: ammonium acetate buffer (10 μM) at pH 6.8.

EXAMPLES

Example 1

1a) 2-[(2,5-Dichloro-4-pyridinyl)amino]-N-methyl-benzamide

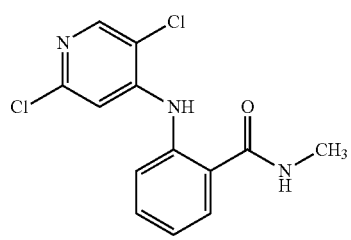 [SMILES: CNC(=O)c1ccccc1Nc1cc(Cl)ncc1Cl]

A 150-mL sealed tube was charged with 2,5-dichloro-4-iodopyridine (3.5 g, 12.78 mmol), 2-amino-N-methylbenzamide (1.919 g, 12.78 mmol) and tripotassium phosphate (8.14 g, 38.3 mmol) in 1,4-dioxane (100 mL). The reaction mixture was degassed with nitrogen for 10 min. Bis(2-diphenylphosphinophenyl)ether (DPEPhos, 0.688 g, 1.278 mmol) and Pd(OAc)$_2$ (0.115 g, 0.511 mmol) were added and the reaction mixture was heated in a 120° C. oil bath over night. The reaction mixture was filtered through celite, which was washed with dioxane. The solvent was evaporated to dryness and the solid was washed with EtOH (10 mL×3) to give 2.14 g (56%) of product as an off white solid.

1b) 2-[5-Chloro-2-(2-methyl-5-phenyl-2H-pyrazol-3-ylamino)-pyridin-4-ylamino]-N-methyl-benzamide

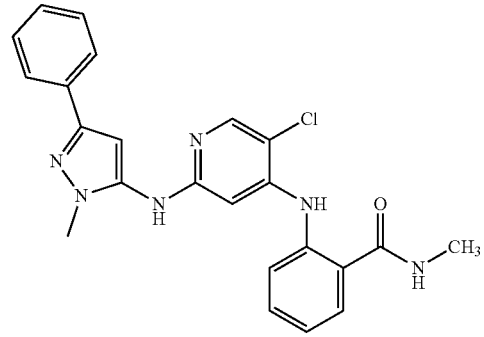 [SMILES: CNC(=O)c1ccccc1Nc1cc(Nc2cc(-c3ccccc3)nn2C)ncc1Cl]

A 50-mL sealed tube was charged with Pd(OAc)$_2$ (18 mg, 0.08 mmol) and 2,2'-bis (diphenylphosphino)-1,1'-binaphthyl (BINAP, 50 mg, 0.08 mmol) in 1,4-dioxane (10 mL). The mixture was degassed using bubbling nitrogen for 40 min and heated at 50° C. for 1 h. Then the mixture was cooled to room temperature whereupon 2-[(2,5-dichloro-4-pyridinyl)amino]-N-methyl-benzamide (300 mg, 1.01 mmol), 2-methyl-5-phenyl-2H-pyrazol-3-ylamine (704 mg, 4.06 mmol) and cesium carbonate (960 mg, 2.96 mmol) were added under an inert atmosphere. The tube was sealed and heated at 120° C. overnight. The reaction mixture was concentrated under reduced pressure and the crude product was purified by column chromatography (silica gel, eluted with dichloromethane-methanol (DCM-MeOH) 99:1 followed by purification by preparatory TLC to afford the desired compound as a off white solid (25 mg, 5%). $^1$H NMR (400 MHz, DMSO-d$_6$) δ 2.76 (d, 3H, J=4.52 Hz), 3.68 (s, 3H), 6.69 (s, 1H), 6.85 (s, 1H), 7.07-7.14 (m, 1H), 7.25-7.31 (m, 1H), 7.36-7.42 (m, 2H), 7.46-7.53 (m, 1H), 7.63 (d, 1H, J=8.08 Hz), 7.69 (d, 1H, J=7.4 Hz), 7.75 (d, 2H, J=7.16 Hz), 8.04 (s, 1H), 8.69 (brs, 1H), 8.81 (s, 1H), 10.13 (s, 1H). LC-MS calculated for $C_{23}H_{21}ClN_6O$ (M+H) 433.15, found 433.3. HPLC purity 96% at λ=200 nm and 99% at λ=260 nm.

Example 2

2-({5-Chloro-2-[(1H-methyl-1H-pyrazol-5-yl)amino]-4-pyridinyl}amino)-N-methylbenzamide

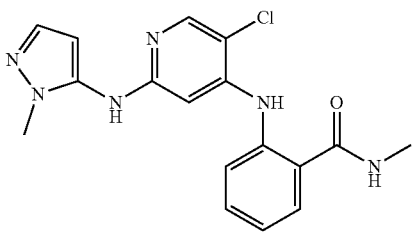 [SMILES: CNC(=O)c1ccccc1Nc1cc(Nc2ccnn2C)ncc1Cl]

A mixture of 2-[(2,5-dichloro-4-pyridinyl)amino]-N-methylbenzamide (100 mg, 0.338 mmol), 5-amino-1-methyl-1H-pyrazole (65.6 mg, 0.675 mmol), Cs$_2$CO$_3$ (220 mg, 0.675 mmol), tris(dibenzylideneacetone)dipalladium(0) (Pd$_2$(dba)$_3$, 61.8 mg, 0.068 mmol) and 4,5-bis(diphenylphosphino)-9,9-dimethylxanthene (Xantphos, 48.8 mg, 0.084 mmol) was heated at 150° C. in a microwave oven for 30 min. The reaction mixture was filtered, and the filtrate was concentrated, and the resulting crude product was purified by reverse phase HPLC and the product was treated with 2 N HCl to give 34 mg of product as an HCl salt (24%). LCMS (ES) m/z=357.1 (M+H); 1H NMR (400 MHz, methanol-d4) δ ppm 8.01 (s, 1H), 7.76-7.74 (m, 1H), 7.62-7.61 (m, 2H), 7.55 (d, J=2 Hz, 1H), 7.42-7.39 (m, 1H), 6.52 (s, 1H), 6.33 (d, J=2 Hz, 1H), 3.76 (s, 3H), 2.91 (s, 3H).

Example 3

2-({5-Chloro-2-[(1-ethyl-1H-pyrazol-5-yl)amino]-4-pyridinyl}amino)-N-methylbenzamide

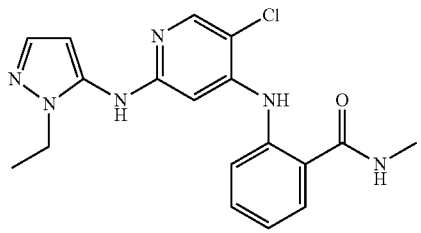 [SMILES: CCn1nccc1Nc1cc(Nc2ccccc2C(=O)NC)c(Cl)cn1]

The title compound was prepared substantially as described in Example 2 except using 5-amino-1-ethyl-1H-pyrazole instead of 5-amino-1-methyl-1H-pyrazole. LCMS (ES) m/z=371.1 (M+H); 1H NMR (400 MHz, METHANOL-d4) δ ppm 8.06 (m, 1H), 7.77-7.61 (m, 4H), 7.44-7.40 (m, 1H), 6.61 (m, 1H), 6.40 (s, 1H), 4.17-4.10 (m, 2H), 2.91 (s, 3H), 1.40 (tr, J=7.2 Hz, 3H).

Example 4

2-[(5-Chloro-2-{[3-methyl-1-(1-methylethyl)-1H-pyrazol-5-yl]amino}-4-pyridinyl)amino]-N-methylbenzamide

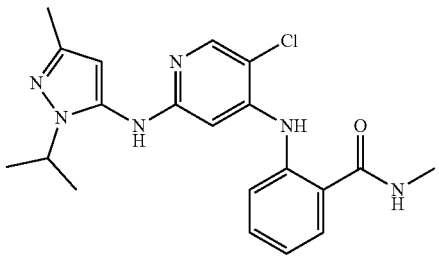 [SMILES: CNC(=O)c1ccccc1Nc1cc(Nc2cc(C)nn2C(C)C)ncc1Cl]

The title compound was prepared following the procedure in Example 2 except using 5-amino-1-isopropyl-1H-pyrazole instead of 5-amino-1-methyl-1H-pyrazole. LCMS (ES) m/z=399.2 (M+H); 1H NMR (400 MHz, methanol-d4) δ ppm 8.06 (s, 1H), 7.78-7.76 (m, 1H), 7.65-7.63 (m, 2H), 7.45-7.38 (m, 1H), 6.64 (s, 1H), 6.29 (s, 1H), 4.70-4.55 (m, 1H), 2.91 (s, 3H), 2.34 (s, 1H), 1.47 (d, J=6.8 Hz, 6H).

Example 5

2-({5-Chloro-2-[(1,3-dimethyl-1H-pyrazol-5-yl)amino]-4-pyridinyl}amino)-N-methylbenzamide

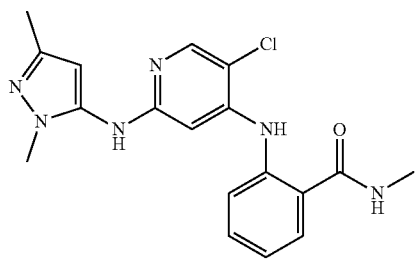 [SMILES: CNC(=O)c1ccccc1Nc1cc(Nc2cc(C)nn2C)ncc1Cl]

The title compound was prepared following the procedure in Example 2 except using 5-amino-1-methyl-3-methyl-1H-pyrazole instead of 5-amino-1-methyl-1H-pyrazole. LCMS (ES) m/z=371.1 (M+H); 1H NMR (400 MHz, methanol-d4) δ ppm 8.12 (s, 1H), 7.78-7.76 (d, J=7.6 Hz, 1H), 7.66-7.64 (m, 2H), 7.45-7.41 (m, 1H), 6.67 (s, 1H), 6.38 (s, 1H), 3.80 (s, 3H), 2.91 (s, 3H), 2.35 (s, 3H).

Example 6

2-({5-Chloro-2-[(3-cyclopropyl-1-methyl-1H-pyrazol-5-yl)amino]-4-pyridinyl}amino)-N-methylbenzamide

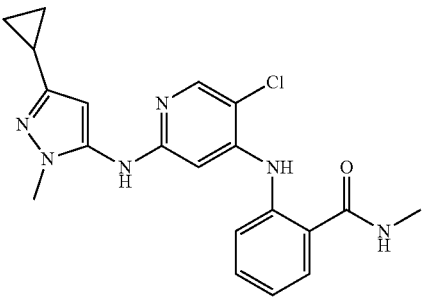 [SMILES: CNC(=O)c1ccccc1Nc1cc(Nc2cc(C3CC3)nn2C)ncc1Cl]

The title compound was prepared following the procedure in Example 2 except using 5-amino-3-cyclopropyl-1-methyl-1H-pyrazole instead of 5-amino-1-methyl-1H-pyrazole. LCMS (ES) m/z=397.1 (M+H); 1H NMR (400 MHz, methanol-d4) δ ppm 8.06 (s, 1H), 7.78-7.76 (m, 1H), 7.64-7.62 (m, 2H), 7.44-7.40 (m, 1H), 6.57 (s, 1H), 6.15 (s, 1H), 3.71 (s, 3H), 2.91 (s, 3H), 1.97-1.90 (m, 1H), 1.04-1.00 (m, 2H), 0.79-0.76 (m, 2H).

Example 7

2-({5-Chloro-2-[(1,3-dimethyl-1H-pyrazol-5-yl)amino]-4-pyridinyl}amino)-5-fluoro-N-methylbenzamide

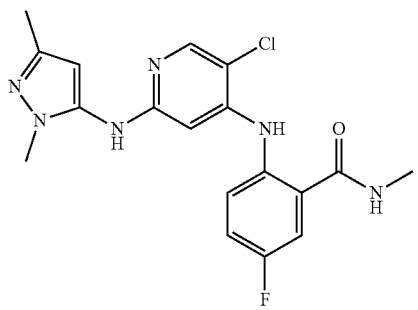 [SMILES: CNC(=O)c1cc(F)ccc1Nc1cc(Nc2cc(C)nn2C)ncc1Cl]

7a) 2-Amino-5-fluoro-N-methylbenzamide

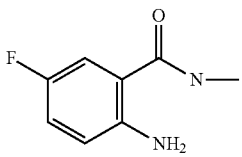

6-Fluoro-2H-3,1-benzoxazine-2,4(1H)-dione (200 mg, 1.104 mmol) was dissolved in dry tetrahydrofuran (THF) (10 mL), at which time methyl amine (3.31 mL, 6.63 mmol) was added. The reaction was stirred at room temperature for 1 h, then concentrated under vacuum. The crude product was purified on silica (Biotage, 40% EtOAc/hexene) to afford the title compound (120 mg, 65%) as a white solid. LC-MS (ES) m/z=169.1 (M+H)$^+$

7b) 2-({5-Chloro-2-[(1,3-dimethyl-1H-pyrazol-5-yl)amino]-4-pyridinyl}amino)-5-fluoro-N-methylbenzamide The title compound was prepared as a white solid by first reacting 2-amino-5-fluoro-N-methylbenzamide with 2,5-dichloro-4-iodopyridine to form 2-[(2,5-dichloro-4-pyridinyl)amino]-5-fluoro-N-methylbenzamide substantially according to the procedure of Intermediate 1, then reacting this intermediate with 1,3-dimethyl-1H-pyrazol-5-amine substantially according to the procedure of Example 2. LC-MS (ES) m/z=389.1 (M+H)$^+$, $^1$H NMR (CD$_3$OD, 400 MHz) δ 8.01 (s, 1H), 7.60 (m, 1H), 7.51 (m, 1H), 7.38 (m, 1H), 6.39 (s, 1H), 6.18 (s, 1H), 3.69 (s, 3H), 2.89 (s, 3H), 2.24 (s, 3H)

Example 8

2-({5-Chloro-2-[(1,3-dimethyl-1H-pyrazol-5-yl)amino]-4-pyridinyl}amino)-3-fluoro-N-methylbenzamide

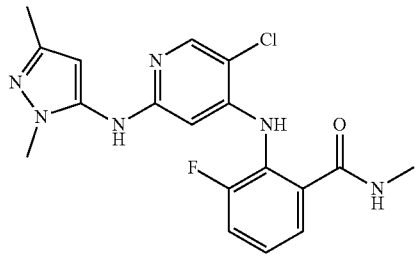 [SMILES: CNC(=O)c1cccc(F)c1Nc1cc(Nc2cc(C)nn2C)ncc1Cl]

8a) 2-Amino-3-fluoro-N-methylbenzamide

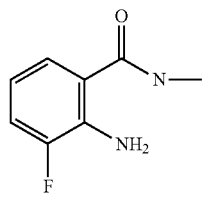

2-Amino-3-fluorobenzonitrile (3.8 g, 27.9 mmol) was dissolved in ethanol, water (15 mL) and THF (0.3 mL), potassium hydroxide (7.83 g, 140 mmol) was added. The mixture was heated at 85° C. for 12 h, cooled and filtered. The filtrate was concentrated and the residue was dissolved in dichloromethane (DCM, 50 mL). Then diisopropylethylamine (19.50 mL, 112 mmol) was added, followed by methyl amine (20.94 ml, 41.9 mmol) and bromo-tris-pyrrolidino phosphoniumhexafluorophosphate (PyBrOP, 21.79 g, 41.9 mmol). The reaction was stirred at room temperature for 2 h, washed with brine and dried over MgSO$_4$. The solvent was removed and the residue was purified by chromatography on silica gel (20% EtOAc/Hex) to give 1.5 g (35% yield) of intermediate a.

8b) 2-({5-Chloro-2-[(1,3-dimethyl-1H-pyrazol-5-yl)amino]-4-pyridinyl}amino)-3-fluoro-N-methylbenzamide The title compound was prepared as a white solid according to the procedure of Example 7, except using 2-amino-3-fluoro-N-methylbenzamide in place of 2-amino-5-fluoro-N-methylbenzamide: LC-MS (ES) m/z=389.1 (M+H)$^+$, $^1$H NMR (CD$_3$OD, 400 MHz) δ 8.01 (s, 1H), 7.50 (m, 3H), 6.14 (s, 1H), 5.87 (m, 1H), 3.65 (s, 3H), 2.89 (s, 3H), 2.22 (s, 3H)

The 2-{[5-chloro-2-(amino pyrazole)-4-pyridinyl]amino}-benzamide compounds illustrated in Table 1 were prepared from various 2-[(2,5-dichloro-4-pyridinyl)amino]-methylbenzamides and amino-pyrazoles substantially according to the procedure of Example 7. In the following tables, the dashed lines indicate the points of attachment. Thus, for Example 9, the compound corresponds to the following structure:

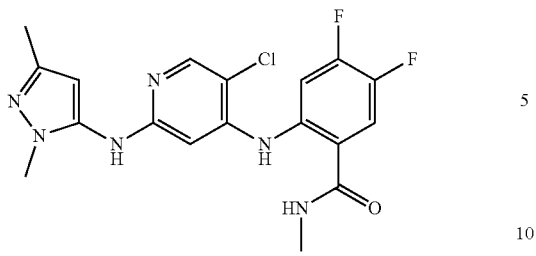

TABLE 1

| Ex. | Name | $R_a$ | $R_b$ | Data |
|---|---|---|---|---|
| 9 | 2-({5-Chloro-2-[(1,3-dimethyl-1H-pyrazol-5-yl)amino]-4-pyridinyl}amino)-4,5-difluoro-N-methylbenzamide | | | LC-MS (ES) m/z = 407.1 (M + H)+, 1H NMR (CD3OD, 400 MHz) δ 8.04 (s, 1H), 7.71 (m, 1H), 7.61 (m, 1H), 6.63 (s, 1H), 6.28 (s, 1H), 3.72 (s, 3H), 2.89 (s, 3H), 2.72 (s, 3H) |
| 10 | 2-({5-Chloro-2-[(1-ethyl-1H-pyrazol-5-yl)amino]-4-pyridinyl}amino)-4,5-difluoro-N-methylbenzamide | | | LC-MS (ES) m/z = 460.1 (M + H)+, 1H NMR (CD3OD, 400 MHz) δ 8.00 (s, 1H), 7.70 (m, 1H), 7.59 (m, 2H), 6.56 (s, 1H), 6.33 (s, 1H), 4.11 (m, 2H), 2.90 (m, 3H), 1.38 (m, 3H) |
| 11 | 5-Chloro-2-({5-chloro-2-[(1,3-dimethyl-1H-pyrazol-5-yl)amino]-4-pyridinyl}amino)-N-methylbenzamide | | | LC-MS (ES) m/z = 407.0 (M + H)+, 1H NMR (CD3OD, 400 MHz) δ 8.03 (s, 1H), 7.78 (m, 1H), 7.61 (m, 2H), 6.56 (s, 1H), 6.23 (s, 1H), 3.70 (s, 3H), 2.90 (s, 3H), 2.26 (s, 3H) |
| 12 | 5-Chloro-2-({5-chloro-2-[(1-ethyl-1H-pyrazol-5-yl)amino]-4-pyridinyl}amino)-N-methylbenzamide | | | LC-MS (ES) m/z = 407.0 (M + H)+, 1H NMR (CD3OD, 400 MHz) δ 8.00 (s, 1H), 7.78 (m, 1H), 7.59 (m, 3H), 6.50 (s, 1H), 6.32 (m, 1H), 4.10 (m, 2H), 2.89 (s, 3H), 1.37 (s, 3H) |
| 13 | 2-({5-Chloro-2-[(1-ethyl-3-methyl-1H-pyrazol-5-yl)amino]-4-pyridinyl}amino)-N-methylbenzamide | | | LCMS (ES) m/z = 384.8(M + H); 1H NMR (400 MHz, METHANOL-d4) δ ppm 8.01 (s, 1H), 7.76-7.74 (m, 1H), 7.62-7.61 (m, 2H), 7.41-7.37 (m, 2H), 6.59 (s, 1H), 6.20 (s, 1H), 4.07-4.01 (m, 2H), 2.91 (s, 3H), 2.27 (s, 3H), 1.35(tr, J = 7.2 Hz, 3H). |
| 14 | 2-[(5-Chloro-2-{[3-(1,1-dimethylethyl)-1-methyl-1H-pyrazol-5-yl]amino}-4-pyridinyl)amino]-N-methylbenzamide | | | LCMS (ES) m/z = 412.8(M + H); 1H NMR (400 MHz, METHANOL-d4) δ ppm 8.05 (s, 1H), 7.75-7.72 (m, 1H), 7.60-7.58 (m, 2H), 7.40-7.35 (m, 1H), 6.52 (s, 1H), 6.27 (s, 1H), 3.70 (s, 3H), 2.91 (s, 3H), 1.30 (s, 9H). |

TABLE 1-continued

| Ex. | Name | $R_a$ | $R_b$ | Data |
|---|---|---|---|---|
| 15 | 2-[(5-Chloro-2-{[1-ethyl-3-(hydroxymethyl)-1H-pyrazol-5-yl]amino}-4-pyridinyl)amino]-N-methylbenzamide | 1-ethyl-3-(hydroxymethyl)-1H-pyrazol-5-yl | 2-(methylcarbamoyl)phenyl | LCMS (ES) m/z = 401.1(M + H); 1H NMR (400 MHz, METHANOL-d4) δ ppm 7.99 (s, 1H), 7.75-7.73 (m, 1H), 7.61-7.59 (m, 2H), 7.39-7.35 (m, 1H), 6.58 (s, 1H), 6.31 (s, 1H), 4.56 (s, 2H), 4.08-4.03 (m, 2H), 2.91 (s, 3H), 1.36(tr, J = 7.2 Hz, 6H). |
| 16 | 2-[(5-Chloro-2-{[1-(2-hydroxyethyl)-3-methyl-1H-pyrazol-5-yl]amino}-4-pyridinyl)amino]-N-methylbenzamide | 1-(2-hydroxyethyl)-3-methyl-1H-pyrazol-5-yl | 2-(methylcarbamoyl)phenyl | LCMS (ES) m/z = 401.1(M + H); 1H NMR (400 MHz, METHANOL-d4) δ ppm 8.07 (s, 1H), 7.78-7.76 (m, 1H), 7.65-7.63 (m, 2H), 7.43-7.39 (m, 1H), 6.69 (s, 1H), 6.31 (s, 1H), 4.18 (tr, J = 5.2 Hz, 2H), 3.85 (tr, J = 5.2 Hz, 2H), 2.91 (s, 3H), 2.32 (s, 3H). |
| 17 | Ethyl 5-{[5-chloro-4-({2-[(methylamino)carbonyl]phenyl}amino)-2-pyridinyl]amino}-1-ethyl-1H-pyrazole-3-carboxylate | ethyl 1-ethyl-1H-pyrazole-3-carboxylate-5-yl | 2-(methylcarbamoyl)phenyl | LCMS (ES) m/z = 443.1(M + H); 1H NMR (400 MHz, METHANOL-d4) δ ppm 8.02 (s, 1H), 7.75-7.74 (m, 1H), 7.62-7.60 (m, 2H), 7.40-7.36 (m, 1H), 6.82 (s, 1H), 6.59 (s, 1H), 4.41-4.36 (m, 2H), 4.19-4.14 (m, 2H), 2.91 (s, 3H), 1.43-1.37(m, 6H). |
| 18 | 5-{[5-Chloro-4-({2-[(methylamino)carbonyl]phenyl}amino)-2-pyridinyl]amino}-1-ethyl-1H-pyrazole-3-carboxylic acid | 1-ethyl-1H-pyrazole-3-carboxylic acid-5-yl | 2-(methylcarbamoyl)phenyl | LCMS (ES) m/z = 415.1(M + H); 1H NMR (400 MHz, METHANOL-d4) δ ppm 8.02 (s, 1H), 7.78-7.76 (m, 1H), 7.65-7.63 (m, 2H), 7.44-7.40 (m, 1H), 6.83 (s, 1H), 6.59 (s, 1H), 4.20-4.14 (m, 2H), 2.91 (s, 3H), 1.42(tr, J = 6.8 Hz, 3H). |
| 19 | 5-{[5-Chloro-4-({2-[(methylamino)carbonyl]phenyl}amino)-2-pyridinyl]amino}-1-ethyl-N-(methyloxy)-1H-pyrazole-3-carboxamide | 1-ethyl-N-methoxy-1H-pyrazole-3-carboxamide-5-yl | 2-(methylcarbamoyl)phenyl | LCMS (ES) m/z = 444.1(M + H); 1H NMR (400 MHz, METHANOL-d4) δ ppm 8.01 (s, 1H), 7.76-7.74 (m, 1H), 7.63-7.62 (m, 2H), 7.41-7.37 (m, 1H), 6.74 (s, 1H), 6.57 (s, 1H), 4.16-4.13 (m, 2H), 3.81 (s, 3H), 2.91 (s, 3H), 1.42(tr, J = 6.8 Hz, 3H). |
| 20 | 5-{[5-Chloro-4-({2-[(methylamino)carbonyl]phenyl}amino)-2-pyridinyl]amino}-1-ethyl-N-methyl-1H-pyrazole-3-carboxamide | 1-ethyl-N-methyl-1H-pyrazole-3-carboxamide-5-yl | 2-(methylcarbamoyl)phenyl | LCMS (ES) m/z = 428.1(M + H); 1H NMR (400 MHz, METHANOL-d4) δ ppm 8.01 (s, 1H), 7.76-7.74 (m, 1H), 7.62-7.61 (m, 2H), 7.41-7.38 (m, 1H), 6.71 (s, 1H), 6.55 (s, 1H), 4.16-4.10 (q, J = 7.2 Hz, 2H), 2.92 (s, 3H), 2.91 (s, 3H), 1.42(tr, J = 7.2 Hz, 3H). |

TABLE 1-continued

| Ex. | Name | $R_a$ | $R_b$ | Data |
|---|---|---|---|---|
| 21 | 2-[(5-Chloro-2-{[3-methyl-1-(2,2,2-trifluoroethyl)-1H-pyrazol-5-yl]amino}-4-pyridinyl)amino]-N-methylbenzamide | | | LCMS (ES) m/z = 439.1(M + H); 1H NMR (400 MHz, METHANOL-d4) δ ppm 8.00 (s, 1H), 7.76-7.74 (m, 1H), 7.62-7.58 (m, 2H), 7.40-7.36 (m, 1H), 6.61 (s, 1H), 6.25 (s, 1H), 4.82-4.76 (q, J = 8.4 Hz, 2H), 2.91 (s, 3H), 2.27(s, 3H). |
| 22 | 2-[(5-Chloro-2-{[1-(1-methyl-4-piperidinyl)-1H-pyrazol-5-yl]amino}-4-pyridinyl)amino]-N-methylbenzamide | | | LCMS (ES) m/z = 440.1(M + H); 1H NMR (400 MHz, METHANOL-d4) δ ppm 8.04 (s, 1H), 7.75-7.73 (m, 1H), 7.61-7.57 (m, 3H), 7.42-7.38 (m, 1H), 6.45 (s, 1H), 6.33 (s, 1H), 4.60-4.50 (m, 1H), 3.67-3.63 (m, 2H), 3.25-3.15 (m, 2H), 2.91 (s, 3H), 2.90 (s, 3H), 2.40-2.12 (m, 4H). |
| 23 | 2-{[5-Chloro-2-({1-[2-(dimethylamino)ethyl]-3-methyl-1H-pyrazol-5-yl}amino)-4-pyridinyl]amino}-N-methylbenzamide | | | LCMS (ES) m/z = 428.1(M + H); 1H NMR (400 MHz, METHANOL-d4) δ ppm 8.06 (s, 1H), 7.76-7.74 (m, 1H), 7.62-7.61 (m, 2H), 7.43-7.38 (m, 1H), 6.59 (s, 1H), 6.18 (s, 1H), 4.41-4.38 (t, J = 5.6 Hz, 2H), 3.63-3.60 (t, J = 5.6 Hz, 2H), 2.98 (s, 6H), 2.91 (s, 3H), 2.25 (s, 3H). |
| 24 | 5-{[5-Chloro-4-({2-[(methylamino)carbonyl]phenyl}amino)-2-pyridinyl]amino}-N-[2-(dimethylamino)ethyl]-1-ethyl-1H-pyrazole-3-carboxamide | | | LCMS (ES) m/z = 485.2(M + H); 1H NMR (400 MHz, METHANOL-d4) δ ppm 8.03 (s, 1H), 7.76-7.74 (m, 1H), 7.62-7.60 (m, 2H), 7.40-7.35 (m, 1H), 6.76 (s, 1H), 6.56 (s, 1H), 4.16-4.14 (q, J = 7.2 Hz, 2H), 3.77 (tr, J = 6.0 Hz, 2H), 3.38 (tr, J = 6.0 Hz, 2H), 2.99(s, 6H), 2.91 (s, 3H), 1.42(tr, J = 7.2 Hz, 3H). |
| 25 | 5-{[5-Chloro-4-({2-[(methylamino)carbonyl]phenyl}amino)-2-pyridinyl]amino}-N-[2-(dimethylamino)ethyl]-1-ethyl-N-methyl-1H-pyrazole-3-carboxamide | | | LCMS (ES) m/z = 499.2(M + H); 1H NMR (400 MHz, METHANOL-d4) δ 8.04 (s, 1H), 7.76-7.74 (m, 1H), 7.62-7.60 (m, 2H), 7.40-7.35 (m, 1H), 6.70 (s, 1H), 6.52 (s, 1H), 4.16-4.10 (m, 2H), 3.95-3.90 (m, 1H), 3.58-3.40 (m, 5H), 3.20-3.15 (m, 1H), 3.03 (s, 6H), 2.91 (s, 3H), 1.42(tr, J = 7.2 Hz, 3H). |

TABLE 1-continued

| Ex. | Name | $R_a$ | $R_b$ | Data |
|---|---|---|---|---|
| 26 | 2-({5-Chloro-2-[(1,3-dimethyl-1H-pyrazol-4-yl)amino]-4-pyridinyl}amino)-N-methylbenzamide | 1,3-dimethyl-1H-pyrazol-4-yl | N-methylbenzamide | LC-MS (ES) m/z = 371.1 (M + H)+; $^1$H NMR (CD$_3$OD, 400 MHz) δ 7.88 (s, 1H), 7.84 (s, 1H), 7.75 (m, 1H), 7.64 (m, 2H), 7.40 (m, 1H), 6.58 (s, 1H), 3.92 (s, 3H), 2.92 (s, 3H), 2.18 (s, 3H) |
| 27 | 2-({5-Chloro-2-[(1,3-dimethyl-1H-pyrazol-4-yl)amino]-4-pyridinyl}amino)-N-methylbenzamide | 3-trifluoromethyl-1-methyl-1H-pyrazol-4-yl | N-methylbenzamide | LC-MS (ES) m/z = 425.0 (M + H)+, $^1$H NMR (CD$_3$OD, 400 MHz) δ 7.98 (s, 1H), 7.90 (s, 1H), 7.76 (m, 1H), 7.63 (m, 2H), 7.40 (m, 1H), 6.58 (s, 1H), 4.00 (s, 3H), 2.91 (s, 3H) |

The 2-{[5-trifluoromethyl-2-(aminopyrazole)-4-pyridinyl]amino}-benzamide compounds illustrated in Table 2 were prepared from 2-[(2-chloro-5-trifluoromethyl-4-pyridinyl)amino]-methylbenzamide and the corresponding amino-pyrazole substantially according to the procedure of Example 2.

TABLE 2

| Ex. | Name | Pyr | Data |
|---|---|---|---|
| 28 | 2-{[2-[(1,3-Dimethyl-1H-pyrazol-5-yl)amino]-5-(trifluoromethyl)-4-pyridinyl]amino}-N-methylbenzamide | 1,3-dimethyl-1H-pyrazol-5-yl | LC-MS (ES) m/z = 405.1 (M + H)+ |
| 29 | 2-{[2-[(1-Ethyl-1H-pyrazol-5-yl)amino]-5-(trifluoromethyl)-4-pyridinyl]amino}-N-methylbenzamide | 1-ethyl-1H-pyrazol-5-yl | LC-MS (ES) m/z = 405.1 (M + H)+ |
| 30 | N-Methyl-2-{[2-{[3-methyl-1-(1-methylethyl)-1H-pyrazol-5-yl]amino}-5-(trifluoromethyl)-4-pyridinyl]amino}benzamide | 3-methyl-1-isopropyl-1H-pyrazol-5-yl | LC-MS (ES) m/z = 433.2 (M + H)+ |
| 31 | 2-{[2-({1-[2-(Dimethylamino)ethyl]-3-methyl-1H-pyrazol-5-yl}amino)-5-(trifluoromethyl)-4-pyridinyl]amino}-N-methylbenzamide | 1-[2-(dimethylamino)ethyl]-3-methyl-1H-pyrazol-5-yl | LC-MS (ES) m/z = 462.2 (M + H)+ |
| 32 | 2-{[2-[(1-Ethyl-3-methyl-1H-pyrazol-5-yl)amino]-5-(trifluoromethyl)-4-pyridinyl]amino}-N-methylbenzamide | 1-ethyl-3-methyl-1H-pyrazol-5-yl | LCMS (ES) m/z = 419.2 (M + H) |
| 33 | N-Methyl-2-{[2-[(3-methyl-1-phenyl-1H-pyrazol-5-yl)amino]-5-(trifluoromethyl)-4-pyridinyl]amino}benzamide | 3-methyl-1-phenyl-1H-pyrazol-5-yl | LCMS (ES) m/z = 467.1 (M + H) |

TABLE 2-continued

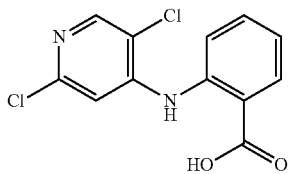 [SMILES: O=C(O)c1ccccc1Nc1cc(Cl)ncc1Cl]

| Ex. | Name | Pyr | Data |
|---|---|---|---|
| 34 | 2-{[2-{[1-(2-hydroxyethyl)-3-methyl-1H-pyrazol-5-yl]amino}-5-(trifluoromethyl)-4-pyridinyl]amino}-N-methylbenzamide | 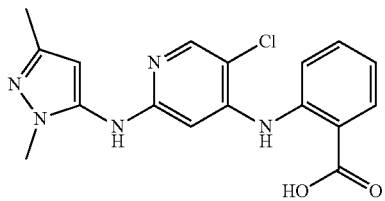 | LCMS (ES) m/z = 435.1(M + H) |

Intermediate 1

2-[(2,5-Dichloro-4-pyridinyl)amino]benzoic acid

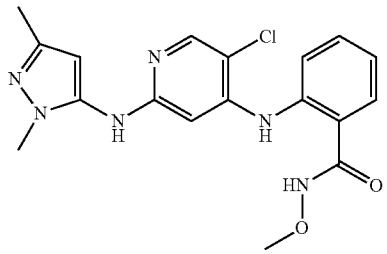 [SMILES: CONC(=O)c1ccccc1Nc1cc(Nc2cc(C)nn2C)ncc1Cl]

A mixture of 2,5-dichloro-4-iodopyridine (10 g, 36.5 mmol), 2-aminobenzoic acid (4.85 g, 35.4 mmol), DPEPhos [bis(2-diphenylphosphinophenyl)ether] (1.6 g, 2.97 mmol), palladium(II) acetate (160 mg, 0.713 mmol) and $K_3PO_4$ (20 g, 94 mmol) was degassed and heated at 120° C. (oil bath temp) for 20 h. After 20 h, LCMS showed there was 33% (relative to the desired product) starting material left. Added another 160 mg of $Pd(OAc)_2$ to the mixture, and heated to 120° C. for another 24 h. LCMS showed conversion complete. The mixture was cooled to room temperature, followed by filtration, and washing with EtOAc. The solids were acidified to pH=7-8, followed by filtration. However, the mixture was a paste, and collected solids could not be dried completely. The solids (11 g) was acidified with 6N HCl to pH=1. The resulting paste was filtered, and washed with water and TBME. The solid was dried under vacuum over $P_2O_5$ for 2 days to give the title compound (7.32 g, 60.2% yield). MS: $M(C_{12}H_8Cl_2N_2O_2)=283.11$, $(M+H)^+=283.8$; 1H NMR (400 MHz, DMSO) ppm 13.6 (s, 1 H) 10.2 (s, 1 H) 8.3 (s, 1 H) 8.0 (d, 1 H) 7.6 (q, 2 H) 7.3 (s, 1 H) 7.2 (m, 1 H).

Example 35

2-({5-Chloro-2-[(1,3-dimethyl-1H-pyrazol-5-yl)amino]-4-pyridinyl}amino)benzoic acid A pressure tube was charged with 2-[(2,5-dichloro-4-pyridinyl)amino]benzoic acid (1.0 g, 3.53 mmol), 1,3-dimethyl-1H-pyrazol-5-amine(0.589 g, 5.30 mmol), (±)-2,2'-Bis(diphenylphosphino)-1,1'-binaphthalene (0.330 g, 0.530 mmol), tris(dibenzylideneacetone)dipalladium(0) ($Pd_2(dba)_3$, 0.162 g, 0.177 mmol) and sodium tert-butoxide (0.849 g, 8.83 mmol) in 1,4-dioxane (30 mL). The tube was degassed with $N_2$ and sealed and the reaction mixture was heated in an oil bath at 120° C. for 18 hours. The reaction mixture was evaporated to dryness under high vacuum. The residue was taken back in water solution and the pH was adjusted to ~4 to 5 using 6.0 N hydrochloride acid. The reaction was concentrated to dryness and the resulting solid was dissolved in MeOH and purified by reverse-phase HPLC to give the title compound as a solid (285 mg, 21% yield). MS: $M(C_{17}H_{16}ClN_5O_2)=357.79$, $(M+H)^+=358, 360$.

Example 36

2-({5-Chloro-2-[(1,3-dimethyl-1H-pyrazol-5-yl)amino]-4-pyridinyl}amino)-N-(methyloxy)benzamide A vessel was charged with 3-({5-chloro-2-[(1,3-dimethyl-1H-pyrazol-5-yl)amino]-4-pyridinyl}amino)benzoic acid (100 mg, 0.279 mmol), 1-(3-dimethylaminopropyl)-3-ethylcarbodiimide hydrochloride (53.6 mg, 0.279 mmol) and hydroxybenzotriazole (42.8 mg, 0.279 mmol) in N,N-dimethylformamide (DMF, 1.0 mL) and the contents were stirred at room temperature for 30 min. Methoxylamine hydrochloride (23.34 mg, 0.279 mmol) was added to this mixture and stirring continued for another 10 min. The reaction mixture was cooled to 0° C. Diisopropylethylamine (DIEA, 0.098 mL, 0.559 mmol) was added and the reaction mixture was stirred at room temperature overnight. The final crude material was purified using reverse-phase HPLC, (Gilson) eluted with $CH_3CN/H_2O$ with 0.1% formic acid to yield 15 mg (18% yield) MS: $M(C_{18}H_{19}ClN_6O_2)=386.84$, $(M+H)^+=387$; 1H NMR (400 MHz, MeOD) ppm 8.16 (s, 1 H) 7.93 (s, 1 H) 7.50-7.66 (m, 2 H) 7.11-7.25 (m, 1 H) 6.62 (s, 1 H) 5.99 (s, 1 H) 3.80 (s, 3 H) 3.55-3.70 (s, 3 H) 2.11-2.26 (s, 3 H).

The 2-({5-chloro-2-[(1,3-dimethyl-1H-pyrazol-5-yl)amino]-4-pyridinyl}amino)-N-alkyl-N-(alkylyloxy)benzamide compounds illustrated in Table 3 were prepared from 3-({5-chloro-2-[(1,3-dimethyl-1H-pyrazol-5-yl)amino]-4-pyridinyl}amino)benzoic acid and amino-alcohols substantially according to the procedure of Example 36.

TABLE 3

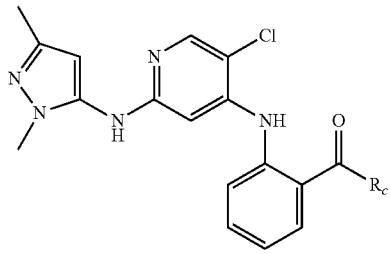

| Ex. | Name | R_c | Data |
|---|---|---|---|
| 37 | 2-({5-chloro-2-[(1,3-dimethyl-1H-pyrazol-5-yl) amino]-4-pyridinyl} amino)-N-methyl-N-(methyloxy)benzamide | *...N(CH3)OCH3 | LC-MS (ES) m/z = 387 (M + H)+; 1H NMR (400 MHz, MeOD) ppm 8.16 (s, 1 H) 7.93 (s, 1 H) 7.50-7.66 (m, 2 H) 7.11-7.25 (m, 1 H) 6.62(s, 1 H) 5.99 (s, 1 H) 3.80 (s, 3 H) 3.55-3.70 (s, 3 H) 2.11-2.26 (s, 3 H) |
| 38 | 2-({5-Chloro-2-[(1,3-dimethyl-1H-pyrazol-5-yl)amino]-4-pyridinyl}amino)-N-{[2-(dimethylamino)ethyl]oxy}benzamide | *...N(H)OCH2CH2N(CH3)2 | LC-MS (ES) m/z = 444, 446 (M + H)+; 1H NMR (400 MHz, MeOD) δ ppm 8.50 (s, 1 H) 7.93 (s, 1 H) 7.64-7.71 (m, 1 H) 7.51-7.61 (m, 2 H) 7.21(ddd, J = 8.0, 6.2, 2.3 Hz, 1 H) 6.58 (s, 1 H) 5.98 (s, 1 H) 4.22-4.31 (m, 2 H) 3.61 (s, 3 H) 3.33- -3.40 (m, 2H) 2.96 (s, 6H) 2.19 (s, 3H) |

Example 39

2-({5-Chloro-2-[(1-ethyl-3-methyl-1H-pyrazol-5-yl)amino]-4-pyridinyl}amino)-N-(methyloxy)benzamide

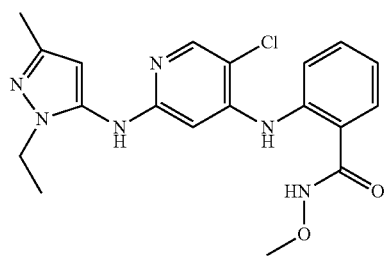 [SMILES: CCn1nc(C)cc1Nc1cc(Nc2ccccc2C(=O)NOC)c(Cl)cn1]

39a) 2-[(2,5-Dichloro-4-pyridinyl)amino]-N-(methyloxy)benzamide

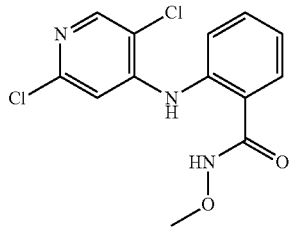

A vessel was charged with 3-[(2,5-dichloro-4-pyridinyl)amino]benzoic acid (1.0 g, 3.53 mmol), 1-(3-dimethylaminopropyl)-3-ethylcarbodiimide hydrochloride (677 mg, 3.53 mmol) and hydroxybenzotriazole (HOBT) (541 mg, 3.53 mmol) in N,N-dimethylformamide (DMF, 7.0 mL) and was stirred at room temperature for 30 min. To this solution methoxylamine hydrochloride (0.3 g, 3.53 mmol) was added and reaction mixture was stirred for another 10 min. The reaction mixture was cooled to 0° C. by using an ice bath. To this reaction mixture diisopropylethylamine (1.2 mL, 7.06 mmol) was added and the mixture was stirred at room temperature overnight. After concentrating under vacuum, the residue was worked up by using a saturated aqueous solution of NaHCO$_3$ and CH$_2$Cl$_2$. The organic phase was washed with brine then dried over MgSO$_4$ and filtered. The CH$_2$Cl$_2$ was removed by rotary evaporation. The crude material was loaded on silica gel column and eluted by MeOH in CH$_2$Cl$_2$ with NH$_4$OH 0.1%, which gave the desired product 2-[(2,5-dichloro-4-pyridinyl)amino]-N-(methyloxy)benzamide (850 mg, 2.72 mmol, 77% yield) MS: M(C$_{13}$H$_{11}$C$_{12}$N$_3$O$_2$)=312.15, (M+H)+=312, 314; 1H NMR (400 MHz, CHLOROFORM-d) δ ppm 9.57 (br. s., 1 H) 8.72 (s, 1 H) 8.22 (s, 1 H) 7.51-7.67 (m, 3 H) 7.25 (s, 1 H) 7.07-7.21 (m, 1 H) 3.92 (s, 3 H).

39b) 2-({5-Chloro-2-[(1-ethyl-3-methyl-1H-pyrazol-5-yl)amino]-4-pyridinyl}amino)-N-(methyloxy)benzamide A 20-mL microwave tube was charged with 2-[(2,5-dichloro-4-pyridinyl)amino]-N-(methyloxy)benzamide (100 mg, 0.320 mmol), 1-ethyl-3-methyl-1H-pyrazol-5-amine (60.1 mg, 0.481 mmol), cesium carbonate (313 mg, 0.961 mmol), 1,4-dioxane (5.0 mL) and THF (1.0 mL). The reaction mixture was degassed by nitrogen for 10 min. (±)-2,2'-Bis(diphenylphosphino)-1,1'-binaphthalene (19.95 mg, 0.032 mmol) and Palladium(II) acetate (3.60 mg, 0.016 mmol) in minimum amount of 1,4-dioxane were then added. The tube was sealed and reaction mixture was heated in microwave oven 160° C. for 40 min. The resulting suspension was cooled to room temperature and filtered through celite. The filtrate was evaporated to dryness and the crude reaction mixture was purified by reverse-phase HPLC to give the title compound as a solid (16 mg, 24% yield) MS: M(C$_{19}$H$_{21}$ClN$_6$O$_2$)=400.86, (M+H)+=401; 1H NMR (400 MHz, MeOD) δ ppm 7.92 (s, 1 H) 7.44-7.66 (m, 3 H) 7.11-7.25 (m, 1 H) 6.61 (s, 1 H) 5.99 (s, 1 H) 3.98 (q, J=7.3 Hz, 2 H) 3.80 (s, 3 H) 2.21 (s, 3 H) 1.32 (t, J=7.2 Hz, 3 H).

The 2-({5-chloro-2-(pyrazol-5-yl)amino]-4-pyridinyl}amino)-N-(methyloxy)benzamide compounds illustrated in Table 4 were prepared from 2-[(2,5-dichloro- 4-pyridinyl)amino]-N-(methyloxy)benzamide and aminopyrazoles substantially according to the procedure of Example 39.

TABLE 4

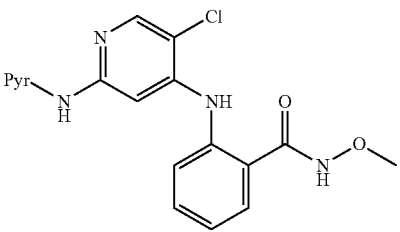

| Ex | Name | Pyr | Data |
|----|------|-----|------|
| 40 | 2-({5-Chloro-2-[(1-ethyl-1H-pyrazol-5-yl)amino]-4-pyridinyl}amino)-N-(methyloxy)benzamide | 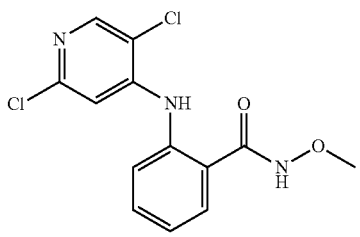 | LC-MS (ES) m/z = 387, 388 (M + H)+; 1H NMR (400 MHz, MeOD) δ ppm 1H 7.90-7.96 (m, 1 H) 7.49-7.66 (m, 3 H) 7.45 (t, J = 2.2 Hz, 1 H) 7.10-7.22 (m, 1 H) 6.61 (s, 1 H) 6.19 (d, J = 1.8 Hz, 1 H) 4.06 (q, J = 7.1 Hz, 2 H) 3.80 (s, 3 H) 1.35 (t, J = 7.2 Hz, 3H) |

Intermediate 2

2-[(2,5-Dichloro-4-pyridinyl)amino]-N-(methyloxy)benzamide

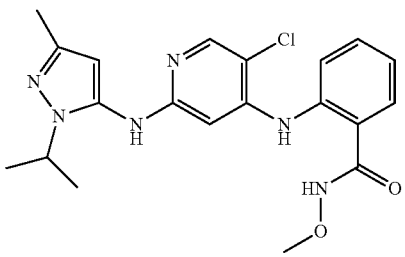 [SMILES: CONC(=O)c1ccccc1Nc1cc(Nc2cc(C)nn2C(C)C)ncc1Cl]

A solution of 3-[(2,5-dichloro-4-pyridinyl)amino]benzoic acid (500 mg, 1.766 mmol), N-(3-dimethylaminopropyl)-N'-ethylcarbodiimide (EDC) (339 mg, 1.766 mmol) and 1-hydroxybenzotriazole (HOBT) (270 mg, 1.766 mmol) in N,N-dimethylformamide (3532 µl) was stirred at room temperature for 30 min. To this solution O-methylhydroxylamine(aminoxy)methane (148 mg, 1.766 mmol) was then added and stirred for another 10 min. The reaction mixture was cooled using an ice water bath. Then diisopropylethylamine (617 µl, 3.53 mmol) was added. After the addition was finished, the reaction mixture was stirred at room temperature overnight. The reaction mixture was followed by HPLC and LCMS. The final crude material was worked up by addition of saturated aqueous NaHCO$_3$ and CH$_2$Cl$_2$. Organic phase was washed with brine then dried over MgSO$_4$. The solution was filtered and solvent was removed by evaporation. The oil like crude material was loaded on silica column and eluted with MeOH in CH$_2$Cl$_2$ with NH$_4$OH 0.1% to give the target compound 2-[(2,5-dichloro-4-pyridinyl)amino]-N-(methyloxy)benzamide (320 mg, 1.025 mmol, 58.0% yield) as a yellow solid; MS; M(C$_{13}$H$_{11}$Cl$_2$N$_3$O$_2$)=312.15, (M+H)+=312, 313.9; 1H NMR (400 MHz, CHLOROFORM-d) ppm 9.66 (br. s., 1 H) 9.60 (br. s., 1 H) 8.20 (s, 1 H) 7.49-7.61 (m, 3 H) 7.24 (s, 1 H) 7.09-7.16 (m, 1 H) 3.90 (s, 3 H).

Example 41a

2-[(5-Chloro-2-{[3-methyl-1-(1-methylethyl)-1H-pyrazol-5-yl]amino}-4-pyridinyl)amino]-N-(methyloxy)benzamide

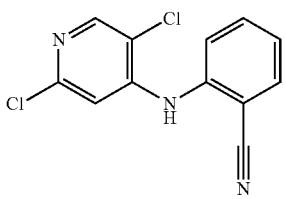 [SMILES: N#Cc1ccccc1Nc1cc(Cl)ncc1Cl]

A microwave tube was charged with 2-[(2,5-dichloro-4-pyridinyl)amino]-N-(methyloxy)benzamide (70 mg, 0.224 mmol), {3-methyl-1-(1-methylethyl)-1H-pyrazol-5-amine (70 mg, 0.503 mmol) and cesium carbonate (230 mg, 0.706 mmol). The reaction mixture was degassed with nitrogen for 10 min. At same time, BINAP (50 mg, 0.080 mmol) and palladium(II) acetate (10 mg, 0.045 mmol) were added. The reaction mixture was heated in a microwave at 160° C. for 40 min. The crude material was purified on reverse-phase HPLC (Gilson) eluting with CH$_3$CN/H$_2$O with 0.1% formic acid which gave a title compound (15 mg, 15%); MS: M(C$_{20}$H$_{23}$ClN$_6$O$_2$)=414.89, (M+H)+=415, 416; 1H NMR (400 MHz, CHLOROFORM-d) δ ppm 9.42 (br. s., 1 H) 8.71 (br. s., 1 H) 8.02 (s, 1 H) 7.54 (br. s., 1 H) 7.06 (t, J=7.5 Hz, 1 H) 6.48 (s, 1 H) 6.32 (br. s., 1 H) 5.86 (s, 1 H) 4.47 (dt, J=13.4, 6.7 Hz, 1 H) 3.92 (s, 3 H) 2.26 (s, 3 H) 1.41-1.43 (d, J=6.6 Hz, 2 H).

Intermediate 3

2-[(2,5-Dichloro-4-pyridinyl)amino]benzonitrile

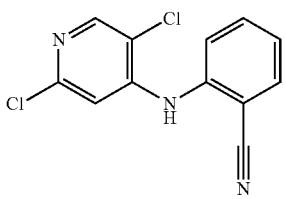 [SMILES: N#Cc1ccccc1Nc1cc(Cl)ncc1Cl]

The solution of 2,5-dichloro-4-iodopyridine (100 g, 365 mmol), 2-aminobenzonitrile (43.1 g, 365 mmol) and potassium triphosphate (233 g, 1095 mmol) in 1,4-dioxane (2.5 L) was degassed by N$_2$ stream. To this solution was added DPEPhos (15.73 g, 29.2 mmol) and palladium acetate (3.28 g, 14.60 mmol). The reaction mixture was stirred at reflux for 18 hour. The solution was filtered through 0.5 in. celite and 0.2 inch of silica. The solution was evaporated. Solid was suspended in the diethyl ether and filtered. Diethyl ether was concentrated, and the resulting solid was filtered. 2-[(2,5-Dichloro-4-pyridinyl)amino]benzonitrile (80 g, 288 mmol, 79% yield) was isolated as an orange solid. 1H NMR (400 MHz, DMSO-d$_6$) ppm 6.49 (s, 1 H) 7.50 (td, J=7.58, 1.01 Hz, 1 H) 7.56 (d, J=7.58 Hz, 1 H) 7.80 (td, J=7.83, 1.77 Hz, 1 H) 7.95 (dd, J=7.83, 1.52 Hz, 1 H) 8.26 (s, 1 H) 9.05 (brs, 1 H); HPLC Rt=2.88 min, MS (ESI): 263.9, 265.9 [M+H]$^+$.

Intermediate 4

2-[(5-Chloro-2-{[3-methyl-1-(1-methylethyl)-1H-pyrazol-5-yl]amino}-4-pyridinyl)amino]benzonitrile

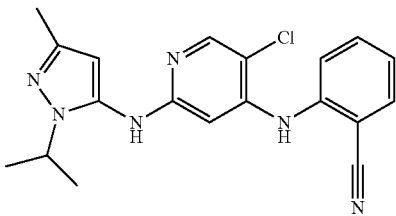 [SMILES: Cc1cc(Nc2cc(Nc3ccccc3C#N)c(Cl)cn2)n(C(C)C)n1]

The solution of 2-[(2,5-dichloro-4-pyridinyl)amino]benzonitrile (110 g, 396 mmol), 3-methyl-1-(1-methylethyl)-1H-pyrazol-5-amine (55.1 g, 396 mmol), and cesium carbonate (387 g, 1187 mmol) in 1,4-dioxane (2.5 L) was degassed by N$_2$ stream, and 2,2'-bis(diphenylphosphino)-1,1'-binaphthyl (BINAP) (19.71 g, 31.7 mmol) followed by palladium acetate (3.55 g, 15.83 mmol) were added. The reaction mixture was heated to reflux for overnight under N$_2$. The reaction mixture was filtered and the liquid was concentrated. Ethyl acetate (1500 mL), followed by 1 M HCl (1000 mL) were added. Layers were separated. Ethyl acetate was washed with 1 M HCl until no product was observed by HPLC (1000 mL total, 1×). HCl phases were combined, and backwashed with ethyl acetate (3×1000 mL), until the product peak was relativity pure in the HCL layer. The HCl layer was then basified with NaOH (50 w/w followed by 1 M) to ph~4 resulting in a cloudy solution. Ethyl acetate (2000 mL) was added and layers were separated. The ethyl acetate was washed with brine and evaporated. After neutralization—after addition of ethyl acetate—the reaction mixture was filtered to get some product. Also isolation of product during evaporation can be done by filtration of white solid, which comes from the mother liquor. All solids and evaporated products were combined. 2-[(5-Chloro-2-{[3-methyl-1-(1-methylethyl)-1H-pyrazol-5-yl]amino}-4-pyridinyl)amino]benzonitrile (80 g, 207 mmol, 52.4% yield) was isolated as a yellow solid. 1H NMR (400 MHz, DMSO-d$_6$) ppm 1.24 (d, J=6.57 Hz, 6 H) 2.08 (s, 3 H) 4.34 (quin, J=6.57 Hz, 1 H) 5.87 (s, 1 H) 5.97 (s, 1 H) 7.41 (td, J=7.58, 1.01 Hz, 1 H) 7.47 (d, J=8.08 Hz, 1 H) 7.75 (td, J=7.83, 1.52 Hz, 1 H) 7.90 (dd, J=7.83, 1.52 Hz, 1 H) 7.94 (s, 1 H) 8.42 (d, J=17.43 Hz, 2 H); HPLC Rt=2.36 min, MS (ESI): [M+H]$^+$=367.1, 368.1.

Intermediate 5

2-[(5-Chloro-2-{[3-methyl-1-(1-methylethyl)-1H-pyrazol-5-yl]amino}-4-pyridinyl)amino]benzoic acid

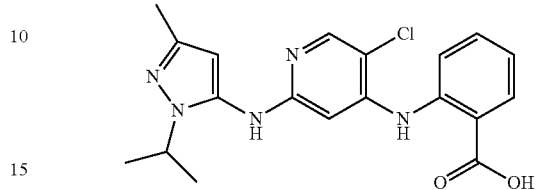

2-[(5-Chloro-2-{[3-methyl-1-(1-methylethyl)-1H-pyrazol-5-yl]amino}-4-pyridinyl)amino]benzonitrile (80 g, 218 mmol) was dissolved in 1,4-dioxane (1.5 L) and 1 M NaOH (1500 mL, 1500 mmol) was added. The suspension was refluxed overnight. After cooling to RT, ethyl acetate (1 L) was added and layers were separated. The water layer was washed with 1 L of ethyl acetate. Both organic layers were combined and backwashed with 0.1 M NaOH (1 L) until no product was observed in organic. The organics were then discarded. Combined aqueous were then washed with 1 L of ethyl acetate. The water layer was then acidified with acetic acid (very slowly to ph~7). The solid was filtered and 2-[(5-chloro-2-{[3-methyl-1-(1-methylethyl)-1H-pyrazol-5-yl]amino}-4-pyridinyl)amino]benzoic acid (67 g, 165 mmol, 76% yield) was isolated as a yellow solid. 1H NMR (400 MHz, DMSO-d$_6$) ppm 1.28 (d, J=6.57 Hz, 6 H) 2.11 (s, 3 H) 4.41 (quin, J=6.57 Hz, 1 H) 5.96 (s, 1 H) 6.83 (s, 1 H) 7.09 (ddd, J=8.02, 5.12, 3.03 Hz, 1 H) 7.40 (1 H) 7.52-7.61 (m, 2 H) 7.91-8.16 (m, 2 H) 8.55 (s, 1 H) 10.17 (brs, 1 H) 13.64 (brs, 1 H); HPLC Rt=2.35 min, MS (ESI): [M+H]$^+$= 386.1.

Example 41b

2-[(5-Chloro-2-{[3-methyl-1-(1-methylethyl)-1H-pyrazol-5-yl]amino}-4-pyridinyl)amino]-N-(methyloxy)benzamide

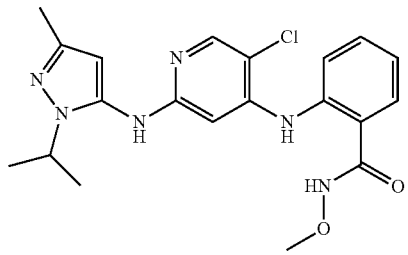 [SMILES: CONC(=O)c1ccccc1Nc1cc(Nc2cc(C)nn2C(C)C)ncc1Cl]

To a solution of 2-[(5-chloro-2-{[3-methyl-1-(1-methylethyl)-1H-pyrazol-5-yl]amino}-4-pyridinyl)amino]benzoic acid (67 g, 174 mmol) and 1-hydroxybenzotriazole (29.3 g, 191 mmol) in N,N-dimethylformamide (700 mL) was added N-(3-dimethylaminopropyl)-N'-ethylcarbodiimide (36.6 g, 191 mmol) and the solution was stirred for 30 minutes. O-Methylhydroxylamine hydrochloride (15.95 g, 191 mmol) was added and the solution stirred for additional 15 minutes, the cooled down to the 0° C. and diisopropylethlyamine (91 mL, 521 mmol) was added dropwise. The reaction mixture was stirred overnight tat the room temperature. Water (4000 mL) was added and the solution was acidified with acetic acid (20 mL). The solution was extracted 2×2 L of ethyl acetate. The organic was washed with water (1 L), brine, and dried over MgSO$_4$, filtered and evaporated. 2-[(5-Chloro-2-{[3-methyl-1-(1-methylethyl)-1H-pyrazol-5-yl]amino}-4-pyridinyl)amino]-N-(methyloxy)benzamide (74 g, 164 mmol, 94% yield, 92% pure) was isolated as a yellow foam. 1H NMR (400 MHz, DMSO-d$_6$) ppm 1.27 (d, J=6.57 Hz, 6H) 2.10 (s, 3 H) 3.71 (s, 3 H) 4.39 (quin, J=6.51 Hz, 1 H) 5.93 (s, 1 H) 6.66 (s, 1 H) 7.08-7.19 (m, 1 H) 7.49-7.64 (m, 3 H) 7.98 (s, 1 H) 8.50 (s, 1 H) 9.50 (s, 1 H) 11.93 (s, 1 H).; HPLC Rt=2.13 min, MS (ESI): [M+H]$^+$=415.1.

Purification of Example 41a and 41b Products

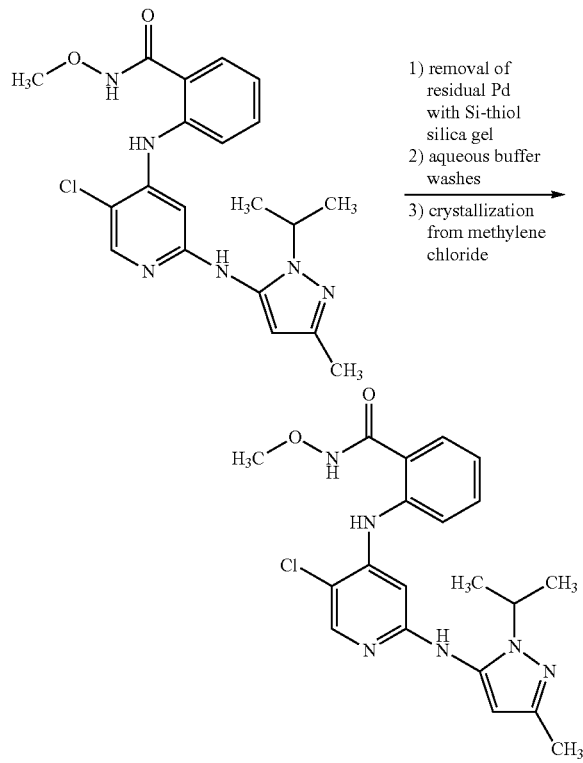

2-[(5-Chloro-2-{[3-methyl-1-(1-methylethyl)-1H-pyrazol-5-yl]amino}-4-pyridinyl)amino]-N-(methyloxy)benzamide (173.3 g, 63.5% w/w, 265.2 mmoles) was dissolved in ethyl acetate (3.50 L, 20 volumes) and heated to about 50° C. To this solution was added Si-thiol (functionalized silica gel) (87 g, 50% loading). The mixture was held at about 50° C. for 16-20 hours. It was then filtered off the Si-thiol silica gel. The filter cake was rinsed with ethyl acetate (2×200 mL each) and filtrates were combined. Then the combined filtrates were washed with 1 M aqueous ammonium formate at pH 9.4 (5×1 L each), washed with water, brine, and dried over magnesium sulfate. Dried EtOAC was filtered and stripped to dryness giving a yellow foam. It was dried at 50-55° C. for about 2 hours to a constant weight of 160 g. This material was slurried in methylene chloride (800 mL, 5 volumes), heated to reflux to afford a solution, and filtered. The solution was cooled to 20-25° C. The product crystallized upon cooling. After about 2 hours, the product was collected by filtration and rinsed with methylene chloride. The white solid was dried at 50-55° C. for 14-16 hours to a constant weight. 2-[(5-Chloro-2-{[3-methyl-1-(1-methylethyl)-1H-pyrazol-5-yl]amino}-4-pyridinyl)amino]-N-(methyloxy)benzamide (85.0 g, 204.9 mmoles, 77% overall yield) was isolated as a white solid. 1H NMR (400 MHz, DMSO-d$_6$) ppm 1.27 (d, J=6.57 Hz, 6 H) 2.10 (s, 3 H) 3.70 (s, 3 H) 4.39 (quin, J=6.57 Hz, 1 H) 5.92 (s, 1 H) 6.66 (s, 1 H) 7.02-7.24 (m, 1 H) 7.45-7.68 (m, 3 H) 7.98 (s, 1 H) 8.48 (s, 1 H) 9.49 (br. s, 1 H) 11.91 (s, 1 H). C18 HPLC RT=6.2 minutes (99.0% purity). MS (ESI): 415.0 [M+H]$^+$.

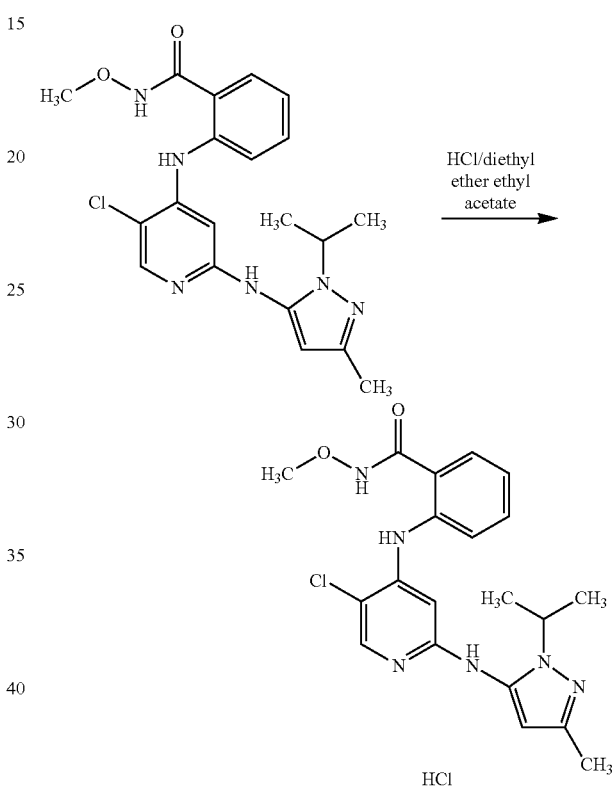

2-[(5-Chloro-2-{[3-methyl-1-(1-methylethyl)-1H-pyrazol-5-yl]amino}-4-pyridinyl)amino]-N-(methyloxy)benzamide (235.2 g total weight, 228.0 g assayed content, 549.5 mmoles) was slurried in ethyl acetate (7.1 L, 30 volumes). The mixture was heated to about 50-55° C. to afford a cloudy solution. The cloudy solution was filtered. To the filtered solution was added 2.0 M HCl in diethyl ether (210 g, 281 mL, 1.02 equiv.) over 15-20 minutes. Upon HCl addition, a white slurry was observed. It was stirred at room temperature for about 16-20 hours. Product was collected by filtration and rinsed with ethyl acetate (2×500 mL each). The wet cake was dried at 50-55° C./<5 mm Hg for 16-20 hours to a constant weight. 2-[(5-Chloro-2-{[3-methyl-1-(1-methylethyl)-1H-pyrazol-5-yl]amino}-4-pyridinyl)amino]-N-(methyloxy)benzamide, monohydrochloride, (245.9 g, 544.7 mmoles, 96% yield) was isolated as a white solid. 1H NMR (400 MHz, DMSO-d$_6$) ppm 1.32 (d, J=6.57 Hz, 6 H) 2.18 (s, 3 H) 3.70 (s, 3 H) 4.35-4.62 (m, 1 H) 6.12 (br. s, 1 H) 6.60 (br. s, 1 H) 7.19-7.41 (m, 1 H) 7.48-7.75 (m, 3 H) 8.09 (s, 1 H) 9.59-9.99 (m, 2 H) 11.98 (br. s, 1 H). C18 HPLC RT=6.1 minutes (99.6% purity). MS (ESI): 414.8 [M+H]$^+$.

Example 42

2-({5-Chloro-2-[(1-ethyl-3-methyl-1H-pyrazol-5-yl)amino]-4-pyridinyl}amino)-N-ethylbenzamide

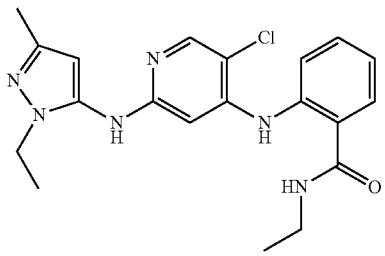 [SMILES: CCNC(=O)c1ccccc1Nc1cc(Nc2cc(C)nn2CC)ncc1Cl]

A vessel was charged with 2-[(2,5-dichloro-4-pyridinyl)amino]-N-ethylbenzamide (100 mg, 0.322 mmol), 1-ethyl-3-methyl-1H-pyrazol-5-amine (60.5 mg, 0.484 mmol), cesium carbonate (315 mg, 0.967 mmol), 1,4-dioxane (5.0 mL), and THF (1.0 mL). The reaction mixture was degassed by nitrogen for 10 min at which time (±)-2,2'-bis(diphenylphosphino)-1,1'-binaphthalene (40.1 mg, 0.064 mmol) and palladium (II) acetate (7.24 mg, 0.032 mmol) in a minimum amount of 1,4-dioxane were added. The vessel was sealed and the reaction mixture was heated in microwave oven 160° C. for 40 min. The resulting suspension was cooled to room temperature and filtered through celite. The filtrate was evaporated to dryness and the crude reaction mixture was purified by reverse-phase HPLC to give the title compound as a solid (45 mg, 30% yield); MS: $M(C_{20}H_{23}ClN_6O)$= 398.89, $(M+H)^+$=399, 401; 1H NMR (400 MHz, CHLOROFORM-d) δ ppm 8.34 (s, 1 H) 7.94 (s, 1 H) 7.66 (br. s., 1 H) 7.51 (d, J=7.8 Hz, 1 H) 7.31-7.47 (m, 2 H) 6.96-7.17 (m, 1 H) 6.58 (s, 1 H) 6.19 (t, J=5.2 Hz, 1 H) 5.86 (s, 1 H) 4.01 (q, J=7.3 Hz, 2 H) 3.42-3.62 (m, 2 H) 2.24 (s, 3 H) 1.37 (t, J=7.3 Hz, 3 H) 1.26 (t, J=7.3 Hz, 3 H).

The 2-({5-chloro-2-(1H-pyrazol-5-yl)amino]-4-pyridinyl}amino)-N-ethylbenzamide compounds illustrated in Table 5 were prepared from 2-[(2,5-dichloro-4-pyridinyl)amino]-N-ethylbenzamide and amino-pyrazoles substantially according to the procedure of Example 42.

TABLE 5

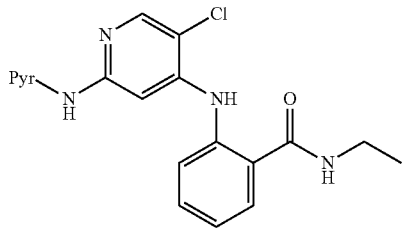

| Ex. | Name | Pyr | Data |
|---|---|---|---|
| 43 | 2-({5-Chloro-2-[(1,3-dimethyl-1H-pyrazol-5-yl)amino]-4-pyridinyl}amino)-N-ethylbenzamide | | LC-MS (ES) m/z = 385 (M + H)+; 1H NMR (400 MHz, MeOD) δ ppm 7.91 (s, 1 H) 7.67 (dd, J = 7.8, 1.52 Hz, 1 H) 7.44-7.58 (m, 2 H) 7.14-7.24 (m, 1 H) 6.61(s, 1 H) 5.98 (s, 1 H) 3.62 (s, 3 H) 3.37-3.46 (m, 2 H) 2.19 (s, 3H) 1.21 (t, J = 7.3 Hz, 3H) |
| 44 | 2-({5-Chloro-2-[(1-ethyl-1H-pyrazol-5-yl)amino]-4-pyridinyl}amino)-N-ethylbenzamide | | LC-MS (ES) m/z = 415, 416 (M + H)+; 1H NMR (400 MHz, CHLOROFORM-d) δ ppm 9.85 (s, 1 H) 8.00 (s, 1 H) 7.46-7.54 (m, 2 H) 7.33-7.44 (m, 2 H) 6.88-7.12 (m, 1 H) 6.72 (br. s., 1 H) 6.52 (s, 1 H) 5.93-6.17 (m, 2 H) 4.09 (q, J = 7.2 Hz, 2 H) 3.38-3.57 (m, 2 H) 1.34-1.49 (m, 3 H) 1.26 (t, J = 7.3 Hz, 3 H) |
| 45 | 2-[(5-Chloro-2-{[3-methyl-1-(1-methylethyl)-1H-pyrazol-5-yl]amino}-4-pyridinyl)amino]-N-ethylbenzamide | | LC-MS (ES) m/z = 413 (M + H)+; 1H NMR (400 MHz, DMSO-d6) δ ppm 10.04 (s, 1 H) 8.71 (t, J = 5.4 Hz, 1 H) 8.48 (s, 1 H) 7.97 (s, 1 H) 7.71(dd, J = 7.8, 1.26 Hz, 1 H) 7.44-7.59 (m, 2 H) 7.04-7.19 (m, 1 H) 6.69 (s, 1 H) 5.93 (s, 1 H) 4.30-4.45 (m, 1H) 3.22-3.31 (m, 2 H) 2.10 (s, 3 H) 1.29-1.36 (d, J = 8.0 Hz 6 H) 1.12 (t, J = 7.2 Hz, 3 H) |

Intermediate 6

1-Ethyl-3-[2-(1-pyrrolidinyl)ethyl]-1H-pyrazol-5-amine

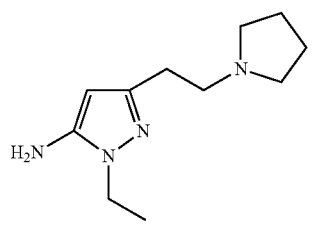

Int. 6a) N-{1-Ethyl-3-[2-oxo-2-(1-pyrrolidinyl)ethyl]-1H-pyrazol-5-yl}-2,2,2-trifluoroacetamide

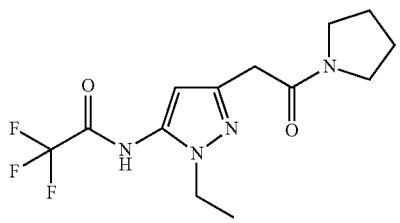 [SMILES: CCn1nc(CC(=O)N2CCCC2)cc1NC(=O)C(F)(F)F]

Pentafluorophenyl trifluoroacetate (497 mg, 1.773 mmol) was added dropwise to a stirred solution of (5-amino-1-ethyl-1H-pyrazol-3-yl) acetic acid (150 mg, 0.887 mmol) and pyridine (0.143 mL, 1.773 mmol) in DMF (3 mL). The reaction mixture was stirred for 15 min and pyrrolidine (0.220 mL, 2.66 mmol) was added. The reaction mixture was stirred at 65° C. for 40 min. The mixture was cooled and quenched with water (5 mL) and extracted with EtOAc (3×). The extract was dried over Na$_2$SO$_4$, filtered and concentrated. The residue was purified using RP-HPLC to give product (125 mg). MS: (M+H)$^+$=318.8. $^1$H NMR (400 MHz, CHLOROFORM-d) ppm 1.32 (t, J=7.2 Hz, 3H), 1.87-2.06 (m, 4H), 3.46 (t, J=6.8 Hz, 2H), 3.53 (t, J=6.8 Hz, 2H), 3.66 (s, 2H), 4.07 (q, J=7.2 Hz, 2H), 5.30 (s, 1H).

Int. 6b) 1-ethyl-3-[2-oxo-241-pyrrolidinyl)ethyl]-1H-pyrazol-5-amine

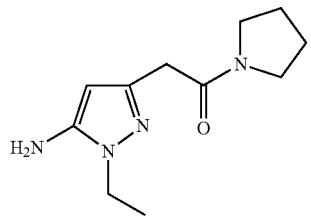 [SMILES: CCn1nc(CC(=O)N2CCCC2)cc1N]

To a solution of N-{1-ethyl-3-[2-oxo-2-(1-pyrrolidinyl)ethyl]-1H-pyrazol-5-yl}-2,2,2-trifluoroacetamide (120 mg, 0.377 mmol) in methanol (1.5 mL) was added 2M HCl (1 mL, 0.377 mmol), and the reaction mixture was stirred at 50° C. for 2 h and concentrated. The residue was neutralized using saturated NaHCO$_3$ solution and concentrated. The residue was dried under high vacuum to give 79 mg and used for next reaction without further purification. MS: (M+H)$^+$=222.8. $^1$H NMR (400 MHz, DMSO-d6) ppm 1.18 (t, J=7.2 Hz, 3H), 1.70-1.85 (m, 4 H), 3.24 (t, J=6.8 Hz, 2H), 3.31 (s, 2 H), 3.43 (t, J=6.8 Hz, 2H), 3.78 (q, J=7.2 Hz, 2H), 5.11 (s, 1H).

Int. 6c) 1-ethyl-3-[2-(1-pyrrolidinyl)ethyl]-1H-pyrazol-5-amine

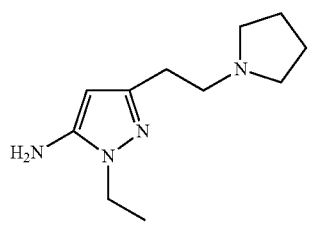

To a solution of 1-ethyl-3-[2-oxo-2-(1-pyrrolidinyl)ethyl]-1H-pyrazol-5-amine (600 mg, 1.784 mmol) in tetrahydrofuran (8 mL) cooled with water-ice bath was added a solution of 2M LAH (1.0 mL, 2.00 mmol) solution dropwise, and the reaction mixture was stirred for 5 h at rt and 30 min at 50 degree. The reaction mixture was carefully quenched with methanol followed by water and concentrated. The residue was washed with DCM/methanol 5 times. The extract was concentrated and the residue was purified using HPLC under the basic conditions to give 220 mg of product. MS: (M+H)$^+$=208.7. $^1$H NMR (400 MHz, CHLOROFORM-d) ppm 1.37 (t, J=7.2 Hz, 3H), 1.79 (m, 4H), 2.56 (m, 4H), 2.71 (m, 2H), 3.42 (m, 2H), 3.94 (q, J=7.2 Hz, 2H), 5.40 (s, 1H).

Example 46

2-{[5-Chloro-2-({1-ethyl-3-[2-(1-pyrrolidinyl)ethyl]-1H-pyrazol-5-yl}amino)-4-pyridinyl]amino}-N-methylbenzamide

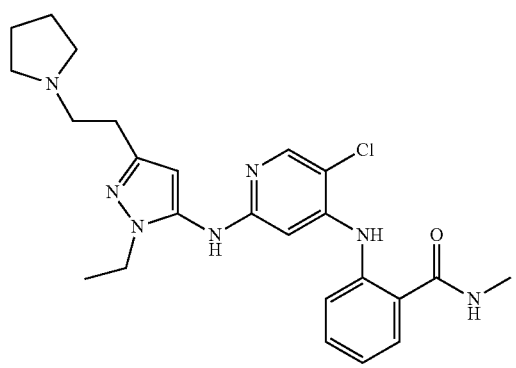 [SMILES: CCn1nc(CCN2CCCC2)cc1Nc1cc(Nc2ccccc2C(=O)NC)c(Cl)cn1]

To a 5-mL microwave tube were added 2-[(2,5-dichloro-4-pyridinyl)amino]-N-methylbenzamide (100 mg, 0.338 mmol), 1-ethyl-3-[2-(1-pyrrolidinyl)ethyl]-1H-pyrazol-5-amine (70.3 mg, 0.338 mmol), cesium carbonate (330 mg, 1.013 mmol), and 1,4-dioxane (2 mL), and the mixture was degassed by bubbling nitrogen through for 15 min. Palladium (II) acetate (3.79 mg, 0.017 mmol) and BINAP (21.03 mg, 0.034 mmol) were added, and the reaction mixture was heated at 170° C. with stirring under microwave conditions for 40 min. The reaction mixture was filtered and concentrated. The residue was purified by using RP-HPLC under basic conditions (Gemini 5u C18(2) 110A, AXI. 50×30.00 mm 5 micron: 7.3-minute run, 47 mL/min, 40% ACN/H$_2$O, 0.1% NH$_4$OH to 90% ACN/H$_2$O, 0.1% NH$_4$OH with UV detection at 254 nm) to give the title compound (62 mg). MS: (M+H)$^+$=468.1. $^1$H NMR (400 MHz, DMSO-d$_6$) ppm 1.21 (t, J=7.2 Hz, 3 H), 1.67 (m, 4H), 2.45 (m, 4), 2.60 (m, 4H), 2.77 (d, J=4.0 Hz, 3H), 3.89 (q, J=7.2 Hz, 2H), 6.03 (s, 1H), 6.74 (s, 1H), 7.11 (m, 1H), 7.49 (m, 1H), 7.54 (m, 1H), 7.71 (d, J=7.2 Hz, 1H), 8.00 (s, 1H).

Intermediate 7

2-Amino-N-methoxy-benzamide

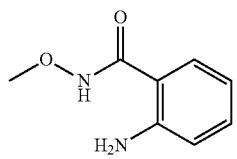

To a mixture of isatoic anhydride (40 g, 245.39 mmol, 1 eq) and o-methyl hyroxylamine hydrochloride (30.55 g, 368.09 mmole, 1.5 eq) in EtOH:H$_2$O (9:1) (1000 mL) was added triethylamine (51.2 mL, 368.09 mmole, 1.5 eq) and resulting mixture was reflux for 4 h. After completion of reaction solvent was removed under reduced pressure and residue was diluted with water (500 mL), extracted with ethyl acetate (3×250 mL). Combined organic layer was dried over sodium sulfate, filtered and concentrated under reduced pressure. Solid compound so obtained was purified by washing with diethyl ether and hexane to give the title compound as brown solid (20 g, 49%). $^1$H-NMR (400 MHz, DMSO-d$_6$): δ 3.67 (s, 3H), 6.20-6.40 (brs, 2H), 6.44-6.53 (m, 1H), 6.70 (d, 1H, J=7.76 Hz), 7.10-7.19 (m, 1H), 7.30 (d, 1H, J=7.6 Hz), 11.40 (s, 1H). LC-MS [M+H]$^+$=167.2.

Intermediate 8

2-(2,5-Dichloropyridin-4-ylamino)-N-methoxy-benzamide (CR637-KS210635-027A1)

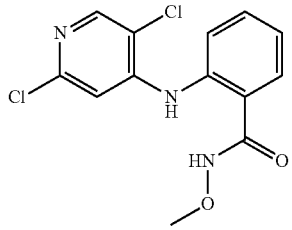 [SMILES: CONC(=O)c1ccccc1Nc1cc(Cl)ncc1Cl]

A mixture of 2,5-dichloro-4-iodo-pyridine (40 g, 146.5 mmole, 1 eq), 2-amino-N-methoxy-benzamide (24.32 g, 146.5 mmole, 1 eq) and K$_3$PO$_4$ (77.72 g 366.2 mmole, 2.5 eq) in 1,4-dioxane (600 mL) was degassed with N$_2$ for 1 h. To this were added Pd(OAc)$_2$ (0.657 g, 2.93 mmole, 0.02 eq), DPEPhos (6.31 g, 11.7 mmole, 0.08 eq) and again degassed for 15 min with N$_2$. The resulting mixture was stirred at 110° C. for overnight. After completion of reaction, solid material was collected by filtration, dissolved in water (500 mL) and extracted with ethyl acetate (5×200 mL). Combined organic layer was dried over sodium sulfate, filtered and concentrated under reduced pressure. Solid compound so obtained was purified by washing with hexane to give the title compound as yellowish solid (40 g, 53%). $^1$H-NMR (400 MHz, DMSO-d$_6$): δ 3.63 (s, 3H), 7.06 (s, 1H), 7.15-7.22 (m, 1H), 7.48-7.57 (m, 2H), 7.66-7.67 (d, 1H, J=7.48 Hz), 8.25 (s, 1H), 10.66-11.45 (brs, 1H). LC-MS [M+H]$^+$=312.3.

Example 47

2-({5-Chloro-2-[(1,5-dimethyl-1H-pyrazol-4-yl)amino]-4-pyridinyl}amino)-N-(methyloxy)benzamide

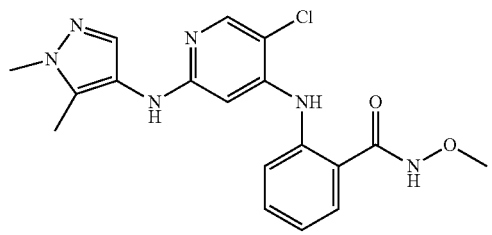

A microwave tube was charged with 2-[(2,5-dichloro-4-pyridinyl)amino]-N-(methyloxy)benzamide (200 mg, 0.64 mmol), 1,5-dimethyl-1H-pyrazol-4-amine (142 mg, 1.28 mmol), cesium carbonate (626 mg, 1.92 mmol) and dioxane/THF (3:1 ml). The reaction mixture was degassed under nitrogen for 10 min and palladium (II) acetate (5.8 mg, 0.03 mmol) and BINAP (40 mg, 0.06 mmol) were added. The tube was sealed and the mixture was stirred in an oil bath at 150° C. overnight. The dark brown solution was filtered thru celite and evaporated. It was dissolved in MeOH and filtered thru an Acrodisc (Pall Corporation; www.pall.com) and further purified on preparative Agilent HPLC (5 to 95% water:acetonitrile with 0.1% formic acid). The dark brown oil residue was dissolved in DMF and water was slowly added. A tan precipitate crashed out and was filtered off and dried under vacuum at 40° C. for 2 hrs to afford the desired product (18 mg, 7.3%) as a tan solid. LC-MS [M+H]$^+$= 387.1, 389.1. 1H NMR (400 MHz, DMSO-d$_6$) δ ppm 11.91 (br. s., 1 H) 9.41 (br. s., 1 H) 7.85-7.98 (m, 2 H) 7.49-7.59 (m, 3 H) 7.42 (br. s., 1 H) 7.07-7.13 (m, 1 H) 6.50 (br. s., 1 H) 3.69 (d, J=10.36 Hz, 6 H) 2.11 (s, 3 H).

Example 48

2-({5-Chloro-2-[(1,3-dimethyl-1H-pyrazol-4-yl)amino]-4-pyridinyl}amino)-N-(methyloxy)benzamide

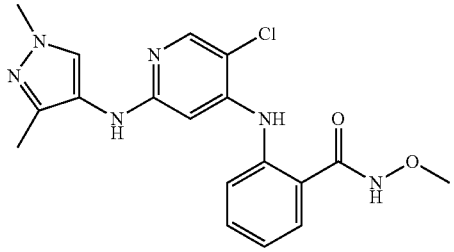 [SMILES: CONC(=O)c1ccccc1Nc1cc(Nc2cn(C)nc2C)ncc1Cl]

A microwave tube was charged with 2-[(2,5-dichloro-4-pyridinyl)amino]-N-(methyloxy)benzamide (250 mg, 0.8 mmol), 1,3-dimethyl-1H-pyrazol-4-amine (187 mg, 1.68 mmol), cesium carbonate (783 mg, 2.4 mmol) and dioxane/THF (3:1 ml). The reaction mixture was degassed under nitrogen for 10 min and palladium (II) acetate (9 mg, 0.04 mmol) and BINAP (50 mg, 0.08 mmol) were added. The mixture was stirred in a microwave at 140° C. for 40 min. It was evaporated and the residue dissolved in MeOH was filtered thru celite and thru an Acrodisc and purified further using preparative Agilent HPLC (5 to 95% water:acetonitrile with 0.1% formic acid). Fractions were combined and evaporated. Ether was added to the residue and a tan precipitate crashed out. It was filtered off and dried under vacuum at 40° C. for 2 days to afford the desired product (55 mg, 18%) as a tan solid. LC-MS (ES) m/z=387.1, [M+H]$^+$= 389.1. 1H NMR (400 MHz, DMSO-d$_6$) ppm 11.93 (br. s., 1 H) 9.51 (br. s., 1 H) 8.03 (s, 1 H) 7.96 (s, 1 H) 7.82 (s, 1 H) 7.51-7.61 (m, 3 H) 7.07-7.15 (m, 1 H) 6.68 (s, 1 H) 3.70 (d, J=4.29 Hz, 6 H) 2.07 (s, 3 H).

Example 49

2-[(5-Chloro-2-{[4-methyl-1-(1-methylethyl)-1H-pyrazol-5-yl]amino}-4-pyridinyl)amino]-N-(methyloxy)benzamide

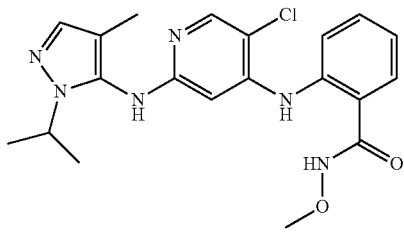 [SMILES: CONC(=O)c1ccccc1Nc1cc(Nc2c(C)cnn2C(C)C)ncc1Cl]

A microwave tube was charged with 2-[(2,5-dichloro-4-pyridinyl)amino]-N-(methyloxy)benzamide (100 mg, 0.32 mmol), 4-methyl-1-(1-methylethyl)-1H-pyrazol-5-amine (93.6 mg, 0.67 mmol), cesium carbonate (312.8 mg, 0.96 mmol) and DMF (5 mL). The reaction mixture was degassed under nitrogen for 10 min and palladium (II) acetate (3.6 mg, 0.016 mmol) and BINAP (19.9 mg, 0.032 mmol) were added. The reaction mixture was heated in an oil bath for 6 hours and then in a microwave at 150° C. for 40 min. The solvent was evaporated and the residue dissolved in MeOH. It was filtered thru celite and thru an Acrodisc to be purified on preparative Agilent HPLC (5 to 95% water:acetonitrile with 0.1% formic acid). Fractions were combined and evaporated. The brown oil residue was diluted in DMF and water was added. A precipitate crashed out. It was filtered and dried under vacuum at 40° C. for 6 hrs. LC-MS [M+H]$^+$=415.1. 1H NMR (400 MHz, DMSO-d$_6$) ppm 11.93 (s, 1 H) 9.48 (br. s., 1 H) 8.23 (s, 1 H) 7.93 (s, 1 H) 7.58 (d, J=7.83 Hz, 1 H) 7.50 (d, J=3.79 Hz, 2 H) 7.24 (s, 1 H) 7.12 (dt, J=7.83, 4.17 Hz, 1 H) 6.40 (br. s., 1 H) 4.33 (dt, J=13.14, 6.57 Hz, 1 H) 3.71 (s, 3 H) 1.78 (s, 3 H) 1.26 (d, J=6.57 Hz, 6 H).

Example 50

2-({5-Chloro-2-[(1-ethyl-4-methyl-1H-pyrazol-5-yl)amino]-4-pyridinyl}amino)-N-(methyloxy)benzamide

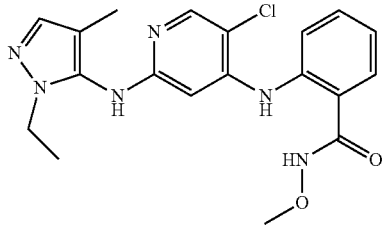 [SMILES: CCn1ncc(C)c1Nc1cc(Nc2ccccc2C(=O)NOC)c(Cl)cn1]

A microwave tube was charged with 2-[(2,5-dichloro-4-pyridinyl)amino]-N-(methyloxy)benzamide (300 mg, 0.96 mmol), 1-ethyl-4-methyl-1H-pyrazol-5-amine (253 mg, 2.01 mmol), cesium carbonate (939 mg, 2.88 mmol) and DMF (7 ml). The reaction mixture was degassed under nitrogen for 10 min and palladium (II) acetate (10.8 mg, 0.05 mmol) and BINAP (59.8 mg, 0.096 mmol) were added. The reaction mixture was heated in an oil bath at 90° C. for 5 hrs and then in a microwave at 150° C. for 50 min. It was evaporated and the residue was dissolved in MeOH, filtered thru celite and thru an Acrodisc and purified further on preparative Agilent HPLC (5 to 95% water:acetonitrile with 0.1% formic acid). Fractions were combined and evaporated. The brown oil residue was diluted in DMF and water was added. A precipitate crashed out. It was filtered off and dried under vacuum at 40° C. for 5 hrs. LC-MS [M+H]$^+$=401.1. 1H NMR (400 MHz, DMSO-d$_6$) ppm 11.92 (s, 1 H) 9.48 (br. s., 1 H) 8.27 (s, 1 H) 7.94 (s, 1 H) 7.59 (d, J=7.58 Hz, 1 H) 7.51 (d, J=3.54 Hz, 2 H) 7.22 (s, 1 H) 7.09-7.16 (m, 1 H) 6.40 (s, 1 H) 3.85 (q, J=7.33 Hz, 2 H) 3.71 (s, 3 H) 1.79 (s, 3 H) 1.21 (t, J=7.20 Hz, 3 H).

Example 51

2-[(5-Chloro-2-{[4-methyl-1-(2-methylpropyl)-1H-pyrazol-5-yl]amino}-4-pyridinyl)amino]-N-(methyloxy)benzamide

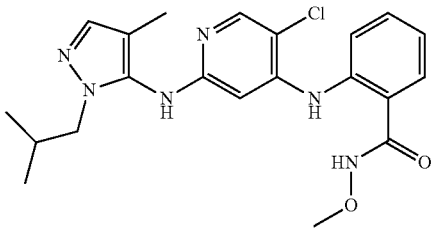 [SMILES: CONC(=O)c1ccccc1Nc1cc(Nc2c(C)cnn2CC(C)C)ncc1Cl]

A microwave tube was charged with 2-[(2,5-dichloro-4-pyridinyl)amino]-N-(methyloxy)benzamide (300 mg, 0.96 mmol), 4-methyl-1-(2-methylpropyl)-1H-pyrazol-5-amine (309 mg, 2.01 mmol), cesium carbonate (939 mg, 2.88 mmol) and DMF (5 ml). The reaction mixture was degassed under nitrogen for 10 min, and palladium (II) acetate (10.8 mg, 0.05 mmol) and BINAP (59.8 mg, 0.096 mmol) were added. The reaction mixture was heated in an oil bath at 90° C. for 5 hrs and then in a microwave at 150° C. for 40 min. Solvent was evaporated and the residue was dissolved in MeOH, filtered thru celite and thru an Acrodisc an purified further using preparative Agilent HPLC (5 to 95% water:acetonitrile with 0.1% formic acid). Fractions were combined and evaporated. The brown oil residue was diluted in DMF and water was added. A precipitate crashed out. It was filtered off and dried under vacuum at 40° C. for 5 hrs. LC-MS [M+H]$^+$=429.1. 1H NMR (400 MHz, DMSO-d$_6$) ppm 11.93 (s, 1 H) 9.48 (br. s., 1 H) 8.26 (s, 1 H) 7.94 (s, 1 H) 7.58 (d, J=7.33 Hz, 1 H) 7.44-7.51 (m, 2 H) 7.23 (s, 1 H) 7.08-7.16 (m, 1 H) 6.38 (s, 1 H) 3.70 (s, 3 H) 3.65 (d, J=7.33 Hz, 2 H) 2.03 (dt, J=13.71, 6.92 Hz, 1 H) 1.77 (s, 3 H) 0.75 (d, J=6.57 Hz, 6 H).

Example 52

2-[(5-Chloro-2-{[3-(hydroxymethyl)-1-(1-methylethyl)-1H-pyrazol-5-yl]amino}-4-pyridinyl)amino]-N-(methyloxy)benzamide

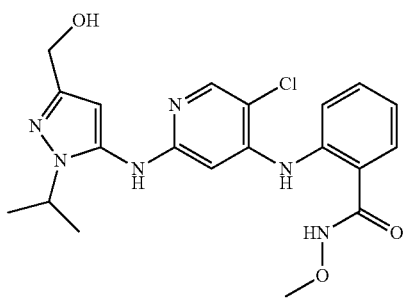 [SMILES: CONC(=O)c1ccccc1Nc1cc(Nc2cc(CO)nn2C(C)C)ncc1Cl]

A microwave tube was charged with 2-[(2,5-dichloro-4-pyridinyl)amino]-N-(methyloxy)benzamide (188 mg, 0.602 mmol), [5-amino-1-(1-methylethyl)-1H-pyrazol-3-yl]methanol (140 mg, 0.90 mmol), cesium carbonate (589 mg, 1.81 mmol) and DMF (5 ml). The reaction mixture was degassed under nitrogen for 10 min and palladium (II) acetate (6.8 mg, 0.03 mmol) and BINAP (37.5 mg, 0.06 mmol) were added. The reaction mixture was heated in an oil bath at 90° C. for 5 hrs and then in a microwave at 150° C. for 40 min. It was evaporated and the residue was dissolved in MeOH, filtered thru celite and thru an Acrodisc and purified further using preparative Agilent HPLC (5 to 95% water:acetonitrile with 0.1% formic acid). Fractions were combined and evaporated. EtOAc was added to the brown oil residue. Then the mixture was heated and hexane was added dropwise. A light yellow precipitate crashed out upon sonication. It was filtered off and dried under vacuum at 40° C. for 12 hrs. LC-MS [M+H]$^+$=431.2. 1H NMR (400 MHz, DMSO-d$_6$) ppm 11.93 (br. s., 1 H) 9.54 (br. s., 1 H) 8.54 (s, 1 H) 7.96-8.01 (m, 1 H) 7.52-7.62 (m, 3 H) 7.11-7.16 (m, 1 H) 6.70 (s, 1 H) 6.10 (s, 1 H) 4.95 (t, J=5.81 Hz, 1 H) 4.43 (dt, J=13.14, 6.57 Hz, 1 H) 4.33 (d, J=5.56 Hz, 2 H) 3.71 (s, 3 H) 1.29 (d, J=6.57 Hz, 6 H).

Intermediate 9

2-(2-Chloro-5-cyclopropyl-pyridin-4-ylamino)-N-methyl-benzamide 1

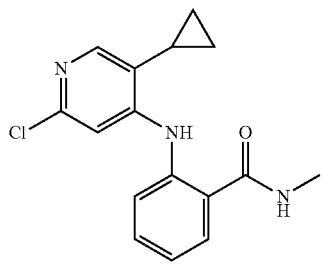 [SMILES: CNC(=O)c1ccccc1Nc1cc(Cl)ncc1C1CC1]

A solution of cyclopropylboronic acid (0.38 g, 4.40 mmole, 1.5 eq) in toluene (100 mL) was degassed with N$_2$ at 50° C. for 15 min. To this was added Pd(PPh$_3$)$_4$ (0.17 g, 0.15 mmole, 0.05 eq) and 2-(5-bromo-2-chloro-pyridin-4-ylamino)-N-methyl-benzamide (1 g, 2.93 mmole, 1 eq) and the resulting reaction mixture was again degassed for 30 min. To this a degassed solution K$_3$PO$_4$ (2.49 g, 11.72 mmole, 4 eq) in H$_2$O (4 mL) was added in one portion and the resulting reaction mixture was refluxed for overnight. Solvent was removed under reduced pressure and the residue was diluted with water (100 mL) and then extracted with DCM (3×75 mL). Combined organic layer was dried over sodium sulfate, filtered and concentrated under reduced pressure to yield crude product. Crude compound was purified by column chromatography over silica gel (60-120 mesh) using 0.5% MeOH-DCM as the eluant to give the title compound as a pale yellow solid (0.480 g, 54%). $^1$H-NMR (400 MHz, DMSO-d$_6$): δ 0.60-0.70 (m, 2H), 0.95-1.05 (m, 2H), 1.60-1.71 (m, 1H), 2.76 (d, 3H, J=4.48 Hz), 7.09 (s, 1H), 7.10-7.18 (m, 1H), 7.49-7.60 (m, 2H), 7.68-7.70 (d, 1H, J=7.64 Hz), 7.93 (s, 1H), 8.60-8.70 (m, 1H), 10.22 (s, 1H). LC-MS [M+H]$^+$=302.0.

Example 53

2-[5-Cyclopropyl-2-(2,5-dimethyl-2H-pyrazol-3-ylamino)-pyridin-4-ylamino]-N-methyl-benzamide

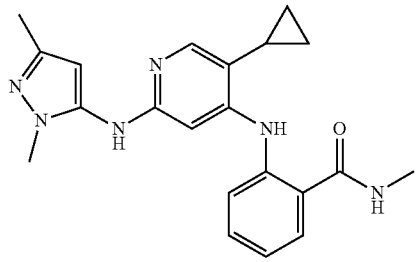 [SMILES: CNC(=O)c1ccccc1Nc1cc(Nc2cc(C)nn2C)ncc1C1CC1]

To a 10 mL microwave tube were added 2-(2-chloro-5-cyclopropyl-pyridin-4-ylamino)-N-methyl-benzamide (0.075 g, 0.25 mmol, 1 eq), 2,5-dimethyl-2H-pyrazol-3-ylamine (0.030 g, 0.27 mmol, 1.1 eq), Cs$_2$CO$_3$ (0.23 g, 0.70 mmol, 2.8 eq) and 1,4-dioxane (4 mL) and resulting mixture was degassed with N$_2$ for 30 minutes. To this was added Pd$_2$(dba)$_3$ (0.008 g, 0.007 mmol, 0.03 eq) and xanthphos (0.009 g, 0.014 mmol, 0.06 eq) and reaction mixture was degassed again with N$_2$ for another 15 minutes. The resulting reaction mixture was irradiated in a CEM microwave at 110° C. and 150 W for 40 min. The progress of reaction was monitored by LCMS. After completion of reaction, Cs$_2$CO$_3$ was removed by filtration and the filtrate was concentrated under reduced pressure to give a crude product. The crude compound was purified by column chromatography over neutral alumina using 0.1% MeOH-DCM as the eluant. Solid compound so obtained was washed with diethyl ether and pentane to give the title compound as a yellowish solid (16 mg, 17%). $^1$H-NMR (400 MHz, DMSO-d$_6$): δ 0.52-0.59 (m, 2H), 0.89-0.99 (m, 2H), 1.52-1.62 (m, 1H), 2.05 (s, 3H), 2.76-2.77 (d, 3H, J=4.44 Hz), 3.52 (s, 3H), 5.96 (s, 1H), 6.69 (s, 1H), 7.01-7.05 (t, 1H, J=7.48 Hz), 7.42-7.45 (m, 1H), 7.51-7.60 (m, 1H) 7.64-7.66 (d, 1H, J=7.32 Hz), 7.72 (s, 1H), 8.37 (s, 1H), 8.55-8.65 (brs, 1H), 9.96 (s, 1H). LC-MS [M+H]$^+$=377.2.

Example 54

2-[5-Cyclopropyl-2-(2-ethyl-5-methyl-2H-pyrazol-3-ylamino)-pyridin-4-ylamino]-N-methylbenzamide

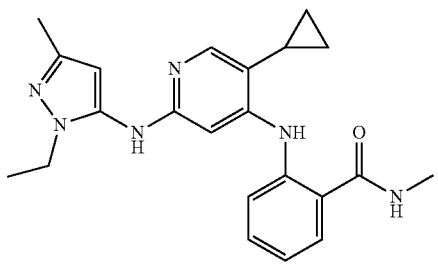 [SMILES: CCn1nc(C)cc1Nc1cc(Nc2ccccc2C(=O)NC)c(C2CC2)cn1]

To a 10 mL microwave tube were added 2-(2-chloro-5-cyclopropyl-pyridin-4-ylamino)-N-methyl-benzamide (0.075 g, 0.25 mmol, 1 eq), 2-ethyl-5-methyl-2H-pyrazol-3-ylamine (0.035 g, 0.27 mmol, 1.1 eq), $Cs_2CO_3$ (0.23 g, 0.70 mmol, 2.8 eq) and 1,4-dioxane (3 mL) and the resulting mixture was degassed with $N_2$ for 30 minutes. To this mixture was added $Pd_2(dba)_3$ (0.008 g, 0.007 mmol, 0.03 eq) and xanthphos (0.009 g, 0.015 mmol, 0.06 eq) and this mixture was degassed again with $N_2$ for another 10 minutes. The resulting reaction mixture was irradiated in a CEM microwave at 110° C. and 150 W for 45 min. The progress of the reaction was monitored by LCMS. After completion of the reaction, $Cs_2CO_3$ was removed by filtration and the filtrate was concentrated under reduced pressure to give a crude product. It was purified using column chromatography over neutral alumina using 0.2% MeOH-DCM as the eluant. The solid compound so obtained was washed with diethyl ether and hexane to give the title compound as a white solid (20 mg, 20%). $^1$H-NMR (400 MHz, DMSO-$d_6$): δ 0.50-0.62 (m, 2H), 0.88-0.99 (m, 2H), 1.15-1.28 (m, 3H), 1.55-1.65 (m, 1H), 2.07 (s, 3H), 2.76-2.77 (d, 3H, J=4.36 Hz), 3.82-3.95 (m, 2H), 5.95 (s, 1H), 6.68 (s, 1H), 6.99-7.10 (m, 1H), 7.42-7.50 (m, 1H), 7.50-7.55 (m, 1H) 7.64-7.66 (d, 1H, J=7.6 Hz), 7.71 (s, 1H), 8.30 (s, 1H), 8.55-8.70 (brs, 1H), 9.95 (s, 1H). LC-MS [M+H]$^+$=391.4.

Intermediate 10

2-(5-Bromo-2-chloro-pyridin-4-ylamino)-N-methoxy-benzamide

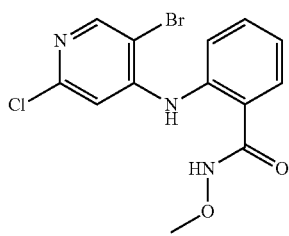 [SMILES: CONC(=O)c1ccccc1Nc1cc(Cl)ncc1Br]

A mixture of 5-bromo-2-chloro-4-iodo-pyridine (5 g, 15.72 mmole, 1 eq), 2-amino-N-methoxy-benzamide (2.61 g, 15.72 mmole, 1 eq) and $K_3PO_4$ (8.34 g, 39.3 mmole, 2.5 eq), and 1,4-dioxane (30 mL) was degassed with $N_2$ for 1 h. To this was added DPEPhos (0.67 g, 1.25 mmole, 0.08 eq) and $Pd(OAc)_2$ (0.07 g, 0.31 mmole, 0.02 eq) and this mixture was degassed again with $N_2$ for 30 min. The resulting mixture was refluxed for overnight. After completion of reaction, solvent was removed under reduced pressure and residue was diluted with water (100 mL) and extracted with 5% MeOH-DCM (3×100 mL). Combined organic layers were dried over sodium sulfate, filtered and concentrated under reduced pressure to give a crude compound. It was purified by column chromatography over silica gel (60-120 mesh) using 20% Ethyl acetate-hexane as the eluant to yield the title compound as off white solid (3.5 g, 62%). $^1$H-NMR (400 MHz, DMSO-$d_6$): δ 3.56 (s, 3H), 6.88-6.98 (m, 1H), 7.08 (s, 1H), 7.17-7.25 (m, 1H), 7.26-7.35 (m, 1H), 7.82-7.90 (m, 1H), 8.23 (s, 1H), 12.86 (brs, 1H). LC-MS [M+H]$^+$=356.30.

Intermediate 11

2-(2-Chloro-5-cyclopropyl-pyridin-4-ylamino)-N-methoxy-benzamide

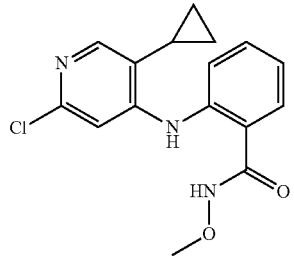 [SMILES: CONC(=O)c1ccccc1Nc1cc(Cl)ncc1C1CC1]

In a sealable tube toluene (50 mL) was degassed with $N_2$ at 50° C. for 15 min and to this 2-(5-bromo-2-chloro-pyridin-4-ylamino)-N-methoxy-benzamide (1.5 g, 4.21 mmole, 1 eq), cyclopropylboronic acid (1.4 g, 16.85 mmole, 4 eq) and $Pd(PPh_3)_4$ (0.24 g, 0.21 mmole, 0.05 eq) were added and resulting mixture was degassed for 30 min. To this NaBr (0.44 g, 4.33 mmole, 1.03 eq) and a solution of KF (0.8 g, 13.90 mmole, 3.3 eq) in $H_2O$ (3 mL) were added; again degassed with $N_2$ for 15 min. The tube was sealed and the resulting mixture was heated at 100° C. for 24 h. After completion of reaction, reaction mixture was allowed to cool at room temperature, poured into water (100 mL) and extracted with toluene (2×50 mL). Combined organic layer was dried over sodium sulfate, filtered and concentrated under reduced pressure. The crude compound was purified by washing with 0.5% DCM-$Et_2O$ to give titled compound as pale yellow solid (0.7 g, 53%). $^1$H-NMR (400 MHz, DMSO-$d_6$): δ 0.57-072 (m, 2H), 0.97-1.10 (m, 2H), 1.62-1.75 (m, 1H), 3.68 (s, 3H), 7.02 (s, 1H), 7.11-7.20 (m, 1H), 7.51-7.67 (m, 3H), 7.94 (s, 1H), 9.62 (s, 1H), 11.92 (brs, 1H). LC-MS [M+H]$^+$=318.2.

Example 55

2-[5-Cyclopropyl-2-(2,5-dimethyl-2H-pyrazol-3-ylamino)-pyridin-4-ylamino]-N-methoxy-benzamide

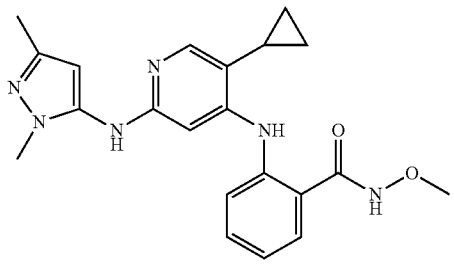 [SMILES: CONC(=O)c1ccccc1Nc1cc(Nc2cc(C)nn2C)ncc1C1CC1]

To a 10 mL microwave tube were added 2-(2-chloro-5-cyclopropyl-pyridin-4-ylamino)-N-methoxy-benzamide (0.075 g, 0.24 mmol, 1 eq), 2,5-dimethyl-2H-pyrazol-3-ylamine (0.05 g, 0.47 mmol, 2 eq), $Cs_2CO_3$ (0.23 g, 0.71 mmol, 3 eq), and 1,4-dioxane (3 mL). The resulting mixture was degassed with $N_2$ for 15 min. To this was added $Pd_2(dba)_3$ (0.015 g, 0.014 mmol, 0.06 eq) and xanthphos (0.03 g, 0.06 mmol, 0.25 eq) and the mixture was again degassed with $N_2$ for 30 min. The resulting mixture was irradiated in a CEM microwave at 120° C., 150 W for 35 min. After completion of reaction, solvent was removed under reduced pressure and crude compound was purified using column chromatography over silica gel (100-200 mesh) using 1% MeOH-DCM as the eluant followed by prep HPLC. Solid compound so obtained was washed with diethyl ether and pentane to give the title compound as an off white solid (11 mg, 12%). $^1$H-NMR (400 MHz, DMSO-$d_6$): δ 0.52-0.60 (m, 2H), 0.82-1.00 (m, 2H), 1.50-1.62 (m, 1H), 2.05 (s, 3H), 3.52 (s, 3H), 3.70 (s, 3H), 5.96 (s, 1H), 6.67 (s, 1H), 6.98-7.10 (m, 1H), 7.40-7.60 (m, 3H), 7.73 (s, 1H), 8.39 (s, 1H), 9.46 (s, 1H), 11.88 (brs, 1H). LC-MS [M+H]$^+$=393.4.

Example 56

2-[5-Cyclopropyl-2-(2-ethyl-5-methyl-2H-pyrazol-3-ylamino)-pyridin-4-ylamino]-N-methoxy-benzamide

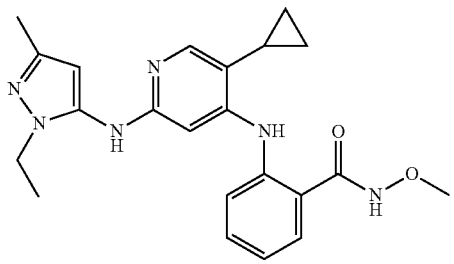 [SMILES: CCn1nc(C)cc1Nc1cc(Nc2ccccc2C(=O)NOC)c(C2CC2)cn1]

To a 10 mL microwave tube were added 2-(2-chloro-5-cyclopropyl-pyridin-4-ylamino)-N-methoxy-benzamide (0.075 g, 0.24 mmol, 1 eq), 2-ethyl-5-methyl-2H-pyrazol-3-ylamine (0.05 g, 0.36 mmol, 1.5 eq), $Cs_2CO_3$ (0.23 g, 0.71 mmol, 3 eq), and 1,4-dioxane (3 mL) and the resulting mixture was degassed with $N_2$ for 15 min. To this was added $Pd_2(dba)_3$ (0.014 g, 0.014 mmol, 0.06 eq) and xanthphos (0.03 g, 0.06 mmol, 0.25 eq) and this mixture was again degassed with $N_2$ for another 10 min. The resulting mixture was irradiated in a CEM microwave at 120° C., 150 W for 35 min. After the reaction was finished solvent was removed under reduced pressure and crude product was purified by column chromatography over silica gel (100-200 mesh) using 1% MeOH-DCM as the eluant followed by washing with diethyl ether and pentane and DCM to give the title compound as an off white solid (5 mg, 5%). $^1$H-NMR (400 MHz, DMSO-$d_6$): δ 0.50-0.60 (m, 2H), 0.88-1.00 (m, 2H), 1.15-1.27 (m, 3H), 1.55-1.65 (m, 1H), 2.07 (s, 3H), 3.70 (s, 3H), 3.80-3.95 (m, 2H), 5.95 (s, 1H), 6.64 (s, 1H), 6.90-7.10 (m, 1H), 7.40-7.60 (m, 3H), 7.72 (s, 1H), 8.34 (s, 1H), 9.47 (s, 1H), 11.88 (brs, 1H). LC-MS [M+H]$^+$=407.3.

Intermediate 12

2-(2-Chloro-5-isopropenyl-pyridin-4-ylamino)-N-methyl-benzamide

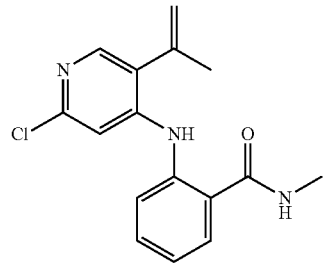 [SMILES: C=C(C)c1cnc(Cl)cc1Nc1ccccc1C(=O)NC]

In a tube a solution of isopropenyboronic acid pinacol ester (3.31 mL, 17.6 mmole, 3 eq) in toluene (200 mL) was degassed with $N_2$ at 50° C. for 15 min. To this was added Pd(PPh$_3$)$_4$ (0.68 g, 0.59 mmole, 0.1 eq) and 2-(5-bromo-2-chloro-pyridin-4-ylamino)-N-methyl-benzamide (2 g, 5.87 mmole, 1 eq). This mixture was again degassed with $N_2$ for 30 min. A degassed solution of $K_3PO_4$ (4.98 g, 23.48 mmole, 4 eq) in $H_2O$ (8 mL) was added to the above mixture in one portion and the resulting mixture was heated at 110° C. for overnight. After completion of the reaction, it was allowed to cool to room temperature and solvent was removed under reduced pressure to yield crude product. It was purified by column chromatography over silica gel (60-120 mesh) using 0.5% MeOH-DCM as the eluant to give the title compound as an off white solid (0.8 g, 45%). $^1$H-NMR (400 MHz, DMSO-$d_6$): δ 2.06 (s, 3H), 2.73-2.74 (d, 3H, J=4.52 Hz), 5.14 (s, 1H), 5.46 (s, 1H), 7.04-7.15 (m, 2H), 7.45-7.60 (m, 2H), 7.64-7.71 (m, 1H), 7.96 (s, 1H), 8.60-8.72 (brs, 1H), 9.87 (s, 1H). LC-MS [M+H]$^+$=302.2.

Example 57

2-[2-(2,5-Dimethyl-2H-pyrazol-3-ylamino)-5-isopropenyl-pyridin-4-ylamino]-N-methyl-benzamide

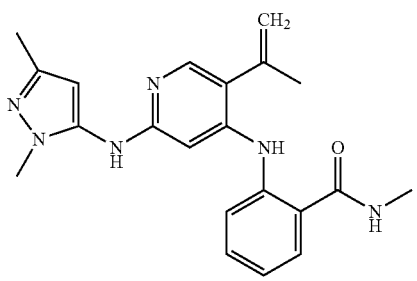 [SMILES: C=C(C)c1cnc(Nc2cc(C)nn2C)cc1Nc1ccccc1C(=O)NC]

To a 10 mL microwave tube was added 2-(2-chloro-5-isopropenyl-pyridin-4-ylamino)-N-methyl-benzamide (0.075 g, 0.25 mmol, 1 eq), 2,5-dimethyl-2H-pyrazol-3-ylamine (0.055 g, 0.50 mmol, 2 eq), $Cs_2CO_3$ (0.24 g, 0.74 mmol, 3 eq) and 1,4-dioxane (3 mL). The resulting mixture was degassed with $N_2$ for 30 minutes. Then $Pd(OAc)_2$ (0.015 g, 0.07 mmol, 0.27 eq) and BINAP (0.046 g, 0.074 mmol, 0.3 eq) were added and the mixture degassed again with $N_2$ for another 10 minutes. The resulting reaction mixture was irradiated in a CEM microwave at 110° C. and 150 W for 45 min. The progress of the reaction was monitored by LCMS. After it was complete, $Cs_2CO_3$ was removed by filtration and the filtrate was concentrated under reduced pressure. The resulting crude product was purified by column chromatography over neutral alumina using 0.2% MeOH-DCM as the eluant. This gave the title compound as an off white solid (180 mg, 48%). $^1$H-NMR (400 MHz, DMSO-$d_6$): δ 2.02-2.10 (m, 6H), 2.73-2.74 (d, 3H, J=4.48 Hz), 3.53 (s, 3H), 5.05 (s, 1H), 5.31 (s, 1H), 5.97 (s, 1H), 6.67 (s, 1H), 6.90-7.05 (m, 1H), 7.4-7.55 (m, 2H), 7.61-7.63 (d, 1H, J=7.04 Hz), 7.76 (s, 1H), 8.48 (s, 1H), 8.54-8.67 (brs, 1H), 9.61 (s, 1H). LC-MS [M+H]$^+$=377.4.

Example 58

2-[2-(2,5-Dimethyl-2H-pyrazol-3-ylamino)-5-isopropyl-pyridin-4-ylamino]-N-methyl-benzamide

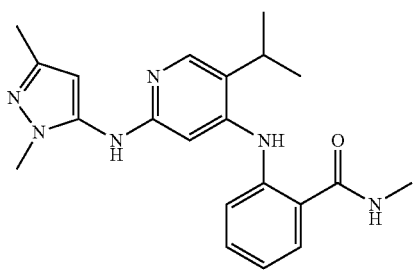 [SMILES: CNC(=O)c1ccccc1Nc1cc(Nc2cc(C)nn2C)ncc1C(C)C]

A solution of 2-[2-(2,5-dimethyl-2H-pyrazol-3-ylamino)-5-isopropenyl-pyridin-4-ylamino]-N-methyl-benzamide (0.13 g, 0.345 mmole, 1 eq) in ethanol (10 mL) was degassed with $N_2$ and to this $PtO_2$(0.012 g, 0.052 mmole, 0.15 eq) was added. The resulting mixture was stirred at room temperature under $H_2$ atmosphere with balloon pressure for 10 h. After completion of the reaction, it was filtered through a celite bed which was then washed with ethanol (10 mL). The filtrate was evaporated under reduced pressure to give a solid residue which was purified by washing with diethyl ether to give the title compound as a gray solid (80 mg, 61%). $^1$H-NMR (400 MHz, DMSO-$d_6$): δ 1.24-1.26 (d, 6H, J=6.76 Hz), 2.05 (s, 3H), 2.75-2.76 (d, 3H, J=4.48 Hz), 2.89-3.10 (m, 1H), 3.53 (s, 3H), 5.96 (s, 1H), 6.67 (s, 1H), 6.85-7.10 (m, 1H), 7.40-7.50 (m, 2H), 7.65-7.67 (d, 1H, J=7.76 Hz), 7.86 (s, 1H), 8.36 (s, 1H), 8.60-8.70 (brs, 1H), 9.89 (s, 1H). LC-MS [M+H]$^+$=379.2.

Example 59

2-({5-Chloro-2-[(1,5-dimethyl-1H-pyrazol-4-yl)amino]-4-pyridinyl}amino)-N-methylbenzamide

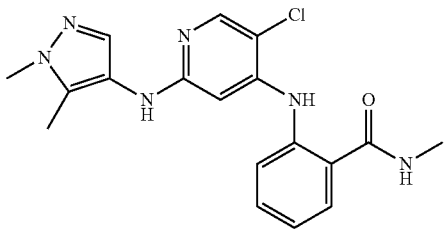

To a 10 mL sealable tube was added 2-[(2,5-dichloro-4-pyridinyl)amino]-N-methylbenzamide (95 mg, 0.321 mmol), 1,5-dimethyl-1H-pyrazol-4-amine (35.7 mg, 0.321 mmol), BINAP (20 mg, 0.032 mmol), cesium carbonate (314 mg, 0.964 mmol), and palladium(II) acetate (7.21 mg, 0.032 mmol) in 1,4-dioxane (5 mL). The reaction vessel was sealed and heated at 150° C. for 1 hr. The reaction mixture was purified using a prep HPLC (0.1% formic acid, 5 to 95% water:acetonitrile). Fractions were combined and evaporated. 2-({5-Chloro-2-[(1,5-dimethyl-1H-pyrazol-4-yl)amino]-4-pyridinyl}amino)-N-methylbenzamide (16 mg, 0.037 mmol, 11.38% yield) was isolated as yellow oil LCMS (M+H)$^+$=371.1; 1H NMR (400 MHz, MeOD) ppm 2.17 (s, 3 H) 2.91 (s, 3 H) 3.78 (s, 3 H) 6.47 (s, 1 H) 7.13-7.24 (m, 1 H) 7.40 (s, 1 H) 7.46-7.57 (m, 2 H) 7.67 (dd, J=7.83, 1.26 Hz, 1 H) 7.82 (s, 1 H).

Example 60

2-{[5-Chloro-2-({1-ethyl-3-[(methyloxy)methyl]-1H-pyrazol-5-yl}amino)-4-pyridinyl]amino}-N-methylbenzamide

60a)

1-Ethyl-3-[(methyloxy)methyl]-1H-pyrazol-5-amine

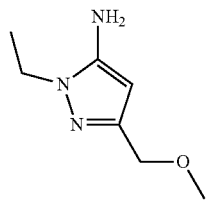

To a 25 mL round bottom was added 4-(methyloxy)-3-oxobutanenitrile (500 mg, 4.42 mmol), ethyl hydrazine (655 mg, 4.42 mmol), and 2 M HCl (2.210 mL, 4.42 mmol) in ethanol (10 mL). The reaction mixture was stirred at the room temperature overnight. The reaction mixture was then evaporated and pardoned between 20 mL of ethyl acetate and 20 mL of 1 M Na$_2$CO$_3$. The organic layer was washed with brine, filtered and evaporated to obtain 1-ethyl-3-[(methyloxy)methyl]-1H-pyrazol-5-amine (450 mg, 2.465 mmol, 55.8% yield) as a yellow oil. The product was used in the next step without further purification. LCMS (M+H)$^+$=156.1; 1H NMR (400 MHz, DMSO-d$_6$) ppm 1.20 (t, J=7.20 Hz, 3 H) 3.19 (s, 3 H) 3.82 (q, J=7.33 Hz, 2 H) 4.11 (s, 2 H) 5.11 (s, 2 H) 5.22 (s, 1H).

60b) 2-{[5-chloro-2-({1-ethyl-3-[(methyloxy)methyl]-1H-pyrazol-5-yl}amino)-4-pyridinyl]amino}-N-methylbenzamide

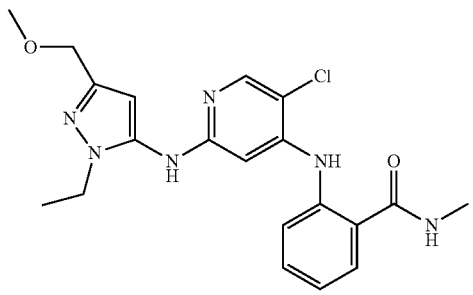

The title compound was prepared substantially as described in Example 59 except using 1-ethyl-3-[(methyloxy)methyl]-1H-pyrazol-5-amine instead of 5-amino-1-methyl-1H-pyrazole. LCMS (M+H)$^+$=415.1 (M+H); 1H NMR (400 MHz, DMSO-d$_6$) ppm 1.24 (t, J=7.20 Hz, 3 H) 2.78 (d, J=4.55 Hz, 3 H) 3.23 (s, 3 H) 3.95 (q, J=7.07 Hz, 2 H) 4.25 (s, 2 H) 6.20 (s, 1 H) 6.77 (s, 1 H) 7.05-7.16 (m, 1 H) 7.44-7.60 (m, 2 H) 7.70 (dd, J=7.83, 1.26 Hz, 1 H) 8.01 (s, 1 H) 8.63 (s, 1 H) 8.69 (q, J=4.29 Hz, 1 H) 10.12 (s, 1 H).

Example 61

2-[(5-Chloro-2-{[3-[(ethyloxy)methyl]-1-(1-methylethyl)-1H-pyrazol-5-yl]amino}-4-pyridinyl)amino]-N-methylbenzamide 61a) 3-[(Ethyloxy)methyl]-1-(1-methylethyl)-1H-pyrazol-5-amine

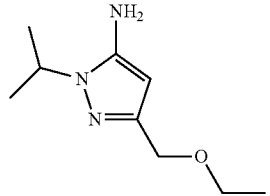

To a 25 mL round bottom was added 4-(ethyloxy)-3-oxobutanenitrile (550 mg, 4.33 mmol), isopropyl hydrazine hydrochloride (478 mg, 4.33 mmol), and HCl (2.163 mL, 4.33 mmol) in Ethanol (10 mL). The reaction mixture was stirred at the room temperature overnight. The reaction mixture was then evaporated, and partitioned between 20 mL of ethyl acetate and 20 mL of 1 M Na$_2$CO$_3$. The organic layer was washed with brine, filtered and evaporated. 3-[(Ethyloxy)methyl]-1-(1-methylethyl)-1H-pyrazol-5-amine (520 mg, 2.84 mmol, 65.6% yield) was isolated as yellow oil. The product was used in the next step without further purification. 1H NMR (400 MHz, DMSO-d$_6$) ppm 1.09 (t, J=7.07 Hz, 3 H) 1.26 (d, J=6.57 Hz, 6 H) 3.40 (q, J=6.91 Hz, 2 H) 4.16 (s, 2 H) 4.32 (quin, J=6.57 Hz, 1 H) 5.06 (s, 2 H) 5.22 (s, 1 H)

61b) 2-[(5-Chloro-2-{[3-[(ethyloxy)methyl]-1-(1-methylethyl)-1H-pyrazol-5-yl]amino}-4-pyridinyl)amino]-N-methylbenzamide

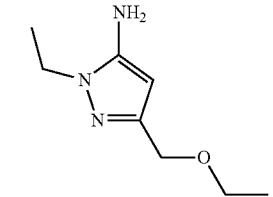

The title compound was prepared substantially as described in Example 59 except using 3-[(ethyloxy)methyl]-1-(1-methylethyl)-1H-pyrazol-5-amine instead of 5-amino-1-methyl-1H-pyrazole. LCMS (ES) m/z=443.1 (M+H); 1H NMR (400 MHz, MeOD) ppm 1.21 (t, J=7.07 Hz, 3 H) 1.40 (d, J=6.82 Hz, 6 H) 2.91 (s, 3 H) 3.56 (q, J=6.91 Hz, 2H) 4.45 (s, 2 H) 4.53 (quin, J=6.69 Hz, 1 H) 6.17 (s, 1 H) 6.60 (s, 1 H) 7.05-7.18 (m, 1 H) 7.40-7.56 (m, 2 H) 7.62-7.70 (m, 1 H) 7.92 (s, 1 H)

Example 62

2-{[5-Chloro-2-({1-ethyl-3-[(ethyloxy)methyl]-1H-pyrazol-5-yl}amino)-4-pyridinyl]amino}-N-methylbenzamide 62a) 1-Ethyl-3-[(ethyloxy)methyl]-1H-pyrazol-5-amine To a 25 mL round bottom was added 4-(ethyloxy)-3-oxobutanenitrile (550 mg, 4.33 mmol), ethyl hydrazine oxalate (641 mg, 4.33 mmol), and HCl (2.163 mL, 4.33 mmol) in ethanol (10 mL). The reaction mixture was stirred at the room temperature overnight. The reaction mixture was then evaporated, and partitioned between 20 mL of ethyl acetate and 20 mL of 1 M Na$_2$CO$_3$. The organic layer was washed with brine, filtered and evaporated. 1-Ethyl-3-[(ethyloxy)methyl]-1H-pyrazol-5-amine (420 mg, 2.234 mmol, 51.6% yield) was isolated as yellow oil. The product was used in the next step without further purification. LCMS (M+H)⁺=170.1 (M+H); 1H NMR (400 MHz, DMSO-$d_6$) ppm 1.08 (t, J=6.95 Hz, 3 H) 1.19 (t, J=7.07 Hz, 3 H) 3.37-3.43 (m, 2 H) 3.81 (q, J=7.24 Hz, 2 H) 4.15 (s, 2 H) 5.09 (s, 2 H) 5.22 (s, 1 H).

62b) 2-{[5-Chloro-2-({1-ethyl-3-[(ethyloxy) methyl]-1H-pyrazol-5-yl}amino)-4-pyridinyl] amino}-N-methylbenzamide

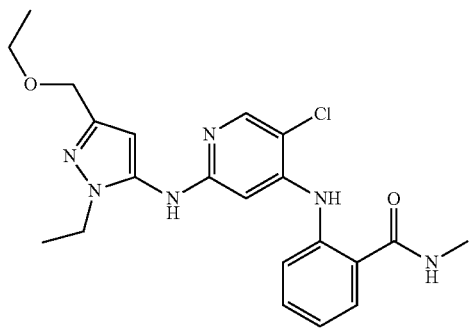 [SMILES: CCOCc1cc(Nc2cc(Nc3ccccc3C(=O)NC)c(Cl)cn2)n(CC)n1]

The title compound was prepared substantially as described in Example 59 except using 1-ethyl-3-[(ethyloxy) methyl]-1H-pyrazol-5-amine instead of 5-amino-1-methyl-1H-pyrazole. LCMS (M+H)⁺=429.1 (M+H); 1H NMR (400 MHz, MeOD) ppm 1.21 (t, J=7.07 Hz, 3 H) 1.34 (t, J=7.33 Hz, 3 H) 2.91 (s, 3 H) 3.55 (q, J=6.91 Hz, 2 H) 4.04 (q, J=7.33 Hz, 2 H) 4.43 (s, 2 H) 6.22 (s, 1 H) 6.66 (s, 1 H) 7.10-7.20 (m, 1 H) 7.45-7.53 (m, 1 H) 7.53-7.58 (m, 1 H) 7.66 (dd, J=7.83, 1.52 Hz, 1 H) 7.93 (s, 1 H).

Example 63

2-({5-Chloro-2-[(1-ethyl-3-methyl-1H-pyrazol-5-yl) amino]-4-pyridinyl}amino)-N-hydroxy-N-methyl-benzamide 63a) 2-({5-Chloro-2-[(1-ethyl-3-methyl-1H-pyrazol-5-yl)amino]-4-pyridinyl}amino)benzonitrile

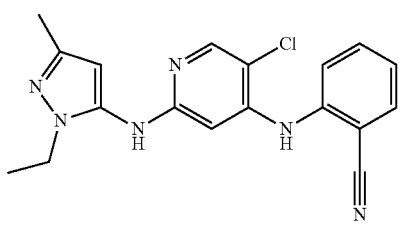 [SMILES: CCn1nc(C)cc1Nc1cc(Nc2ccccc2C#N)c(Cl)cn1]

To a 50 mL tube was added 2-[(2,5-dichloro-4-pyridinyl) amino]benzonitrile (738 mg, 2.80 mmol), 1-ethyl-3-methyl-1H-pyrazol-5-amine (350 mg, 2.80 mmol), BINAP (696 mg, 1.118 mmol), cesium carbonate (2733 mg, 8.39 mmol) and palladium(II) acetate (62.8 mg, 0.280 mmol) in 1,4-dioxane (15 mL). The reaction mixture was heated to 120° C. for 18 hr. Solid was filtered off and discarded and the solution was concentrated. Product was then dissolved in 1 M HCl (1 mL) and extracted with EtOAc. The organic layer was discarded. The water layer was neutralized with 1 M NaOH (to pH 8) and extracted with EtoAc. The organic layer was separated, washed with brine, dried over MgSO₄, filtered and evaporated. The solid was the dissolved in 20 mL of EtOAc and 20 mL of water and 1 mL of acetic acid were added. The organic layer was separated, washed with brine, dried over MgSO₄, filtered and evaporated. 2-({5-Chloro-2-[(1-ethyl-3-methyl-1H-pyrazol-5-yl)amino]-4-pyridinyl}amino)benzonitrile (450 mg, 1.275 mmol, 45.6% yield) was isolated as orange foam. This product was used in the next step without further purification. LCMS (M+H)⁺=353.1; 1H NMR (400 MHz, DMSO-$d_6$) ppm 1.19 (t, J=7.20 Hz, 3 H) 1.91 (s, 3 H) 3.84 (q, J=7.24 Hz, 2 H) 5.92 (s, 1 H) 6.03 (s, 1 H) 7.41 (td, J=7.64, 0.88 Hz, 1 H) 7.48 (d, J=8.08 Hz, 1 H) 7.76 (td, J=7.83, 1.52 Hz, 1 H) 7.91 (dd, J=7.83, 1.52 Hz, 1 H) 7.96 (s, 1 H) 8.47 (d, J=7.07 Hz, 1 H) 11.98 (br. s., 1 H)

63b) 2-({5-Chloro-2-[(1-ethyl-3-methyl-1H-pyrazol-5-yl)amino]-4-pyridinyl}amino)benzoic acid

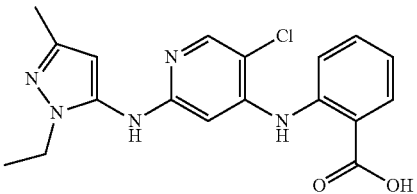 [SMILES: CCn1nc(C)cc1Nc1cc(Nc2ccccc2C(=O)O)c(Cl)cn1]

To a 50 mL round bottom flask was added 2-({5-chloro-2-[(1-ethyl-3-methyl-1H-pyrazol-5-yl)amino]-4-pyridinyl}amino)benzonitrile (300 mg, 0.850 mmol), and NaOH 1 M solution (10 ml, 10.00 mmol) in 1,4-dioxane (10 mL). The mixture was heated under reflux for 18 hours. Ethyl acetate was added (20 mL) and the layers separated—all product stayed in the water phase. The water phase was neutralized with 6 N HCl, and 40 mL of ethyl acetate were added. The organic layer was separated, washed with brine, dried over MgSO₄, filtered and evaporated. 2-({5-Chloro-2-[(1-ethyl-3-methyl-1H-pyrazol-5-yl)amino]-4-pyridinyl}amino)benzoic acid (220 mg, 0.562 mmol, 66.1% yield) was isolated as off-white solid and used in the next step without further purification. LCMS (M+H)⁺=372.1; 1H NMR (400 MHz, MeOD) ppm 1.33 (t, J=7.20 Hz, 4 H) 2.22 (s, 3 H) 4.00 (q, J=7.33 Hz, 2 H) 6.01 (s, 1 H) 6.82 (s, 1 H) 7.06 (td, J=7.52, 1.14 Hz, 1 H) 7.39-7.49 (m, 1 H) 7.49-7.55 (m, 1 H) 7.87-7.94 (m, 1 H) 8.05 (dd, J=7.83, 1.52 Hz, 1 H).

63c) 2-({5-Chloro-2-[(1-ethyl-3-methyl-1H-pyrazol-5-yl)amino]-4-pyridinyl}amino)-N-hydroxy-N-methylbenzamide

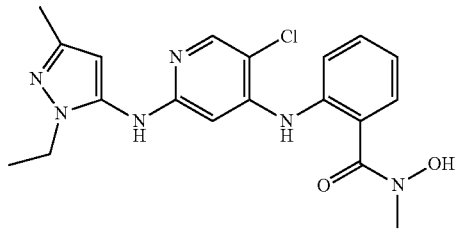 [SMILES: CCn1nc(C)cc1Nc1cc(Nc2ccccc2C(=O)N(C)O)c(Cl)cn1]

A solution of 2-({5-chloro-2-[(1-ethyl-3-methyl-1H-pyrazol-5-yl)amino]-4-pyridinyl}amino)benzoic acid (55 mg, 0.148 mmol), HOBT (22.65 mg, 0.148 mmol) and EDC (28.4 mg, 0.148 mmol) in N,N-dimethylformamide (DMF) (5 mL) was stirred under nitrogen at room temp for 30 minutes. To this solution was added N-methylhydroxylamine (12.35 mg, 0.148 mmol) and the solution was stirred for another 15 minutes. The reaction mixture was cooled to 5° C. and DIEA (0.052 mL, 0.296 mmol) was added dropwise. After addition, the reaction mixture was stirred at room temperature overnight. The reaction mixture was purified using preparative HPLC (0.1% formic acid, 5 to 95% water: acetonitrile). Fractions were combined and evaporated. 2-({5-Chloro-2-[(1-ethyl-3-methyl-1H-pyrazol-5-yl) amino]-4-pyridinyl}amino)-N-hydroxy-N-methylbenzamide (16 mg, 0.034 mmol, 23.05% yield) isolated as a white solid. LCMS (M+H)$^+$=401.0 (M+H); 1H NMR (400 MHz, MeOD) ppm 1.30 (t, J=7.20 Hz, 3 H) 2.19 (s, 3 H) 3.37 (d, J=1.52 Hz, 3 H) 3.96 (q, J=7.07 Hz, 2 H) 5.95 (s, 1 H) 6.32 (s, 1 H) 7.21-7.33 (m, 1 H) 7.42-7.53 (m, 2 H) 7.56 (d, J=7.33 Hz, 1 H) 7.86 (s, 1 H).

Example 64

2-({5-Chloro-2-[(1-ethyl-3-methyl-1H-pyrazol-5-yl) amino]-4-pyridinyl}amino)-N-(ethyloxy)benzamide

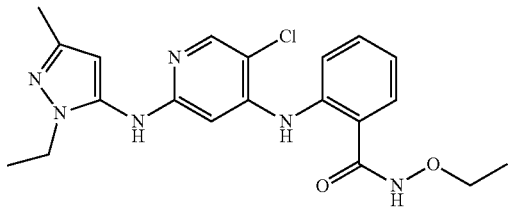 [SMILES: CCONC(=O)c1ccccc1Nc1cc(Nc2cc(C)nn2CC)ncc1Cl]

The title compound was prepared substantially as described in Example 63 except using O-ethylhydroxylamine hydrochloride instead of N-methylhydroxylamine. LCMS (M+H)$^+$=415.1 (M+H); 1H NMR (400 MHz, MeOD) ppm 1.23-1.42 (m, 6 H) 2.21 (s, 3 H) 3.87-4.10 (m, 4 H) 5.99 (s, 1 H) 6.59 (s, 1 H) 7.11-7.28 (m, 1 H) 7.46-7.71 (m, 3 H) 7.92 (s, 1 H).

Intermediate 13

6-Chloro-4-iodo-nicotinonitrile

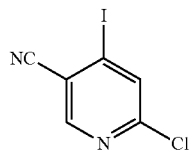

To a mixture of THF (100 mL) and hexane (40 mL) under nitrogen atmosphere was added DIPA (22.21 mL, 158.78 mmole, 1.1 eq). The mixture was cooled to −80° C. and to this was added n-BuLi (63.57 mL, 158.78 mmole, 1.1 eq) dropwise. After completion of addition the resulting mixture was allowed to warm and stirred at −10° C. for 15 min. The reaction mixture was again cooled to −80° C. and a solution of 6-chloro-nicotinonitrile (20 g, 144.35 mmol, 1 eq) in THF (100 mL) was added dropwise. The resulting mixture was stirred at −80° C. for 1 h. After 1 h a solution of iodine (43.96 g, 173.22 mmole, 1.2 eq) in THF (100 mL) was added in one portion. After completion of the reaction, the reaction was quenched with water (100 mL) and extracted with diethyl ether (6×100 mL). Combined organic layers were washed with saturated solution of sodium thiosulfate (2×100 mL), dried over sodium sulfate, filtered and concentrated under vacuum to give crude product. Crude compound was purified by column chromatography over silica gel (100-200 mesh) using 2% ethyl acetate-hexane as the eluant to yield the title compound as a faintly yellow solid (15 g, 39%). $^1$H-NMR (400 MHz, DMSO-d$_6$): δ 8.38 (s, 1H), 8.79 (s, 1H). LC-MS calculated for C$_6$H$_2$ClIN$_2$ (M+H) 264.90, found 264.9.

Intermediate 14

2-(2-Chloro-5-cyanopyridin-4-ylamino)-N-methyl-benzamide

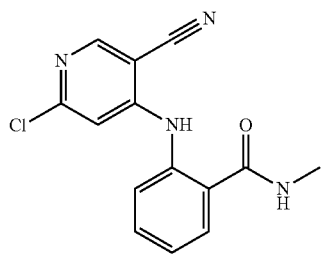 [SMILES: CNC(=O)c1ccccc1Nc1cc(Cl)ncc1C#N]

A mixture of 6-chloro-4-iodo-nicotinonitrile (14 g, 53.03 mmole, 1 eq), 2-amino-N-methoxy-benzamide (7.96 g, 53.03 mmole, 1 eq) and K$_3$PO$_4$ (28.14 g, 132.57 mmole, 2.5 eq) in 1,4-dioxane (250 mL) was degassed with N$_2$ for 1 h. To this mixture were added Pd(OAC)$_2$ (0.238 g, 1.06 mmole, 0.02 eq) and DPEPhos (2.28 g, 4.24 mmole, 0.08 eq). The resulting reaction mixture was degassed with N$_2$ for another 15 min after which the resulting reaction mixture was stirred at 110° C. overnight. After completion of reaction solid material was collected by filtration, dissolved in water (500 mL), and extracted with ethyl acetate (5×200 mL). Combined organic layers were dried over sodium sulfate, filtered and concentrated under reduced pressure to give crude material. It was purified by column chromatography over silica gel (60-120 mesh) using 0.2% methanolic ammonia (10% ammonia in MeOH) in dichloromethane as the eluant to give the title compound as a pale yellow solid (9 g, 59%). $^1$H-NMR (400 MHz, DMSO-d$_6$): δ 2.75 (d, 3H, J=4.56 Hz), 7.09 (s, 1H), 7.25-7.35 (m, 1H), 7.53-7.60 (m, 2H), 7.72 (d, 1H, J=7.48 Hz), 8.56 (s, 1H), 8.69-8.79 (brs, 1H), 10.65 (s, 1H). LC-MS calculated for C$_{14}$H$_{11}$ClN$_4$O (M+H) 287.06, found 286.9.

Intermediate 15

5-[4-(2-Hydroxyethyl)-1-piperazinyl]-N-methyl-2-nitrobenzamide 3

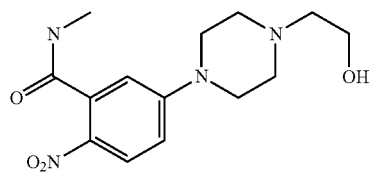 [SMILES: CNC(=O)c1cc(N2CCN(CCO)CC2)ccc1[N+](=O)[O-]]

A solution of 5-fluoro-N-methyl-2-nitrobenzamide, 1-(2-hydroxyethyl)piperazine, and Hunig's base in 20 mL of DMF was stirred at room temperature over the weekend. The resulting mixture was rotavaped to dryness, and the residue was purified by flash column SF40-150 at 2%-10% MeOH/CH$_2$Cl$_2$. Product came out at 7% MeOH/CH$_2$Cl$_2$. MS(ES) m/e 309 [M+H].

Intermediate 16

2-amino-5-[4-(2-Hydroxyethyl)-1-piperazinyl]-N-methylbenzamide 4

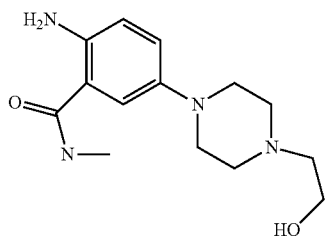 [SMILES: CNC(=O)c1cc(N2CCN(CCO)CC2)ccc1N]

A solution of 5-[4-(2-hydroxyethyl)-1-piperazinyl]-N-methyl-2-nitrobenzamide 3 in 250 mL of MeOH in a 250 mL round bottom flask was stirred at room temperature under hydrogen balloon over night. The resulted mixture was filtered to get rid of the Pd catalyst. TLC in 10% MeOH/CH$_2$Cl$_2$ showed no more starting material and a major product. The solvent was rotavaped to dryness, and the residue was used without further purification. MS(ES) m/e 279 [M+H].

Example 65

2-({5-Cyano-2-[(1,3-dimethyl-1H-pyrazol-5-yl)amino]-4-pyridinyl}amino)-N-methylbenzamide

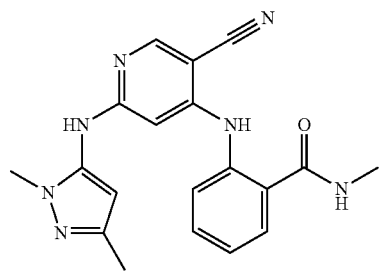

2-({5-Cyano-2-[(1,3-dimethyl-1H-pyrazol-5-yl)amino]-4-pyridinyl}amino)-N-methylbenzamide was synthesized substantially according to the procedure of example 55 using Intermediate 15 and 5-amino-1,3-dimethylpryazole. $^1$H-NMR (400 MHz, DMSO-d$_6$): δ 2.08 (d, 3H), 2.77 (d, 3H), 3.53 (s, 3H), 6.01 (s, 1H), 6.59 (s, 1H), 6.01 (s, 1H), 7.18 (t, 1H), 7.54 (t, 2H), 7.72 (d, 1H), 8.33 (s, 1H), 8.71 (d, 1H), 9.15 (s, 1H), 10.33 (s, 1H). LC-MS (M+H)$^+$=362.0.

Example 66

2-[(2,5-Dichloro-4-pyridinyl)amino]-5-[4-(2-hydroxyethyl)-1-piperazinyl]-N-methylbenzamide 6

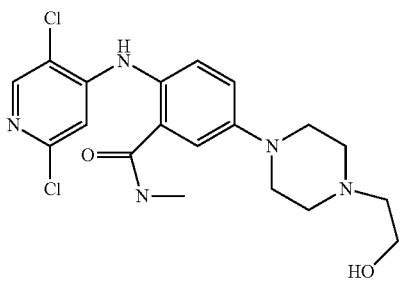 [SMILES: CNC(=O)c1cc(N2CCN(CCO)CC2)ccc1Nc1cc(Cl)ncc1Cl]

A sealed tube was charged with 2,5-dichloro-4-iodopyridine, 2-amino-5-[4-(2-hydroxyethyl)-1-piperazinyl]-N-methylbenzamide 4, and cesium carbonate in 1,4-dioxane. The reaction mixture was degassed by nitrogen for 10 min. At same time BINAP and palladium(II) acetate were added into it and the reaction mixture was heated in 120° C. in an oil bath over night.

TLC in 10% EtOAc/hexane showed no 2,5-dichloro-4-indopyridine. TLC in 10% MeOH/CH$_2$Cl$_2$ showed no 2-amino-5-[4-(2-hydroxyethyl)-1-piperazinyl]-N-methylbenzamide. LCMS showed the reaction had a peak that could be the desired product. While the reaction mixture temperature was maintained at around 80° C., it was filtered, and the solid was washed with THF and CH$_3$CN. The solid was filtered, dried by vacuum, and purified by flash column 1-8% MeOH/CH$_2$Cl$_2$, to give the captioned product as a brown oil. MS(ES) m/e 426 [M+2H].

Example 67

2-({5-Chloro-2-[(1-ethyl-1H-pyrazol-5-yl)amino]-4-pyridinyl}amino)-5-[4-(2-hydroxyethyl)-1-piperazinyl]-N-methylbenzamide 9

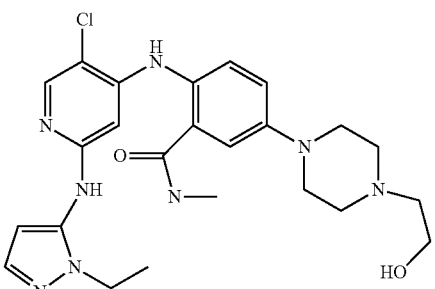

A sealed tube was charged with 2-[(2,5-dichloro-4-pyridinyl)amino]-5-[4-(2-hydroxyethyl)-1-piperazinyl]-N-methylbenzamide 6, 1-ethyl-1H-pyrazol-5-amine, and cesium carbonate in 1,4-dioxane. The reaction mixture was degassed by nitrogen for 10 min. At same time, BINAP and palladium(II) acetate were added and the reaction mixture was heated to 160° C. in microwave for 40 minutes. LCMS showed a peak believed to be the desired product. The solvent was rotavaped to dryness, and the residue was purified by HPLC to give the captioned product. MS(ES) m/e 500 [M+H].

Example 68

2-({5-Chloro-2-[(1,3-dimethyl-1H-pyrazol-5-yl)amino]-4-pyridinyl}amino)-5-[4-(2-hydroxyethyl)-1-piperazinyl]-N-methylbenzamide 10

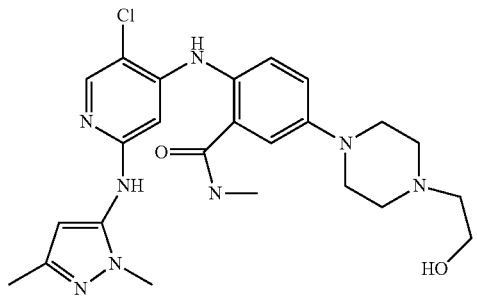 [SMILES: CNC(=O)c1cc(N2CCN(CCO)CC2)ccc1Nc1cc(Nc2cc(C)nn2C)ncc1Cl]

A sealed tube was charged with 2-[(2,5-dichloro-4-pyridinyl)amino]-5-[4-(2-hydroxyethyl)-1-piperazinyl]-N-methylbenzamide 6,1-ethyl-1H-pyrazol-5-amine, and cesium carbonate in 1,4-dioxane. The reaction mixture was degassed by nitrogen for 10 min. Then BINAP and palladium(II) acetatge were added into it, and the reaction mixture was heated to 160° C. in microwave for 40 minutes. LCMS showed the a peak believed to correspond to the desired product. The solvent was rotavaped to dryness, and the residue was purified by HPLC to give product. MS(ES) m/e 500 [M+H].

Example 69

4-Chloro-2-[(5-chloro-2-{[3-methyl-1-(1-methylethyl)-1H-pyrazol-5-yl]amino}-4-pyridinyl)amino]-N-(methyloxy)benzamide

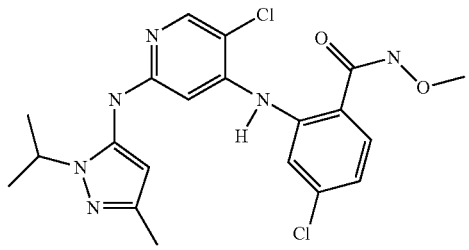 [SMILES: CONC(=O)c1ccc(Cl)cc1Nc1cc(Nc2cc(C)nn2C(C)C)ncc1Cl]

Step 1:

To a degassed solution of 2,5-dichloro-4-iodopyridine (4.5 g, 16.43 mmol), 2-amino-4-chlorobenzonitrile (2.507 g, 16.43 mmol) and potassium triphosphate (10.46 g, 49.3 mmol) in 1,4-dioxane (60 ml) stirred under nitrogen at the room temperature was added DPEPhos (0.708 g, 1.314 mmol) and palladium acetate (0.148 g, 0.657 mmol). The reaction mixture was stirred at the reflux for 18 hr. The reaction mixture was filtered. The solution was evaporated. Ether (50 ml) was added and the formed solid was filtered.

4-chloro-2-[(2,5-dichloro-4-pyridinyl)amino]benzonitrile (2.8 g, 9.38 mmol, 57.1% yield) was isolated as an orange solid. $^1$H NMR (400 MHz, DMSO-$d_6$) ppm 6.70 (s, 1 H) 7.53 (dd, J=8.34, 2.02 Hz, 1 H) 7.65 (d, J=2.02 Hz, 1 H) 7.95 (d, J=8.34 Hz, 1 H) 8.28 (s, 1 H) 9.12 (br. s., 1 H); HPLC Rt=3.50 min, MS (ESI): 298.0, 300.0 [M+H]$^+$.

Step 2.

A solution of 4-chloro-2-[(2,5-dichloro-4-pyridinyl)amino]benzonitrile (2.8 g, 9.38 mmol), 3-methyl-1-(1-methylethyl)-1H-pyrazol-5-amine (1.305 g, 9.38 mmol) and cesium carbonate (9.17 g, 28.1 mmol) in 1,4-dioxane (40 mL) was degassed. DPEPhos (0.404 g, 0.750 mmol) followed by palladium acetate (0.084 g, 0.375 mmol) were added, and the suspension was refluxed overnight. The solid was filtered, the reaction mixture was evaporated. The black oil was purified by flush column chromatography on silica gel (5% EtOAc:DCM). The combined fractions were evaporated. The resulting oil was dissolved in dioxane (20 mL) and sodium hydroxide (20 mL, 20.00 mmol) was added and the reaction mixture was refluxed overnight. The layers were separated and the organic layer was washed with 20 ml of 1 M NaOH. The aqueous layers were combined and washed with EtOAc. The combined organic layers were washed with water, brine and dried over MgSO$_4$ and filtered. The solution was evaporated, suspended in acetonitrile and filtered. 4-Chloro-2-[(5-chloro-2-{[3-methyl-1-(1-methylethyl)-1H-pyrazol-5-yl]amino}-4-pyridinyl)amino]benzoic acid (260 mg, 0.619 mmol, 6.60% yield) was isolated as a yellow solid. $^1$H NMR (400 MHz, DMSO-$d_6$) ppm 1.28 (d, J=6.57 Hz, 6 H) 1.91 (s, 1 H) 2.13 (s, 3 H) 4.43 (quin, J=6.57 Hz, 1 H) 5.97 (s, 1 H) 6.78 (s, 1 H) 7.05 (dd, J=8.46, 1.89 Hz, 1 H) 7.48 (d, J=1.77 Hz, 1 H) 7.96 (d, J=8.34 Hz, 1 H) 8.03 (s, 1 H) 8.61 (s, 1H); HPLC Rt=2.70 min, MS (ESI): 420.1, 422.0 [M+H]$^+$.

Step 3.

To the solution of 4-chloro-2-[(5-chloro-2-{[3-methyl-1-(1-methylethyl)-1H-pyrazol-5-yl]amino}-4-pyridinyl)amino]benzoic acid (260 mg, 0.619 mmol) in N,N-dimethylformamide (DMF) (20 mL) was added HOBT (114 mg, 0.742 mmol) and EDC (142 mg, 0.742 mmol) and the reaction mixture was stirred for 30 min. To this solution was added O-methoxyamine hydrochloride (62.0 mg, 0.742 mmol), and after 30 min the reaction was cooled to 0° C. and DIEA (0.323 mL, 1.856 mmol) was added. The reaction mixture was stirred at the room temperature over the weekend. Water (100 mL) followed by acetic acid (1 mL) were added and the reaction mixture was extracted with 2×50 ml of ethyl acetate. The organic layer was washed with 2×50 ml sat KHCO$_3$, brine, dried over MgSO$_4$ and evaporated. The resulting yellow oil was purified by flash column chromatography on silica gel using DCM:EtOAc (10% to 100%). 4-Chloro-2-[(5-chloro-2-{[3-methyl-1-(1-methylethyl)-1H-pyrazol-5-yl]amino}-4-pyridinyl)amino]-N-(methyloxy)benzamide (85 mg, 0.180 mmol, 29.1% yield) was isolated as white foam. $^1$H NMR (400 MHz, DMSO-$d_6$) ppm 1.27 (d, J=6.57 Hz, 6 H) 2.12 (s, 3 H) 3.70 (s, 3 H) 4.41 (quin, J=6.57 Hz, 1 H) 5.95 (s, 1 H) 6.66 (s, 1 H) 7.01-7.39 (m, 1 H) 7.55-7.88 (m, 2 H) 8.02 (s, 1 H) 8.60 (s, 1 H) 9.76 (br. s., 1 H) 12.01 (br. s., 1 H); HPLC Rt=2.50 min, MS (ESI): 449.0, 451.1 [M+H]$^+$.

Example 70

4-Chloro-2-[(5-chloro-2-{[3-methyl-1-(1-methylethyl)-1H-pyrazol-5-yl]amino}-4-pyridinyl)amino]-N-(methyloxy)benzamide

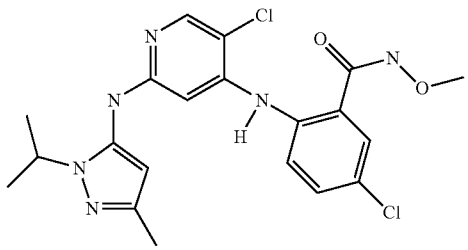 [SMILES: CONC(=O)c1cc(Cl)ccc1Nc1cc(Nc2cc(C)nn2C(C)C)ncc1Cl]

Step 1:

To a degassed solution of 2,5-dichloro-4-iodopyridine (4.5 g, 16.43 mmol), 2-amino-5-chlorobenzonitrile (2.507 g, 16.43 mmol) and potassium triphosphate (10.46 g, 49.3 mmol) in 1,4-dioxane (60 ml) stirred under nitrogen at the room temperature was added DPEPhos (0.708 g, 1.314 mmol) and palladium acetate (0.148 g, 0.657 mmol). The reaction mixture was stirred at reflux for 18 hr. The reaction mixture was filtered. The reaction mixture was evaporated. Ether (50 ml) was added and the solid was filtered. 5-chloro-2-[(2,5-dichloro-4-pyridinyl)amino]benzonitrile (1.8 g, 5.43 mmol, 33.0% yield) was isolated as orange solid. $^1$H NMR (400 MHz, DMSO-d$_6$) ppm 6.63 (s, 1 H) 7.52 (d, J=8.59 Hz, 1 H) 7.81 (dd, J=8.59, 2.53 Hz, 1 H) 8.09 (d, J=2.53 Hz, 1 H) 8.24 (s, 1 H) 9.06 (br. s., 1 H); HPLC Rt=3.53 min, MS (ESI): 298.0, 299.9 [M+H]$^+$.

Step 2.

To a solution of 5-chloro-2-[(2,5-dichloro-4-pyridinyl)amino]benzonitrile (1.8 g, 6.03 mmol) and 3-methyl-1-(1-methylethyl)-1H-pyrazol-5-amine (0.839 g, 6.03 mmol) in 1,4-dioxane (40 mL) was added cesium carbonate (5.89 g, 18.09 mmol) and the reaction mixture was degassed. DPEPhos (0.260 g, 0.482 mmol) was added followed by palladium acetate (0.054 g, 0.241 mmol) and the reaction mixture was heated to reflux overnight. The suspension was then filtered. The dioxane was evaporated. Solid was partitioned between 1 M HCl and ethyl acetate. Layers were separated, and organic layer discarded. The HCl-containing layer was neutralized and extracted with 2×50 mL of ethyl acetate. Organic layers were combined, washed with brine, dried over MgSO$_4$, filtered and evaporated. 5-Chloro-2-[(5-chloro-2-{[3-methyl-1-(1-methylethyl)-1H-pyrazol-5-yl]amino}-4-pyridinyl)amino]benzonitrile (850 mg, 2.118 mmol, 35.1% yield) was isolated as a yellow solid. $^1$H NMR (400 MHz, DMSO-d$_6$) ppm 1.25 (d, J=6.57 Hz, 6H) 2.09 (s, 3 H) 4.35 (quin, J=6.57 Hz, 1 H) 5.89 (s, 1 H) 6.03 (s, 1 H) 7.46 (d, J=8.84 Hz, 1 H) 7.81 (dd, J=8.72, 2.65 Hz, 1 H) 7.96 (s, 1 H) 8.11 (d, J=2.53 Hz, 1 H) 8.42 (s, 1 H) 8.54 (s, 1 H) HPLC Rt=2.60 min, MS (ESI): 400.8, 403.1 [M+H]$^+$.

Step 3.

A solution of 5-chloro-2-[(5-chloro-2-{[3-methyl-1-(1-methylethyl)-1H-pyrazol-5-yl]amino}-4-pyridinyl)amino]benzonitrile (850 mg, 2.118 mmol) in sodium hydroxide −1 M (20 mL, 20.00 mmol) and 1,4-dioxane (20 mL) was refluxed overnight. Ethyl acetate was added and the layers were separated. The organic layer was washed with 1 M NaOH (40 ml). Combined aqueous layers were washed with ethyl acetate. The organic layers were combined, evaporated, dissolved in MeOH and evaporated again. 5-Chloro-2-[(5-chloro-2-{[3-methyl-1-(1-methylethyl)-1H-pyrazol-5-yl]amino}-4-pyridinyl)amino]benzoic acid (800 mg, 1.903 mmol, 90% yield) was isolated as a yellow solid. $^1$H NMR (400 MHz, DMSO-d$_6$) ppm 1.28 (d, J=6.57 Hz, 6 H) 2.12 (s, 3 H) 4.40 (quin, J=6.51 Hz, 1 H) 5.97 (s, 1 H) 6.79 (s, 1 H) 7.56-7.62 (m, 1 H) 7.62-7.69 (m, 1 H) 7.94 (d, J=2.27 Hz, 1 H) 8.04 (s, 1 H) 8.58 (s, 1 H) 9.94 (br. s., 1 H) 13.97 (br. s., 1 H); HPLC Rt=2.65 min, MS (ESI): 420.2, 421.1 [M+H]$^+$.

Step 4.

To a solution of 5-chloro-2-[(5-chloro-2-{[3-methyl-1-(1-methylethyl)-1H-pyrazol-5-yl]amino}-4-pyridinyl)amino]benzoic acid (830 mg, 1.975 mmol) in N,N-dimethylformamide (20 mL) was added HOBT (363 mg, 2.370 mmol) and EDC (454 mg, 2.370 mmol) and the reaction mixture was stirred for 30 min. To this solution was added o-methoxylamine hydrochloride (198 mg, 2.370 mmol) and after 30 min the mixture was cooled to 0° C. DIEA (1.032 mL, 5.92 mmol) was added. The reaction mixture was stirred at the room temperature over the weekend. Water (100 mL) was added followed by acetic acid (1 mL) and the solution extracted with 2×50 ml of ethyl acetate. The organic layer was washed with 2×50 ml sat KHCO$_3$, brine, dried over MgSO$_4$ and evaporated. The product was purified by flash column chromatography on silica gel using EtOAc:DCM (10% to 100%). 5-Chloro-2-[(5-chloro-2-{[3-methyl-1-(1-methylethyl)-1H-pyrazol-5-yl]amino}-4-pyridinyl)amino]-N-(methyloxy)benzamide (250 mg, 0.529 mmol, 26.8% yield) was isolated as a white foam. $^1$H NMR (400 MHz, DMSO-d$_6$) ppm 1.27 (d, J=6.57 Hz, 6 H) 2.11 (s, 3 H) 3.71 (s, 3 H) 4.20-4.55 (m, 1 H) 5.94 (s, 1 H) 6.63 (s, 1 H) 7.59 (s, 2 H) 7.67 (s, 1 H) 7.99 (s, 1 H) 8.50 (s, 1 H) 9.43 (br. s., 1 H) 12.03 (br. s., 1 H); HPLC Rt=2.46 min, MS (ESI): 449.1, 451.1 [M+H]$^+$.

Example 71

2-[(5-Chloro-2-{[3-methyl-1-(1-methylethyl)-1H-pyrazol-5-yl]amino}-4-pyridinyl)amino]-5-fluoro-N-(methyloxy)benzamide

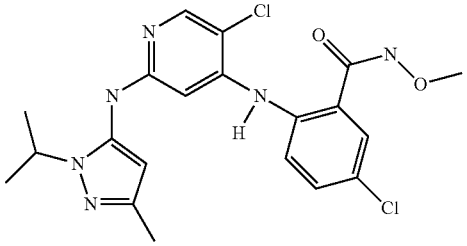 [SMILES: CONC(=O)c1cc(Cl)ccc1Nc1cc(Nc2cc(C)nn2C(C)C)ncc1Cl]

Step 1:

To a degassed solution of 2,5-dichloro-4-iodopyridine (8 g, 29.2 mmol), 2-amino-5-fluorobenzonitrile (3.98 g, 29.2 mmol) and potassium triphosphate (18.60 g, 88 mmol) in 1,4-dioxane (100 ml) stirred under nitrogen at the room temperature was added DPEPhos (1.258 g, 2.337 mmol) and palladium acetate (0.262 g, 1.168 mmol). The reaction mixture was stirred at the reflux for 18 hr. The reaction mixture was filtered. The solvent was evaporated. Ether (50 ml) was added and the solid was filtered. 2-[(2,5-Dichloro-4-pyridinyl)amino]-5-fluorobenzonitrile (7.09 g, 25.1 mmol, 86% yield) was isolated as an orange solid. $^1$H NMR (400 MHz, METHANOL-d$_4$) ppm 6.44 (s, 1 H) 7.46-7.58 (m, 2 H) 7.66 (dd, J=8.08, 2.78 Hz, 1 H) 8.08 (s, 1 H); HPLC Rt=3.23 min, MS (ESI): 382.0, 384.19 [M+H]$^+$.

Step 2.

To a solution of 2-[(2,5-dichloro-4-pyridinyl)amino]-5-fluorobenzonitrile (7.09 g, 25.1 mmol) and 3-methyl-1-(1-methylethyl)-1H-pyrazol-5-amine (3.5 g, 25.1 mmol) in 1,4-dioxane (100 mL) was added cesium carbonate (24.58 g, 75 mmol) and the reaction mixture was degassed. DPEPhos (1.083 g, 2.012 mmol) was added followed by palladium acetate (0.226 g, 1.006 mmol) and the reaction mixture was heated to reflux overnight. The suspension was then filtered. The dioxane was evaporated off. The solid was purified by flash column chromatography on silica gel (10% DCM:EtOAC). Fractions were collected and evaporated. The yellow oil was dissolved in diethyl ether, sonicated and filtered. 2-[(5-Chloro-2-{[3-methyl-1-(1-methylethyl)-1H-pyrazol-5-yl]amino}-4-pyridinyl)amino]-5-fluorobenzonitrile (1.3 g, 3.21 mmol, 12.76% yield) was isolated as a white solid; $^1$H NMR (400 MHz, METHANOL-d$_4$) ppm 1.35 (d, J=6.82 Hz, 6 H) 2.20 (s, 3 H) 4.43 (quin, J=6.69 Hz, 1 H) 5.82 (s, 1 H) 5.89 (s, 1 H) 7.47-7.57 (m, 2 H) 7.61-7.74 (m, 1 H) 7.88 (s, 1 H); HPLC Rt=2.40 min, MS (ESI): 385.2 [M+H]$^+$.

Step 3.

A solution of 2-[(5-chloro-2-{[3-methyl-1-(1-methylethyl)-1H-pyrazol-5-yl]amino}-4-pyridinyl)amino]-5-fluorobenzonitrile (1.3 g, 3.38 mmol) in sodium hydroxide −1 M (10 mL, 10.00 mmol) and 1,4-dioxane (10 mL) was refluxed overnight. Ethyl acetate was added and the layers were separated. The organic layer was washed with 1 M NaOH (40 ml). The combined aqueous layers were washed with ethyl acetate, and neutralized with acetic acid. The product was isolated by filtration. 2-[(5-Chloro-2-{[3-methyl-1-(1-methylethyl)-1H-pyrazol-5-yl]amino}-4-pyridinyl)amino]-5-fluorobenzoic acid (1.1 g, 2.72 mmol, 27.2% yield) was isolated as a yellow solid. $^1$H NMR (400 MHz, DMSO-d$_6$) ppm 1.27 (d, J=6.57 Hz, 6 H) 2.11 (s, 3 H) 4.39 (quin, J=6.57 Hz, 1 H) 5.95 (s, 1 H) 6.70 (s, 1 H) 7.51 (td, J=8.40, 3.16 Hz, 1 H) 7.61 (dd, J=9.09, 4.80 Hz, 1 H) 7.72 (dd, J=9.22, 3.16 Hz, 1 H) 8.00 (s, 1 H) 8.53 (s, 1 H) 9.66 (br. s., 1 H) 13.88 (br. s., 1 H); HPLC Rt=2.44 min, MS (ESI): 404.3 [M+H]$^+$.

Step 4.

To the solution of 2-[(5-chloro-2-{[3-methyl-1-(1-methylethyl)-1H-pyrazol-5-yl]amino}-4-pyridinyl)amino]-5-fluorobenzoic acid (1128 mg, 2.79 mmol) in N,N-dimethylformamide (DMF) (20 mL) was added HOBT (513 mg, 3.35 mmol) followed by EDC (643 mg, 3.35 mmol) and the reaction mixture stirred for 30 min. To this solution was added o-methoxyamine hydrochloride (280 mg, 3.35 mmol) and after 30 min, at 0° C. DIEA (1.460 mL, 8.38 mmol) was added. The reaction mixture was stirred at room temperature 24 hr. Water (100 mL) was added followed by acetic acid (1 mL) and the solution extracted with 2×50 ml of ethyl acetate. The organic layer was separated, washed with 2×50 ml sat KHCO$_3$, brine, dried over MgSO$_4$ and evaporated. The resulting oil was suspended in dichloromethane and filtered. 2-[(5-Chloro-2-{[3-methyl-1-(1-methylethyl)-1H-pyrazol-5-yl]amino}-4-pyridinyl)amino]-5-fluoro-N-(methyloxy)benzamide (620 mg, 1.361 mmol, 48.7% yield) was isolated as a white solid. $^1$H NMR (400 MHz, DMSO-d$_6$) ppm 1.26 (d, J=6.57 Hz, 6 H) 2.10 (s, 3 H) 3.69 (s, 3 H) 4.38 (quin, J=6.57 Hz, 1 H) 5.92 (s, 1 H) 6.50 (s, 1 H) 7.41-7.52 (m, 2 H) 7.58 (dd, J=8.72, 4.67 Hz, 1 H) 7.96 (s, 1 H) 8.46 (s, 1 H) 9.10 (s, 1 H) 11.95 (s, 1 H); HPLC Rt=2.24 min, MS (ESI): 433.4 [M+H]$^+$.

Example 72

2-[(5-Chloro-2-{[3-methyl-1-(1-methylethyl)-1H-pyrazol-5-yl]amino}-4-pyridinyl)amino]-3-fluoro-N-(methyloxy)benzamide

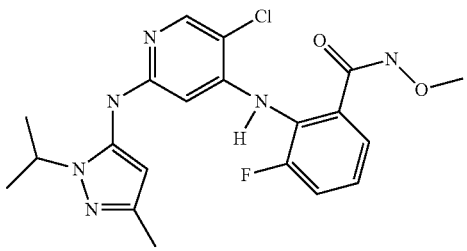 [SMILES: CONC(=O)c1cccc(F)c1Nc1cc(Nc2cc(C)nn2C(C)C)ncc1Cl]

Step 1:

To a degassed solution of 2,5-dichloro-4-iodopyridine (8 g, 29.2 mmol), 2-amino-3-fluorobenzonitrile (3.98 g, 29.2 mmol) and potassium triphosphate (18.60 g, 88 mmol) in 1,4-dioxane (60 ml) stirred under nitrogen at the room temperature was added DPEPhos (1.258 g, 2.337 mmol) and palladium acetate (0.262 g, 1.168 mmol) The reaction mixture was stirred at reflux for 18 hr. The reaction mixture was filtered. 3-Methyl-1-(1-methylethyl)-1H-pyrazol-5-amine (4.07 g, 29.2 mmol) and cesium carbonate (28.6 g, 88 mmol) were added. The reaction mixture was degassed and palladium acetate (0.262 g, 1.168 mmol) and DPEPhos (1.258 g, 2.337 mmol) were added. The reaction mixture was refluxed overnight. The reaction mixture was filtered and the solid was dissolved in water, heated to 50° C. and stirred for 10 minutes, then filtered again. 2-[(5-Chloro-2-{[3-methyl-1-(1-methylethyl)-1H-pyrazol-5-yl]amino}-4-pyridinyl)amino]-3-fluorobenzonitrile (6 g, 15.59 mmol, 53.4% yield) was isolated as an orange solid. $^1$H NMR (400 MHz, DMSO-d$_6$) δ ppm 1.23 (d, J=6.57 Hz, 6 H) 2.07 (s, 3 H) 4.32 (quin, J=6.57 Hz, 1 H) 5.64 (d, J=2.02 Hz, 1 H) 5.83 (s, 1 H) 7.39-7.58 (m, 1 H) 7.63-7.82 (m, 2 H) 7.88 (s, 1 H) 8.26 (br. s., 1 H) 8.41 (br. s., 1 H); HPLC Rt=2.35 min, MS (ESI): 385.0 [M+H]$^+$.

Step 2.

A solution of 2-[(5-chloro-2-{[3-methyl-1-(1-methylethyl)-1H-pyrazol-5-yl]amino}-4-pyridinyl)amino]-3-fluorobenzonitrile (4.5 g, 11.69 mmol) in sodium hydroxide −1 M (10 mL, 10.00 mmol) and 1,4-dioxane (10 mL) was refluxed overnight. Ethyl acetate was added and the layers were separated. The organic layer was washed with 1 M NaOH (40 ml). Combined aqueous layers were washed with ethyl acetate, and neutralized with acetic acid. The solid was filtered. 2-[(5-Chloro-2-{[3-methyl-1-(1-methylethyl)-1H-pyrazol-5-yl]amino}-4-pyridinyl)amino]-3-fluorobenzoic acid (3.2 g, 7.53 mmol, 75% yield) was isolated as a yellow solid. $^1$H NMR (400 MHz, DMSO-d$_6$) ppm 1.24 (d, J=6.57 Hz, 6 H) 2.09 (s, 3 H) 4.34 (quin, J=6.57 Hz, 1 H) 5.86 (s, 1 H) 5.91 (d, J=5.81 Hz, 1 H) 7.35 (td, J=8.02, 4.93 Hz, 1 H) 7.54-7.65 (m, 1 H) 7.81 (d, J=7.58 Hz, 1 H) 7.94 (s, 1 H) 8.45 (s, 1 H) 8.88 (br. s., 1 H) 13.74 (br. s., 1 H); HPLC Rt=2.36 min, MS (ESI): 404.3 [M+H]$^+$.

Step 3.

To a solution of 2-[(5-chloro-2-{[3-methyl-1-(1-methylethyl)-1H-pyrazol-5-yl]amino}-4-pyridinyl)amino]-3-fluorobenzoic acid (3.2 g, 7.92 mmol) in N,N-dimethylformamide (DMF) (50 mL) was added HOBT (1.456 g, 9.51 mmol) and EDC (1.823 g, 9.51 mmol) and the reaction mixture was stirred for 30 min. To this solution was added O-methoxylamine hydrochloride (0.794 g, 9.51 mmol). After 30 min the reaction mixture was cooled to 0° C. and DIEA (4.14 mL, 23.77 mmol) was added. The reaction mixture was stirred at the room temperature 24 hr. Water (100 mL) was added followed by acetic acid (1 mL) and the solution was extracted with 2×50 ml of ethyl acetate. The combined organic layers were washed with 2×50 ml sat KHCO₃, brine, dried over MgSO₄ and evaporated. The oil was suspended in dichloromethane and filtered. 2-[(5-Chloro-2-{[3-methyl-1-(1-methylethyl)-1H-pyrazol-5-yl]amino}-4-pyridinyl)amino]-3-fluoro-N-(methyloxy)benzamide (1.1 g, 2.414 mmol, 30.5% yield) was isolated as a white solid; ¹H NMR (400 MHz, DMSO-d₆) ppm 1.24 (d, J=6.57 Hz, 6 H) 2.08 (s, 3 H) 3.68 (s, 3 H) 4.33 (quin, J=6.57 Hz, 1 H) 5.83 (d, J=5.05 Hz, 1 H) 5.84 (s, 1 H) 7.30-7.49 (m, 2 H) 7.49-7.63 (m, 1 H) 7.92 (s, 1 H) 8.41 (d, J=4.29 Hz, 2 H) 11.85 (s, 1 H); HPLC Rt=2.18 min, MS (ESI): 433.3 [M+H]⁺.

Example 73

2-[(5-Chloro-2-{[3-methyl-1-(1-methylethyl)-1H-pyrazol-5-yl]amino}-4-pyridinyl)amino]-4-fluoro-N-(methyloxy)benzamide

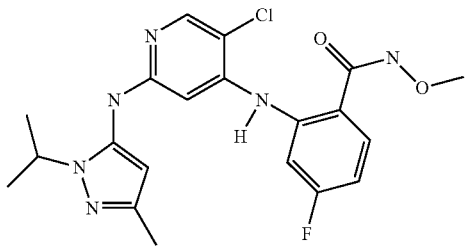 [SMILES: CONC(=O)c1ccc(F)cc1Nc1cc(Nc2cc(C)nn2C(C)C)ncc1Cl]

Step 1:

To a degassed solution of 2,5-dichloro-4-iodopyridine (5 g, 18.26 mmol), 2-amino-4-fluorobenzonitrile (2.485 g, 18.26 mmol) and potassium triphosphate (11.63 g, 54.8 mmol) in 1,4-dioxane (60 ml) stirred under nitrogen at the room temperature was added DPEPhos (0.787 g, 1.460 mmol) and palladium acetate (0.164 g, 0.730 mmol). The reaction mixture was stirred at the reflux for 18 hr. The reaction mixture was filtered. 3-Methyl-1-(1-methylethyl)-1H-pyrazol-5-amine (2.54 g, 18.26 mmol) and cesium carbonate (17.84 g, 54.8 mmol) were added. The reaction mixture was degassed and palladium acetate (0.164 g, 0.730 mmol) and DPEPhos (0.787 g, 1.460 mmol) were added. The reaction mixture was refluxed overnight. The reaction mixture was filtered. NaOH (60 mL, 60.0 mmol) was added and the reaction mixture refluxed overnight. Ethyl acetate was added and the layers were separated. The combined organics were washed with 1 M NaOH (40 ml). The combined aqueous layers were washed with ethyl acetate, and neutralized with acetic acid. 2-[(5-Chloro-2-{[3-methyl-1-(1-methylethyl)-1H-pyrazol-5-yl]amino}-4-pyridinyl)amino]-4-fluorobenzoic acid (2.5 g, 6.19 mmol, 33.9% yield) was isolated by filtration as a yellow solid. ¹H NMR (400 MHz, DMSO-d₆) ppm 1.29 (d, J=6.57 Hz, 6 H) 2.12 (s, 3 H) 4.43 (quin, J=6.57 Hz, 1 H) 5.99 (s, 1 H) 6.86 (s, 1 H) 6.87-6.93 (m, 1 H) 7.34 (dd, J=11.62, 2.53 Hz, 1 H) 8.03-8.10 (m, 2 H) 8.62 (s, 1 H) 10.65 (br. s., 1 H); HPLC Rt=2.57 min, MS (ESI): 404.2 [M+H]⁺.

Step 2.

To a solution of 2-[(5-chloro-2-{[3-methyl-1-(1-methylethyl)-1H-pyrazol-5-yl]amino}-4-pyridinyl)amino]-4-fluorobenzoic acid (2.5 g, 6.19 mmol) in N,N-dimethylformamide (DMF) (50 mL) was added HOBT (1.138 g, 7.43 mmol) and EDC (1.424 g, 7.43 mmol) and the reaction mixture was stirred for 30 min. To this solution was added O-methoxylamine hydrochloride (0.620 g, 7.43 mmol) and after 30 min the mixture was cooled to 0° C. Then DIEA (3.23 mL, 18.57 mmol) was added. The reaction mixture was stirred at the room temperature for 24 hr. Water (100 mL) followed by acetic acid (1 mL) were added and the solution extracted with 2×50 ml of ethyl acetate. The organic layer was washed with 2×50 ml sat KHCO₃, brine, dried over MgSO₄ and condensed. The resulting oil was purified by flash column chromatography on silica gel (2:1 DCM: EtOAc). 2-[(5-Chloro-2-{[3-methyl-1-(1-methylethyl)-1H-pyrazol-5-yl]amino}-4-pyridinyl)amino]-4-fluoro-N-(methyloxy)benzamide (1 g, 2.195 mmol, 35.5% yield) was isolated as a yellow foam. ¹H NMR (400 MHz, DMSO-d₆) ppm 1.28 (d, J=6.57 Hz, 6 H) 2.11 (s, 3 H) 3.71 (s, 3 H) 4.41 (quin, J=6.51 Hz, 1 H) 5.97 (s, 1 H) 6.74 (s, 1 H) 6.87-7.06 (m, 1 H) 7.39 (dd, J=11.37, 2.53 Hz, 1 H) 7.66 (dd, J=8.46, 6.69 Hz, 1 H) 8.03 (s, 1 H) 8.57 (s, 1 H) 9.96 (br. s., 1 H) 11.98 (br. s., 1 H); HPLC Rt=2.36 min, MS (ESI): 433.3 [M+H]⁺.

Example 74

Following substantially the procedure of Example 8 the following compounds can be made starting with either 2,5-dichloro-4-iodopyridine or 2-chloro-4-iodo-5-(trifluoromethyl)pyridine and the appropriately substituted 5-aminopyrazole.

74(a). 2-({5-Chloro-2-[(1,3-dimethyl-1H-pyrazol-5-yl)amino]-4-pyridinyl}amino)-3-fluoro-N-methylbenzamide

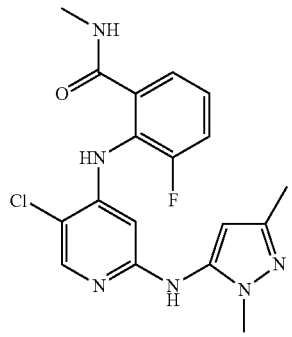 [SMILES: CNC(=O)c1cccc(F)c1Nc1cc(Nc2cc(C)nn2C)ncc1Cl]

81

74(b). 2-({5-Chloro-2-[(1-ethyl-3-methyl-1H-pyrazol-5-yl)amino]-4-pyridinyl}amino)-3-fluoro-N-methylbenzamide

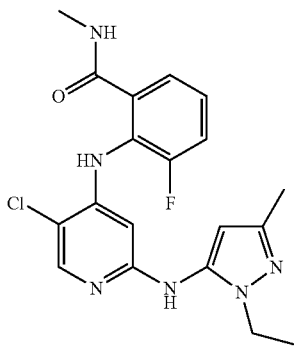 [SMILES: CCn1nc(C)cc1Nc1cc(Nc2c(F)cccc2C(=O)NC)c(Cl)cn1]

74(c). 2-({5-Chloro-2-[(1,5-dimethyl-1H-pyrazol-4-yl)amino]-4-pyridinyl}amino)-3-fluoro-N-methylbenzamide

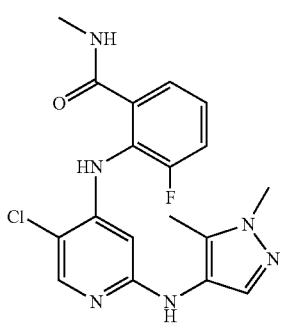 [SMILES: CNC(=O)c1cccc(F)c1Nc1cc(Nc2cnn(C)c2C)ncc1Cl]

74(d). 2-{[2-[(1-Ethyl-3-methyl-1H-pyrazol-5-yl)amino]-5-(trifluoromethyl)-4-pyridinyl]amino}-3-fluoro-N-methylbenzamide

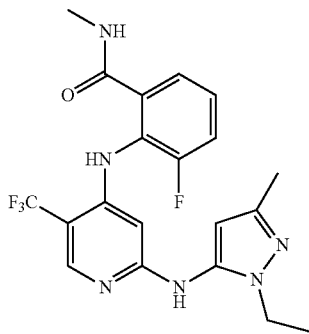 [SMILES: CCn1nc(C)cc1Nc1cc(Nc2c(F)cccc2C(=O)NC)c(C(F)(F)F)cn1]

82

74(e). 2-{[2-[(1,3-Dimethyl-1H-pyrazol-5-yl)amino]-5-(trifluoromethyl)-4-pyridinyl]amino}-3-fluoro-N-methylbenzamide

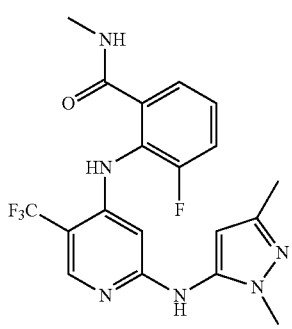 [SMILES: CNC(=O)c1cccc(F)c1Nc1cc(Nc2cc(C)nn2C)ncc1C(F)(F)F]

74(f). 2-{[2-{[1-Ethyl-3-(hydroxymethyl)-1H-pyrazol-5-yl]amino}-5-chloro-4-pyridinyl]amino}-3-fluoro-N-methylbenzamide

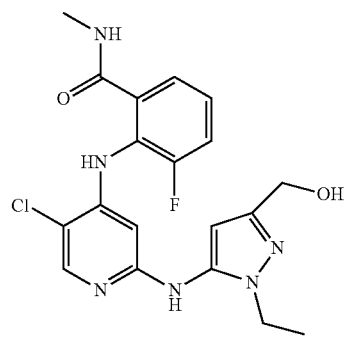 [SMILES: CCn1nc(CO)cc1Nc1cc(Nc2c(F)cccc2C(=O)NC)c(Cl)cn1]

74(g). 3-Fluoro-2-{[2-{[3-(hydroxymethyl)-1-methyl-1H-pyrazol-5-yl]amino}-5-chloro-4-pyridinyl]amino}-N-methylbenzamide

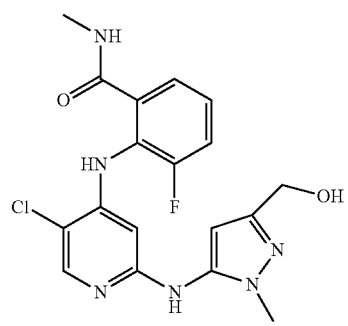 [SMILES: CNC(=O)c1cccc(F)c1Nc1cc(Nc2cc(CO)nn2C)ncc1Cl]

74(h). 2-{[2-{[1-Ethyl-3-(2-hydroxyethyl)-1H-pyrazol-5-yl]amino}-5-chloro-4-pyridinyl]amino}-3-fluoro-N-methylbenzamide

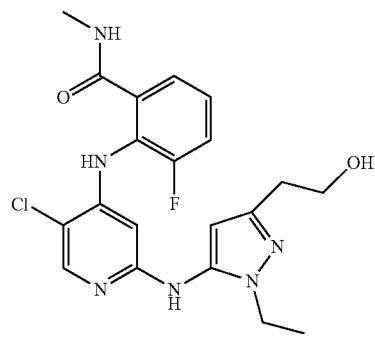 [SMILES: CCn1nc(CCO)cc1Nc1cc(Nc2c(F)cccc2C(=O)NC)c(Cl)cn1]

74(i). 3-Fluoro-2-{[2-{[3-(2-hydroxyethyl)-1-methyl-1H-pyrazol-5-yl]amino}-5-chloro-4-pyridinyl]amino}-N-methylbenzamide

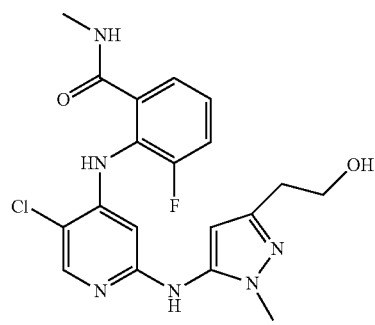 [SMILES: CNC(=O)c1cccc(F)c1Nc1cc(Nc2cc(CCO)nn2C)ncc1Cl]

74(j). 2-{[2-({3-[(Dimethylamino)methyl]-1-methyl-1H-pyrazol-5-yl}amino)-5 chloro-4-pyridinyl]amino}-3-fluoro-N-methylbenzamide

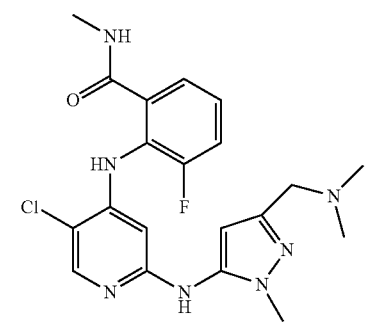 [SMILES: CNC(=O)c1cccc(F)c1Nc1cc(Nc2cc(CN(C)C)nn2C)ncc1Cl]

74(k). 2-{[2-({3-[(Dimethylamino)methyl]-1-ethyl-1H-pyrazol-5-yl}amino)-5 chloro-4-pyridinyl]amino}-3-fluoro-N-methylbenzamide

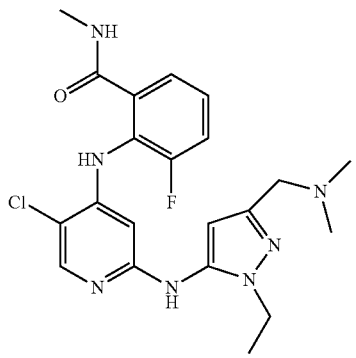 [SMILES: CCn1nc(CN(C)C)cc1Nc1cc(Nc2c(F)cccc2C(=O)NC)c(Cl)cn1]

74(l). 2-({5-Chloro-2-[(3-{[ethyl(methyl)amino]methyl}-1-methyl-1H-pyrazol-5-yl)amino]-4-pyridinyl}amino)-3-fluoro-N-methylbenzamide

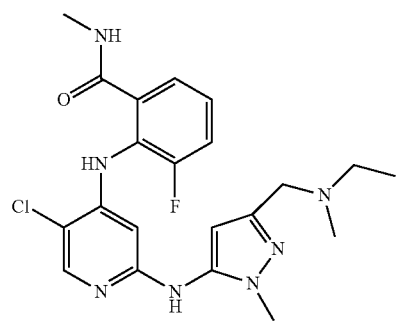 [SMILES: CCN(C)Cc1cc(Nc2cc(Nc3c(F)cccc3C(=O)NC)c(Cl)cn2)n(C)n1]

74(m). 2-{[5-chloro-2-({3-[(diethylamino)methyl]-1-methyl-1H-pyrazol-5-yl}amino)-4-pyridinyl]amino}-3-fluoro-N-methylbenzamide

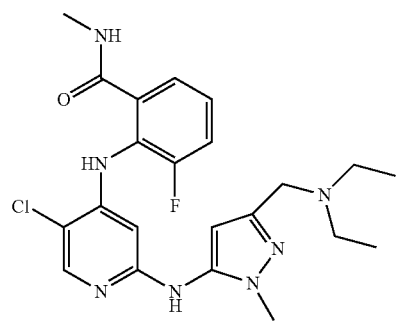 [SMILES: CCN(CC)Cc1cc(Nc2cc(Nc3c(F)cccc3C(=O)NC)c(Cl)cn2)n(C)n1]

74(n). 2-{[2-{[1-Ethyl-3-(hydroxymethyl)-1H-pyrazol-5-yl]amino}-5-(trifluoromethyl)-4-pyridinyl]amino}-3-fluoro-N-methylbenzamide

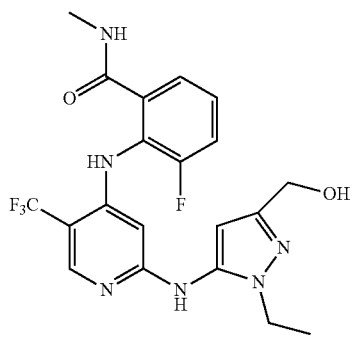 [SMILES: CCn1nc(CO)cc1Nc1cc(Nc2c(F)cccc2C(=O)NC)c(C(F)(F)F)cn1]

74(o). 3-Fluoro-2-{[2-{[3-(hydroxymethyl)-1-methyl-1H-pyrazol-5-yl]amino}-5-(trifluoromethyl)-4-pyridinyl]amino}-N-methylbenzamide

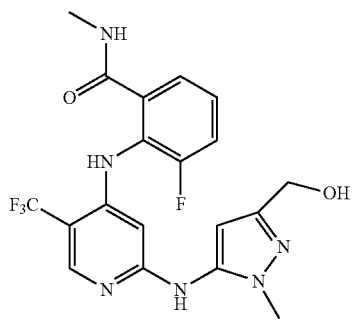 [SMILES: CNC(=O)c1cccc(F)c1Nc1cc(Nc2cc(CO)nn2C)ncc1C(F)(F)F]

74(p). 2-{[2-{[1-Ethyl-3-(2-hydroxyethyl)-1H-pyrazol-5-yl]amino}-5-(trifluoromethyl)-4-pyridinyl]amino}-3-fluoro-N-methylbenzamide

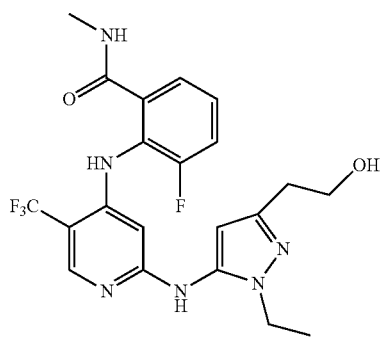 [SMILES: CCn1nc(CCO)cc1Nc1cc(Nc2c(F)cccc2C(=O)NC)c(C(F)(F)F)cn1]

74(q). 3-Fluoro-2-{[2-{[3-(2-hydroxyethyl)-1-methyl-1H-pyrazol-5-yl]amino}-5-(trifluoromethyl)-4-pyridinyl]amino}-N-methylbenzamide

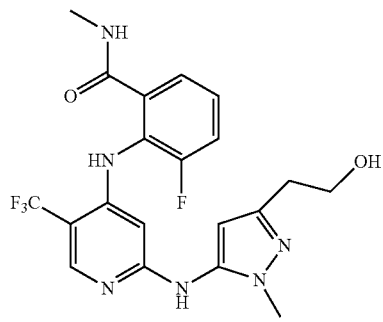 [SMILES: CNC(=O)c1cccc(F)c1Nc1cc(Nc2cc(CCO)nn2C)ncc1C(F)(F)F]

74(r). 2-{[2-({3-[(Dimethylamino)methyl]-1-methyl-1H-pyrazol-5-yl}amino)-5-(trifluoromethyl)-4-pyridinyl]amino}-3-fluoro-N-methylbenzamide

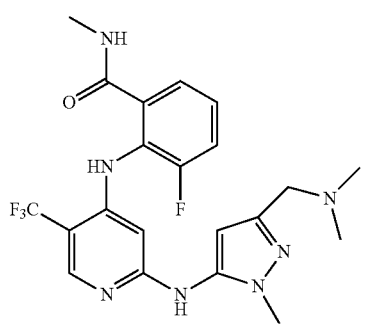 [SMILES: CNC(=O)c1cccc(F)c1Nc1cc(Nc2cc(CN(C)C)nn2C)ncc1C(F)(F)F]

Example 75

Following substantially the procedure of Example 72 the following compounds can be made using the appropriately substituted 5-aminopyrazole.

75(a). 2-({5-Chloro-2-[(1-ethyl-3-methyl-1H-pyrazol-5-yl)amino]-4-pyridinyl}amino)-3-fluoro-N-(methyloxy)benzamide

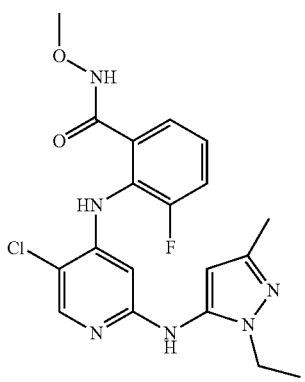 [SMILES: CCn1nc(C)cc1Nc1cc(Nc2c(F)cccc2C(=O)NOC)c(Cl)cn1]

75(b). 2-({5-Chloro-2-[(1,3-dimethyl-1H-pyrazol-5-yl)amino]-4-pyridinyl}amino)-3-fluoro-N-(methyloxy)benzamide

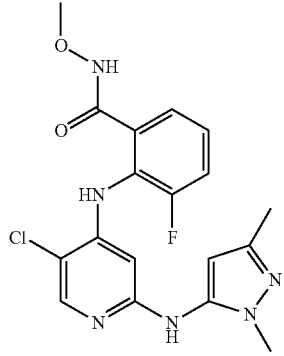 [SMILES: CONC(=O)c1cccc(F)c1Nc1cc(Nc2cc(C)nn2C)ncc1Cl]

75(c). 2-[(5-Chloro-2-{[1-ethyl-3-(hydroxymethyl)-1H-pyrazol-5-yl]amino}-4-pyridinyl)amino]-3-fluoro-N-(methyloxy)benzamide

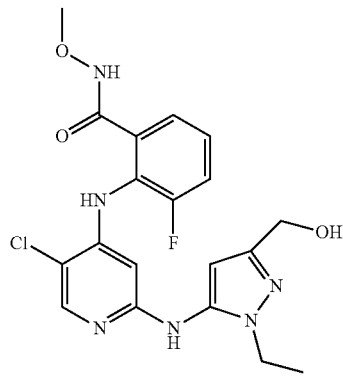 [SMILES: CCn1nc(CO)cc1Nc1cc(Nc2c(F)cccc2C(=O)NOC)c(Cl)cn1]

75(d). 2-[(5-Chloro-2-{[3-(hydroxymethyl)-1-methyl-1H-pyrazol-5-yl]amino}-4-pyridinyl)amino]-3-fluoro-N-(methyloxy)benzamide

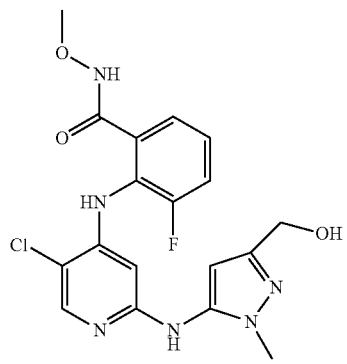 [SMILES: CONC(=O)c1cccc(F)c1Nc1cc(Nc2cc(CO)nn2C)ncc1Cl]

75(e). 2-{[5-Chloro-2-({3-[(dimethylamino)methyl]-1-ethyl-1H-pyrazol-5-yl}amino)-4-pyridinyl]amino}-3-fluoro-N-(methyloxy)benzamide

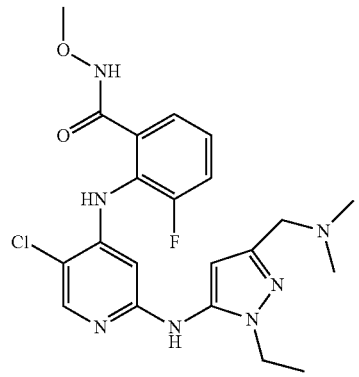 [SMILES: CCn1nc(CN(C)C)cc1Nc1cc(Nc2c(F)cccc2C(=O)NOC)c(Cl)cn1]

75(f). 2-({5-Chloro-2-[(1,5-dimethyl-1H-pyrazol-4-yl)amino]-4-pyridinyl}amino)-3-fluoro-N-(methyloxy)benzamide

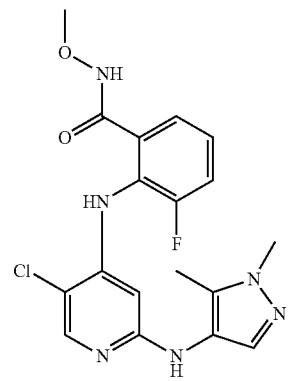 [SMILES: CONC(=O)c1cccc(F)c1Nc1cc(Nc2cnn(C)c2C)ncc1Cl]

Example 76

Following substantially the procedure of Example 41a or 41b the following compound can be made using 3-[(dimethylamino)methyl]-1-ethyl-1H-pyrazol-5-amine.

2-{[5-Chloro-2-({3-[(dimethylamino)methyl]-1-ethyl-1H-pyrazol-5-yl}amino)-4-pyridinyl]amino}-N-(methyloxy)benzamide

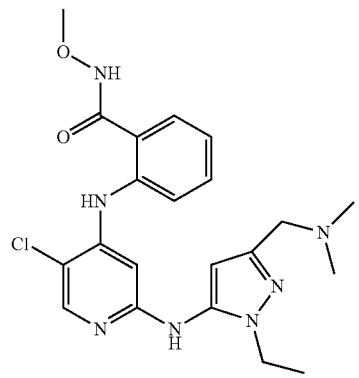 [SMILES: CCn1nc(CN(C)C)cc1Nc1cc(Nc2ccccc2C(=O)NOC)c(Cl)cn1]

Example 77

Following substantially the procedure of Example 73 the following compounds can be made using the appropriately substituted 5-aminopyrazole.

77(a). 2-({5-Chloro-2-[(1-ethyl-3-methyl-1H-pyrazol-5-yl)amino]-4-pyridinyl}amino)-4-fluoro-N-(methyloxy)benzamide

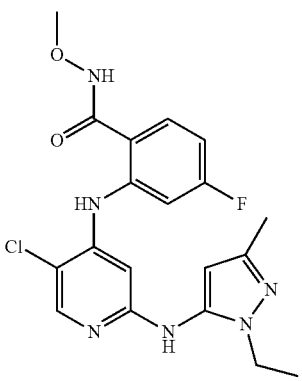 [SMILES: CCn1nc(C)cc1Nc1cc(Nc2cc(F)ccc2C(=O)NOC)c(Cl)cn1]

77(b). 2-({5-Chloro-2-[(1,3-dimethyl-1H-pyrazol-5-yl)amino]-4-pyridinyl}amino)-4-fluoro-N-(methyloxy)benzamide

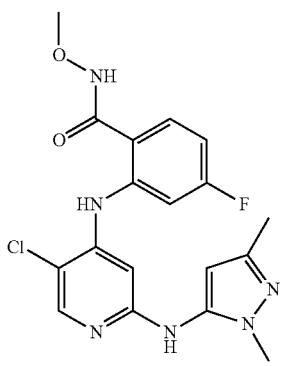 [SMILES: CONC(=O)c1ccc(F)cc1Nc1cc(Nc2cc(C)nn2C)ncc1Cl]

77(c). 2-[(5-Chloro-2-{[1-ethyl-3-(hydroxymethyl)-1H-pyrazol-5-yl]amino}-4-pyridinyl)amino]-4-fluoro-N-(methyloxy)benzamide

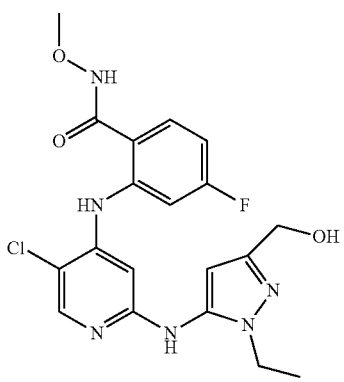 [SMILES: CCn1nc(CO)cc1Nc1cc(Nc2cc(F)ccc2C(=O)NOC)c(Cl)cn1]

77(d). 2-[(5-Chloro-2-{[1-ethyl-3-(2-hydroxyethyl)-1H-pyrazol-5-yl]amino}-4-pyridinyl)amino]-4-fluoro-N-(methyloxy)benzamide

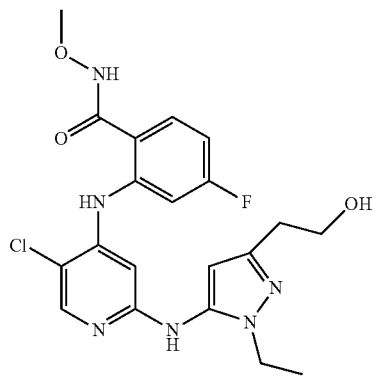 [SMILES: CCn1nc(CCO)cc1Nc1cc(Nc2cc(F)ccc2C(=O)NOC)c(Cl)cn1]

77(e). 2-[(5-Chloro-2-{[3-(hydroxymethyl)-1-methyl-1H-pyrazol-5-yl]amino}-4-pyridinyl)amino]-4-fluoro-N-(methyloxy)benzamide

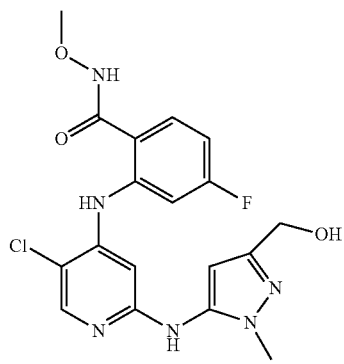 [SMILES: CONC(=O)c1ccc(F)cc1Nc1cc(Nc2cc(CO)nn2C)ncc1Cl]

77(f). 2-{[5-Chloro-2-({3-[(dimethylamino)methyl]-1-ethyl-1H-pyrazol-5-yl}amino)-4-pyridinyl]amino}-4-fluoro-N-(methyloxy)benzamide

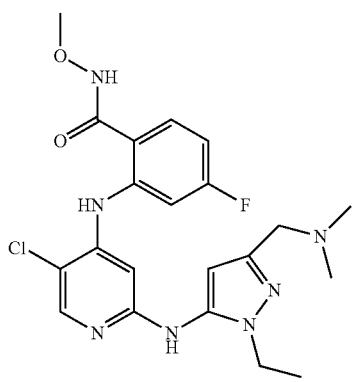 [SMILES: CCn1nc(CN(C)C)cc1Nc1cc(Nc2cc(F)ccc2C(=O)NOC)c(Cl)cn1]

77(g). 2-({5-Chloro-2-[(1,5-dimethyl-1H-pyrazol-4-yl)amino]-4-pyridinyl}amino)-4-fluoro-N-(methyloxy)benzamide

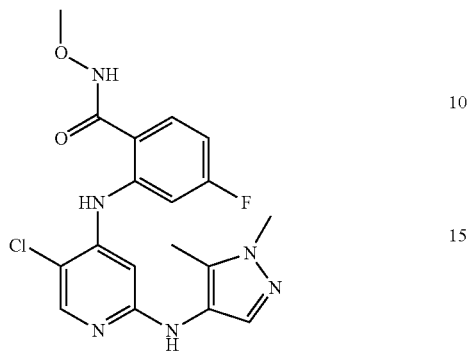

What is claimed is:

1. A method of treating or lessening the severity of mesothelioma in a human in need thereof, which comprises administering to such human a therapeutically effective amount of the compound:
2-[(5-Chloro-2-{[3-methyl-1-(1-methylethyl)-1H-pyrazol-5-yl]amino}-4-pyridinyl)amino]-N-(methyloxy)benzamide;
or a pharmaceutically acceptable salt thereof.

2. A method of treating or lessening the severity of pancreatic cancer in a human in need thereof, which comprises administering to such human a therapeutically effective amount of the compound:
2-[(5-Chloro-2-{[3-methyl-1-(1-methylethyl)-1H-pyrazol-5-yl]amino}-4-pyridinyl)amino]-N-(methyloxy)benzamide;
or a pharmaceutically acceptable salt thereof.

* * * * *

UNITED STATES PATENT AND TRADEMARK OFFICE
CERTIFICATE OF CORRECTION

PATENT NO. : 9,446,034 B2  Page 1 of 1
APPLICATION NO. : 14/887763
DATED : September 20, 2016
INVENTOR(S) : Jerry Leroy Adams et al.

It is certified that error appears in the above-identified patent and that said Letters Patent is hereby corrected as shown below:

On the Title Page

<u>Between Items (65) and (51),</u>
Related U.S. Application Data
(60) "No. 61,242,423" should be ---No. 61/242,432---

In the Specification

<u>Column 1,</u>
Line 11, No. "61/242,423" should be ---No. 61/242,432---

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*